(12) United States Patent
Chappa

(10) Patent No.: US 8,246,974 B2
(45) Date of Patent: Aug. 21, 2012

(54) MEDICAL DEVICES AND METHODS FOR PRODUCING THE SAME

(75) Inventor: Ralph A. Chappa, Prior Lake, MN (US)

(73) Assignee: SurModics, Inc., Eden Prairie, MN (US)

( * ) Notice: Subject to any disclaimer, the term of this patent is extended or adjusted under 35 U.S.C. 154(b) by 1612 days.

(21) Appl. No.: 11/102,465

(22) Filed: Apr. 8, 2005

(65) Prior Publication Data
US 2005/0196424 A1  Sep. 8, 2005

Related U.S. Application Data

(63) Continuation-in-part of application No. 10/835,530, filed on Apr. 29, 2004, now Pat. No. 8,021,680, and a continuation-in-part of application No. PCT/US2004/013327, filed on Apr. 29, 2004.

(60) Provisional application No. 60/467,419, filed on May 2, 2003.

(51) Int. Cl.
*A61F 2/00* (2006.01)
(52) U.S. Cl. .................. 424/423; 424/427; 606/167
(58) Field of Classification Search .................. None
See application file for complete search history.

(56) References Cited

U.S. PATENT DOCUMENTS

| | | | |
|---|---|---|---|
| 273,410 | A | 3/1883 | Wadleigh |
| 554,114 | A | 2/1896 | Evertz |
| 3,416,530 | A | 12/1968 | Ness |
| 3,625,214 | A | 12/1971 | Higuchi |
| 4,000,745 | A | 1/1977 | Goldberg |
| 4,069,307 | A | 1/1978 | Higuchi et al. |

(Continued)

FOREIGN PATENT DOCUMENTS
EP  414233  2/1991
(Continued)

OTHER PUBLICATIONS

Berger et al, "Intravitreal Sustained Release Corticosteroid-5-Fluoruracil Conjugate in the Treatment of Experimental Proliferative Vitrcoretinopathy," Investigative Ophthalmology & Visual Science, Oct. 1996, vol. 37, No. 2, pp. 2318-2325.

(Continued)

*Primary Examiner* — Robert A Wax
*Assistant Examiner* — Bethany Barham
(74) *Attorney, Agent, or Firm* — Pauly, Devries Smith & Deffner, L.L.C.

(57) ABSTRACT

Embodiments of the invention include coated medical devices that can elute one or more bioactive agents within the body, and methods for producing the same. In an embodiment, the invention includes a method of forming a coated medical device including depositing a coated composition onto a medical device having a roughened segment and a smooth segment. In an embodiment, the invention includes a method of forming a coated implantable medical device including depositing a coated composition onto a medical device having a body segment and a piercing segment. In an embodiment, the invention includes a medical device, a coated composition provided on the substrate surface, the composition including a bioactive agent and a polymer. The medical device includes an uncoated component wherein the edge of the coated composition is within 0.5 mm of the uncoated component. In an embodiment, the invention includes a method for disposing a coated composition on a medical device with an ultrasonically atomized spray stream including moving a spray stream in a pattern having a plurality of transverse sweeps and a plurality of longitudinal movements.

18 Claims, 27 Drawing Sheets

U.S. PATENT DOCUMENTS

| | | |
|---|---|---|
| 4,144,317 A | 3/1979 | Higuchi et al. |
| 4,146,036 A | 3/1979 | Dutcher et al. |
| 4,206,756 A | 6/1980 | Grossan |
| 4,209,019 A | 6/1980 | Dutcher et al. |
| 4,292,965 A | 10/1981 | Nash et al. |
| 4,300,557 A | 11/1981 | Refojo et al. |
| 4,304,765 A | 12/1981 | Shell et al. |
| 4,638,045 A | 1/1987 | Kohn et al. |
| 4,678,466 A | 7/1987 | Rosenwald |
| 4,764,377 A | 8/1988 | Goodson |
| 4,819,661 A | 4/1989 | Heil, et al. |
| 4,853,224 A | 8/1989 | Wong |
| 4,863,457 A | 9/1989 | Lee |
| 4,892,736 A | 1/1990 | Goodson |
| 4,953,564 A | 9/1990 | Berthelsen |
| 4,959,217 A | 9/1990 | Sanders et al. |
| 4,972,848 A | 11/1990 | Di Domenico et al. |
| 4,997,652 A | 3/1991 | Wong |
| 5,002,067 A | 3/1991 | Berthelsen et al. |
| 5,003,992 A | 4/1991 | Holleman et al. |
| 5,076,285 A | 12/1991 | Hess et al. |
| 5,098,443 A | 3/1992 | Parel et al. |
| 5,114,719 A | 5/1992 | Sabel et al. |
| 5,120,312 A | 6/1992 | Wigness et al. |
| 5,164,188 A | 11/1992 | Wong |
| 5,221,698 A | 6/1993 | Amidon et al. |
| 5,229,128 A | 7/1993 | Haddad et al. |
| 5,246,867 A | 9/1993 | Lakowicz et al. |
| 5,255,693 A | 10/1993 | Dutcher et al. |
| 5,300,108 A | 4/1994 | Rebell et al. |
| 5,300,114 A | 4/1994 | Gwon |
| 5,310,559 A | 5/1994 | Shah et al. |
| 5,314,419 A | 5/1994 | Pelling |
| 5,324,325 A | 6/1994 | Moaddeb |
| 5,364,343 A | 11/1994 | Apolet et al. |
| 5,372,577 A | 12/1994 | Ungerleider |
| 5,378,475 A | 1/1995 | Smith et al. |
| 5,385,148 A | 1/1995 | Lesh et al. |
| 5,395,618 A | 3/1995 | Darougar et al. |
| 5,405,376 A | 4/1995 | Mulier et al. |
| 5,423,777 A | 6/1995 | Tajiri et al. |
| 5,431,649 A | 7/1995 | Mulier et al. |
| 5,437,656 A | 8/1995 | Shikani et al. |
| 5,443,505 A | 8/1995 | Wong et al. |
| 5,447,724 A | 9/1995 | Helmus et al. |
| 5,449,382 A | 9/1995 | Dayton |
| 5,464,650 A | 11/1995 | Berg et al. |
| 5,466,233 A | 11/1995 | Weiner et al. |
| 5,472,436 A | 12/1995 | Fremstad |
| 5,476,511 A | 12/1995 | Gwon et al. |
| 5,501,856 A | 3/1996 | Ohtori et al. |
| 5,512,055 A | 4/1996 | Domb et al. |
| 5,525,348 A | 6/1996 | Whitbourne et al. |
| 5,545,208 A | 8/1996 | Wolff et al. |
| 5,556,633 A | 9/1996 | Haddad et al. |
| 5,578,075 A | 11/1996 | Dayton |
| 5,582,616 A | 12/1996 | Bolduc et al. |
| 5,591,227 A | 1/1997 | Dinh et al. |
| 5,605,696 A | 2/1997 | Eury et al. |
| 5,609,629 A | 3/1997 | Fearnot et al. |
| 5,624,411 A | 4/1997 | Tuch |
| 5,624,975 A | 4/1997 | Valencia |
| 5,637,113 A | 6/1997 | Tartaglia et al. |
| 5,645,592 A | 7/1997 | Nicolais et al. |
| 5,651,986 A | 7/1997 | Brem et al. |
| 5,673,473 A | 10/1997 | Johnson et al. |
| 5,679,400 A | 10/1997 | Tuch |
| 5,725,493 A | 3/1998 | Avery et al. |
| 5,766,242 A | 6/1998 | Wong et al. |
| 5,773,019 A | 6/1998 | Ashton et al. |
| 5,807,395 A | 9/1998 | Mulier et al. |
| 5,810,836 A | 9/1998 | Hussein et al. |
| 5,824,072 A | 10/1998 | Wong |
| 5,830,173 A | 11/1998 | Avery et al. |
| 5,833,715 A | 11/1998 | Vachon et al. |
| 5,837,313 A | 11/1998 | Ding et al. |
| 5,868,697 A | 2/1999 | Richter et al. |
| 5,877,224 A | 3/1999 | Brocchini et al. |
| 5,886,026 A | 3/1999 | Hunter et al. |
| 5,904,144 A | 5/1999 | Hammang et al. |
| 5,921,982 A | 7/1999 | Lesh et al. |
| 5,928,662 A | 7/1999 | Phillips |
| 5,972,027 A | 10/1999 | Johnson |
| 5,972,369 A | 10/1999 | Roorda et al. |
| 5,980,972 A | 11/1999 | Ding |
| 5,989,579 A | 11/1999 | Darougar et al. |
| 5,997,517 A | 12/1999 | Whitbourne |
| 6,001,386 A | 12/1999 | Ashton et al. |
| 6,033,582 A * | 3/2000 | Lee et al. .................. 216/37 |
| 6,053,924 A | 4/2000 | Hussein |
| 6,074,661 A | 6/2000 | Olejnik et al. |
| 6,091,978 A | 7/2000 | Johnson et al. |
| 6,096,070 A | 8/2000 | Ragheb et al. |
| 6,099,562 A | 8/2000 | Ding et al. |
| 6,102,887 A | 8/2000 | Altman |
| 6,110,483 A | 8/2000 | Whitbourne et al. |
| 6,117,456 A | 9/2000 | Lee et al. |
| 6,120,536 A | 9/2000 | Ding et al. |
| 6,129,933 A | 10/2000 | Oshlack et al. |
| 6,143,037 A | 11/2000 | Goldstein et al. |
| 6,153,252 A | 11/2000 | Hossainy et al. |
| 6,177,095 B1 | 1/2001 | Sawhney et al. |
| 6,187,370 B1 | 2/2001 | Dinh et al. |
| 6,197,324 B1 | 3/2001 | Crittenden |
| 6,203,556 B1 | 3/2001 | Evans et al. |
| 6,212,434 B1 | 4/2001 | Scheiner et al. |
| 6,214,008 B1 | 4/2001 | Illi |
| 6,214,901 B1 | 4/2001 | Chudzik et al. |
| 6,217,895 B1 | 4/2001 | Guo et al. |
| 6,248,112 B1 | 6/2001 | Gambale et al. |
| 6,251,090 B1 | 6/2001 | Avery et al. |
| 6,251,136 B1 | 6/2001 | Guruwaiya et al. |
| 6,251,418 B1 | 6/2001 | Ahern et al. |
| 6,254,921 B1 | 7/2001 | Chappa et al. |
| 6,287,285 B1 | 9/2001 | Michal et al. |
| 6,290,728 B1 | 9/2001 | Phelps et al. |
| 6,298,272 B1 | 10/2001 | Peterfeso et al. |
| 6,306,125 B1 | 10/2001 | Parker et al. |
| 6,306,426 B1 | 10/2001 | Olejnik et al. |
| 6,309,370 B1 | 10/2001 | Haim et al. |
| RE37,463 E | 12/2001 | Altman |
| 6,331,313 B1 | 12/2001 | Wong et al. |
| 6,344,035 B1 | 2/2002 | Chudzik et al. |
| 6,358,247 B1 | 3/2002 | Altman et al. |
| 6,360,129 B1 | 3/2002 | Ley et al. |
| 6,375,972 B1 | 4/2002 | Guo et al. |
| 6,395,326 B1 * | 5/2002 | Castro et al. .................. 427/2.24 |
| 6,399,144 B2 | 6/2002 | Dinh et al. |
| 6,399,655 B1 | 6/2002 | De Juan et al. |
| 6,399,704 B1 | 6/2002 | Laurin et al. |
| 6,406,754 B2 | 6/2002 | Chappa et al. |
| 6,451,373 B1 | 9/2002 | Hossainy et al. |
| 6,478,776 B1 | 11/2002 | Rosenman et al. |
| 6,497,691 B1 | 12/2002 | Bevins et al. |
| 6,501,994 B1 | 12/2002 | Janke et al. |
| 6,505,082 B1 | 1/2003 | Scheiner et al. |
| 6,506,411 B2 | 1/2003 | Hunter et al. |
| 6,544,544 B2 | 4/2003 | Hunter et al. |
| 6,547,787 B1 | 4/2003 | Altman et al. |
| 6,548,078 B2 | 4/2003 | Guo et al. |
| 6,562,051 B1 | 5/2003 | Bolduc et al. |
| 6,562,136 B1 | 5/2003 | Chappa et al. |
| 6,585,764 B2 | 7/2003 | Wright et al. |
| 6,595,958 B1 | 7/2003 | Mickley |
| 6,613,017 B1 | 9/2003 | Mickley |
| 6,653,426 B2 | 11/2003 | Alvarado et al. |
| 6,706,023 B1 | 3/2004 | Huttner et al. |
| 6,709,712 B2 | 3/2004 | Chappa et al. |
| 6,713,081 B2 | 3/2004 | Robinson et al. |
| 6,716,081 B2 | 4/2004 | Kim et al. |
| 6,716,196 B2 | 4/2004 | Lesh et al. |
| 6,719,750 B2 | 4/2004 | Varner et al. |
| 6,719,805 B1 | 4/2004 | Ahern |
| 6,726,918 B1 | 4/2004 | Wong et al. |
| 6,743,233 B1 | 6/2004 | Baldwin et al. |
| 6,764,470 B2 | 7/2004 | Dimick |
| 2001/0014717 A1 | 8/2001 | Hossainy et al. |

| | | | | | |
|---|---|---|---|---|---|
| 2001/0026834 A1 | 10/2001 | Chappa et al. | EP | 0923953 | 6/1998 |
| 2001/0029351 A1 | 10/2001 | Falotico et al. | EP | 0945148 | 9/1999 |
| 2002/0005206 A1 | 1/2002 | Falotico et al. | EP | 1374924 | 1/2004 |
| 2002/0007213 A1 | 1/2002 | Falotico et al. | EP | 1382302 | 1/2004 |
| 2002/0007214 A1 | 1/2002 | Falotico | JP | 02-036882 | 2/1990 |
| 2002/0007215 A1 | 1/2002 | Falotico et al. | JP | 09-194347 | 7/1997 |
| 2002/0013298 A1 | 1/2002 | Hunter | WO | WO89/05664 | 6/1989 |
| 2002/0018795 A1 | 2/2002 | Whitbourne et al. | WO | WO91/12779 | 9/1991 |
| 2002/0026176 A1 | 2/2002 | Varner et al. | WO | WO92/11895 | 7/1992 |
| 2002/0026236 A1 | 2/2002 | Helmus et al. | WO | WO92/15286 | 9/1992 |
| 2002/0032434 A1 | 3/2002 | Chudzik et al. | WO | WO-9315682 | 8/1993 |
| 2002/0032477 A1 | 3/2002 | Helmus et al. | WO | WO94/21308 | 9/1994 |
| 2002/0051730 A1 | 5/2002 | Bodnar et al. | WO | WO94/21309 | 9/1994 |
| 2002/0054900 A1 | 5/2002 | Kamath et al. | WO | WO95/03036 | 2/1995 |
| 2002/0062730 A1 | 5/2002 | Thornton | WO | WO97/10011 | 3/1997 |
| 2002/0091433 A1 | 7/2002 | Ding et al. | WO | WO97/37640 | 10/1997 |
| 2002/0107330 A1 | 8/2002 | Pinchuk et al. | WO | WO98/17331 | 4/1998 |
| 2002/0111590 A1 | 8/2002 | Davila et al. | WO | WO98/32474 | 7/1998 |
| 2002/0114823 A1 | 8/2002 | Sirhan et al. | WO | WO98/58690 | 12/1998 |
| 2002/0120326 A1 | 8/2002 | Michal | WO | WO99/01114 | 1/1999 |
| 2002/0133183 A1 | 9/2002 | Lentz et al. | WO | WO99/36071 | 7/1999 |
| 2002/0138048 A1 | 9/2002 | Tuch | WO | WO99/38546 | 8/1999 |
| 2002/0165265 A1 | 11/2002 | Hunter et al. | WO | WO99/55396 | 11/1999 |
| 2002/0168394 A1 | 11/2002 | Hossainy et al. | WO | WO00/02564 | 1/2000 |
| 2002/0188037 A1 | 12/2002 | Chudzik et al. | WO | WO00/12163 | 3/2000 |
| 2002/0188170 A1 | 12/2002 | Santamore et al. | WO | WO00/21584 | 4/2000 |
| 2002/0198511 A1 | 12/2002 | Varner et al. | WO | WO01/08718 | 2/2001 |
| 2003/0004209 A1 | 1/2003 | Hunter et al. | WO | WO01/23016 | 4/2001 |
| 2003/0014036 A1 | 1/2003 | Varner et al. | WO | WO01/30323 | 5/2001 |
| 2003/0021828 A1 | 1/2003 | Guo et al. | WO | WO01/32140 | 5/2001 |
| 2003/0031780 A1 | 2/2003 | Chudzik et al. | WO | WO01/36008 | 5/2001 |
| 2003/0039689 A1* | 2/2003 | Chen et al. .............. 424/468 | WO | WO-0178626 | 10/2001 |
| 2003/0054023 A1 | 3/2003 | Hughes | WO | WO01/87283 | 11/2001 |
| 2003/0060783 A1 | 3/2003 | Koole et al. | WO | WO01/87342 | 11/2001 |
| 2003/0065332 A1 | 4/2003 | TenHuisen et al. | WO | WO01/87372 | 11/2001 |
| 2003/0083646 A1 | 5/2003 | Sirhan et al. | WO | WO01/87373 | 11/2001 |
| 2003/0094736 A1 | 5/2003 | Qin et al. | WO | WO01/87374 | 11/2001 |
| 2003/0096131 A1 | 5/2003 | Beavers et al. | WO | WO01/87375 | 11/2001 |
| 2003/0120200 A1 | 6/2003 | Bergheim et al. | WO | WO01/87376 | 11/2001 |
| 2003/0157187 A1 | 8/2003 | Hunter | WO | WO02/17831 A2 | 3/2002 |
| 2003/0158598 A1 | 8/2003 | Ashton et al. | WO | WO02/20271 | 4/2002 |
| 2003/0165613 A1 | 9/2003 | Chappa et al. | WO | WO02/26139 | 4/2002 |
| 2003/0175324 A1 | 9/2003 | Robinson et al. | WO | WO02/26281 | 4/2002 |
| 2003/0181848 A1 | 9/2003 | Bergheim et al. | WO | WO02/056790 | 7/2002 |
| 2003/0190420 A1 | 10/2003 | Chappa et al. | WO | WO03/022323 | 3/2003 |
| 2003/0207856 A1 | 11/2003 | Tremble et al. | WO | WO03/026718 A1 | 4/2003 |
| 2003/0229333 A1 | 12/2003 | Ashton et al. | WO | WO03/063729 | 8/2003 |
| 2003/0232087 A1 | 12/2003 | Lawin et al. | WO | WO03/064015 | 8/2003 |
| 2003/0232122 A1 | 12/2003 | Chappa et al. | WO | WO03/065881 | 8/2003 |
| 2003/0236513 A1 | 12/2003 | Schwarz et al. | WO | WO03/099169 | 12/2003 |
| 2003/0236514 A1 | 12/2003 | Schwarz | WO | WO2004/000267 | 12/2003 |
| 2004/0006146 A1 | 1/2004 | Evans et al. | WO | WO2004/004821 | 1/2004 |
| 2004/0022853 A1 | 2/2004 | Ashton et al. | WO | WO2004/028477 A2 | 4/2004 |
| 2004/0034357 A1 | 2/2004 | Beane et al. | WO | WO-2004/098565 | 11/2004 |
| 2004/0037886 A1 | 2/2004 | Hsu | WO | WO2004/098565 A2 | 11/2004 |
| 2004/0044404 A1 | 3/2004 | Stucke et al. | WO | WO-2005/009297 | 2/2005 |
| 2004/0047911 A1 | 3/2004 | Lyu et al. | | | |
| 2004/0062875 A1 | 4/2004 | Chappa et al. | | | |
| 2004/0121014 A1 | 6/2004 | Guo et al. | | | |
| 2004/0133155 A1 | 7/2004 | Varner et al. | | | |
| 2004/0137059 A1 | 7/2004 | Nivaggioli et al. | | | |
| 2004/0142013 A1 | 7/2004 | Rubsamen | | | |
| 2004/0143314 A1 | 7/2004 | Sommer et al. | | | |
| 2004/0194704 A1 | 10/2004 | Chappa et al. | | | |
| 2005/0019371 A1 | 1/2005 | Anderson et al. | | | |
| 2005/0129732 A1 | 6/2005 | Rubsamen | | | |
| 2005/0147690 A1 | 7/2005 | Masters et al. | | | |
| 2005/0158449 A1 | 7/2005 | Chappa | | | |
| 2005/0240147 A1 | 10/2005 | Makower et al. | | | |

FOREIGN PATENT DOCUMENTS

| | | |
|---|---|---|
| EP | 0623354 | 4/1994 |
| EP | 0604022 | 6/1994 |
| EP | 0734721 | 3/1996 |
| EP | 0716836 | 6/1996 |
| EP | 0747069 | 12/1996 |
| EP | 0832655 | 6/1997 |
| EP | 0834282 | 4/1998 |
| EP | 0879595 | 4/1998 |

OTHER PUBLICATIONS

Berger et al. "Intravitreal Sustained Released Dexamethasone/5-FU Device in the Treatment of Experimental PVR," Investigative Ophthalmology & Visual Science, Mar. 15, 1994, vol. 35, No. 4, p. 1923.

Brown et al, "Characterization of Glucose-Mediated Insulin Release from Implantable Polymers," Journal of Pharmaceutical Sciences, vol. 85, No. 12, Dec. 1996.

Catz et al, "In Vitro Evaluations of Transdermal Levonorgestrel," Drug Design and Delivery, 1990, vol. 6, pp. 49-60.

Edelman et al, "c-myc in Vasculoproliferative Disease," Circulation Research, 1995: 76:176-182.

Eliaz et al, "Long-term Protection Against the Effects Tumor Necrosis Factor by Controlled Delivery of the Soluble p55 TNF Receptor," Cytokine, vol. 8, No. 6, Jun. 1996: pp. 482-487.

Flemmig et al. "Adjunctive controlled topical application of tetracycline HCI in the treatment of localized persistent or recurrent periodontitis," J. Clin. Periodontol 1996; 23:914-921.

Folkman. "How the field of controlled-release technology began, and its central role in the development of angiogenesis research." Biomaterials 1990, vol. 11 Novembe.

Friling et al, "A Role in Transforming Growth Factor B1 in the Control of Corneal Neovascularisation," in vivo 10: 59-64 (1996).

Goodson et al, "Clinical Responses Following Periodontal Treatment by Local Drug Delivery," Journal of Periodontology, Nov. 1985, pp. 81-87.

Huland et al, "In vivo system to detect long-term continuous release of bioactive interleukin-2 by immunopharmacological depot preparations in nude mice with human tumors," Journal of Cancer Research and Clinical Oncology (1995) 121: 285-290.

Ishihashi, et al, "Effects of Intravitreal Administration of Seroids on Experimental Subretinal Neovascularization in the Subhuman Primate," Arch Ophihalmol, May 1985, vol. 103, pp. 708-711.

Jafary, "Point-Counterpoint: Drug Eluting Stent Euphoria: A Revolutionary Step or Misguided Euphoria?" Transcatheter Cardiovascular Therapeutics, 2002.

Jaffe et al, "Safety and Pharmacokinetics of an Intraocular Fluocinolone Acetonide Sustained Delivery Device," Investigative Ophthalmology & Visual Science, Oct. 2000, vol. 41, No. 11, pp. 3569-3575.

Jaffee et al. "Intravitreal Sustained Release Triamcinolone/5-FU Conjugate Suspension in the Treatment of Experimental," Investigative Ophthalmology & Visual Science, Mar. 15, 1995, vol. 36, No. 4, p. S161.

Klugherz et al. "Twenty-eight-day efficacy and pharmacokinetics of the sirolirrus-eluting stent," Therapy and Prevention, Coronary Artery Disease 2002, 13:183-188.

Lees et al. "Angiogenesis in a Delayed Revascularization Model is Accelerated by Angiogenic Oligosaccharides of Hyaluronan," Laboratory Investigation, vol. 73, No. 2, pp. 259-266, 1995.

Lesser et al, "In vitro and in vivo studies of subcutaneous hydromorphone implants designed for the treatment of cancer pain," Pain. 65 (1996) 265-272.

Lopez et al, "Angiogenic potential of perivascularly delivered aFGF in a porcine model of chronic myocardial ischemia," American Journal of Physiology 274, H930-H936 1998.

Mortieç et al, "A Randomized Comparison of a Sirolimus-Eluting Stent with a Standard Stent for Coronary Revascularization." The New England Journal of Medicine, vol. 346. Jun. 6, 2002, No. 23, 1773-1780.

Ozaki et al, "Intravitreal Sustained Release of VEGF Causes Retinal Neovascularization in Rabbits and Breakdown of the Blood-Retinal Barrier in Rabbits and Primates," Exp. Eye Res. (1997) 64, 505-517.

Raman et al, "Coated stents: local pharmacology," Semin Intervent Cardiol 1998; 3: 133-137.

Regar et al, "Stent development and local drug delivery," British Medical Bulletin 2001; 59: 227-48.

Sellke et al, "Angiogenesis induced by acidic fibroblast growth factor as an alternative method of revascularization for chronic myocardial ischemia," Surgery 1996, 120:182-8.

Serruys et al. "Rapamycin eluting stent: the onset of a new era in interventional cardiology," Heart 2002: 87; 305-307.

Suzuki et al, "Stent-Based Delivery of Sirolimus Reduces Neointimal Formation in a Porcine Coronary Model," Circulation, 2001; 104:1188-1193.

Varner et al, "Development of a Minimally Invasive Intravitreal Implant for Drug Delivery," ARVO Abstracts Online, May 8, 2003 (4 pgs).

Whelan et al. "Mechanisms of drug loading and release kinetics," Semin Intervent Cardiol 1998; 3: 127-131.

Zhou et al. "A Multi-Drug Controlled-Release Implant for Intraocular Treatment of Proliferative Vitreoretinopathy," Proc. Int. Symp. Control. Re. Bioact. Mater., 24 (1997), pp. 625-626.

Zhou et at, "Development of a multiple-drug delivery implant for intraocular management of proliferative vitreoretinopathy," Journal of Controlled Release 55 (1998), pp. 281-295.

U.S. Appl. No. 10/976,193, "Method and Apparatus for Coating of Substrates", filed Oct. 27, 2004.

U.S. Appl. No. 09/523,767, "Sutureless Ocular Surgical Methods and Instruments for USB in Such Methods", filed Mar. 11, 2000.

Di Mario et al., "Radioactive Stents—A Dead End?", Current Interventional Cardiology Reports 2000, 2:87-88.

U.S. Appl. No. 09/523,767, "Sutureless Ocular Surgical Methods and Instruments for Use in Such Methods", filed Mar. 11, 2000.

European Examination Report, Communication pursuant to Article 94(3) EPC, from the European Patent Office in EP Patent Application No. 06 740 366.7, corresponding to U.S. Appl. No. 11/102,465, mailed May 5, 2009, pp. 1-3.

"Communication pursuant to Article 94(3) EPC, European Examination Report", from the European Patent Office in EP Patent Application No. 06740366.07-2319, corresponding to U.S. Appl. No. 11/102,465, mailed Oct. 19, 2010, (pp. 1-4).

"Response to Communication pursuant to Article 94 (3) EPC", Response to European Examination Report, dated Oct. 19, 2010, Filed in the European Patent Office on Feb. 22, 2011 for EP Patent Application No. 06740366.7, corresponding to U.S. Appl. No. 11/102,465, (pp. 1-13).

* cited by examiner

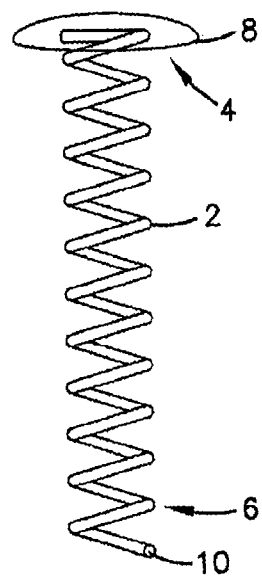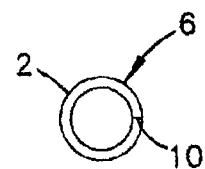
FIG. 1  FIG. 2
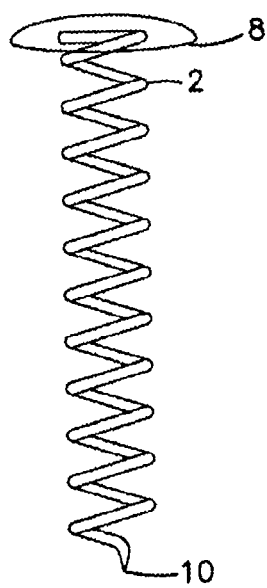
FIG. 3  FIG. 4

MEDICAL DEVICES AND METHODS FOR PRODUCING THE SAME

This application is a continuation-in-part of U.S. patent application Ser. No. 10/835,530, filed Apr. 29, 2004, now U.S. Pat. No. 8,021,680, issued Sep. 20, 2011, entitled "CONTROLLED RELEASE BIOACTIVE AGENT DELIVERY DEVICE," which application is incorporated herein by reference in its entirety. This application is also a continuation-in-part of PCT International Application No. PCT/US2004/013327, filed Apr. 29, 2004, entitled "CONTROLLED RELEASE BIOACTIVE AGENT DELIVERY DEVICE," which application is incorporated herein by reference in its entirety. U.S. patent application Ser. No. 10/835,530 and PCT International Application No. PCT/US2004/013327 both in turn claim the benefit of U.S. Provisional Application Ser. No. 60/467,419, filed May 2, 2003, which application is incorporated herein by reference in its entirety.

FIELD OF THE INVENTION

The invention relates to coated medical devices that can elute one or more bioactive agents and methods for producing the same.

BACKGROUND OF THE INVENTION

Coatings containing one or more bioactive agents can be placed on implanted medical devices to provide therapeutic benefits. For example, coatings can elute bioactive agents that help mitigate negative side effects of the medical device such as infections, inflammation, and restenosis. Coatings can also be put onto medical devices to function as drug-delivery systems that provide site-specific delivery of bioactive agents. In this manner, side effects of bioactive agents on non-targeted tissues can be minimized.

Some medical devices have surface features that remain uncoated by design. In order to dispose a coating on limited portions of these devices, it is desirable to be able to accurately control the application of the coating. However, many coating applicators lack accurate coating deposition control.

Many coated medical devices undergo stresses, such as frictional forces, in the course of their use. Accordingly, it is desirable that coatings be durable enough to resist damage during the course of use.

Therefore a need exists for systems and methods for accurately controlling the deposition of a coating. A need also exists for coatings that are durable enough to withstand forces incurred during the course of their use.

SUMMARY OF THE INVENTION

Embodiments of the invention include coated medical devices that can elute one or more bioactive agents within the body, and methods for producing the same. In an embodiment, the invention includes a method of forming a coated medical device including depositing a coated composition onto a medical device, the medical device having a roughened segment and a smooth segment, the coated composition having a leading edge provided on the roughened segment, the coated composition having a polymer and a bioactive agent.

In an embodiment, the invention includes a method of forming a coated implantable medical device including depositing a coated composition onto a medical device, the medical device having a body segment and a piercing segment, the coated composition having a leading edge provided over the body segment, the coating layer having a polymer and a bioactive agent.

In an embodiment, the invention includes a medical device having a substrate, a coated composition having an edge provided on the substrate surface, the composition including a bioactive agent and a polymer. The medical device includes an uncoated component disposed on the substrate surface, wherein the edge of the coating layer is within 0.5 mm of the uncoated component.

In an embodiment, the invention includes a medical device having a substrate, a first coated composition and a second coated composition. The first coated composition having an edge within 0.5 mm of the second coated composition edge.

In an embodiment, the invention includes a method for disposing a coated composition on a medical device with an ultrasonically atomized spray stream including atomizing a coating composition with an ultrasonic spray head to produce a spray stream, moving the spray stream in a pattern having a plurality of transverse sweeps and a plurality of longitudinal movements, wherein the longitudinal movements are less than about 0.4 mm and each longitudinal movement is separated from the next longitudinal movement by one or more transverse sweeps.

BRIEF DESCRIPTION OF THE DRAWINGS

The accompanying drawings, which are incorporated in and constitute a part of this specification, illustrate several aspects of the invention and together with the description of the preferred embodiments, serve to explain the principles of the invention. A brief description of the drawings is as follows:

FIG. 1 is a perspective view of an implantable device according to one embodiment of the invention.

FIG. 2 is a view from the bottom of the embodiment illustrated in FIG. 1.

FIG. 3 is a perspective view of an implantable device according to another embodiment of the invention.

FIG. 4 is a view from the bottom of the embodiment illustrated in FIG. 3.

DETAILED DESCRIPTION OF THE INVENTION

Figure 5:
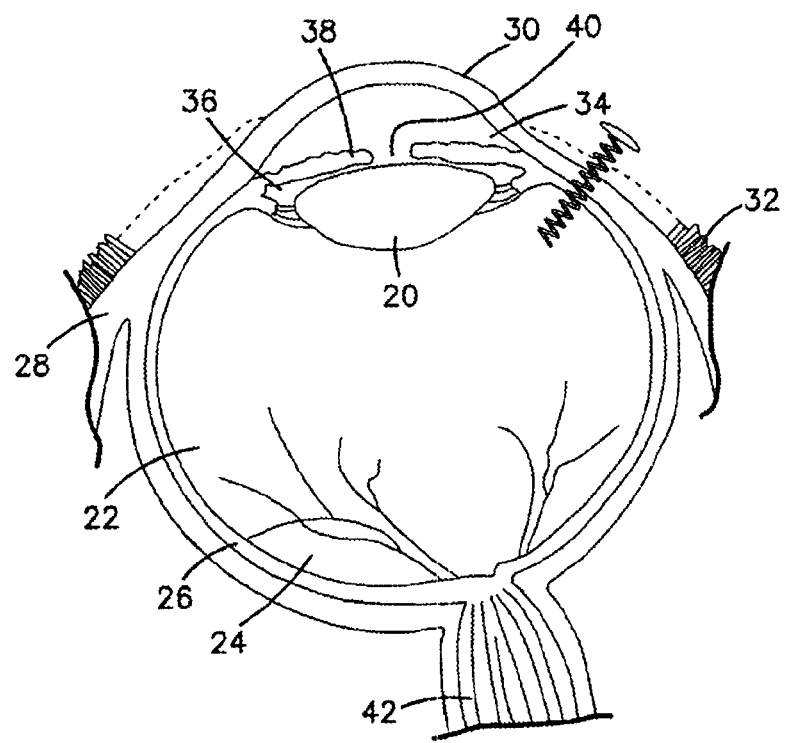
FIG. 5 illustrates transcleral placement of an implantable device according to one embodiment of the invention.

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

Various terms relating to the systems and methods of the invention are used throughout the specification.

As used herein, a "coating composition" refers to one or more vehicles (for example, solutions, mixtures, emulsions, dispersions, blends, and the like) used to effectively coat a surface. A "coated composition" refers to the effective combination of bioactive agent and one or more polymers on a surface of a medical device. The coated composition can be formed from one or more coating compositions, or in one or more layers, as will be apparent from the teaching herein.

As used herein, "biocompatible" means the ability of an object to be accepted by and to function in a recipient without eliciting a significant foreign body response (such as, for example, an immune, inflammatory, thrombogenic, or the like response). For example, when used with reference to one or more of the polymers of the invention, biocompatible refers to the ability of the polymer (or polymers) to be accepted by and to function in its intended manner in a recipient.

As used herein, "therapeutically effective amount" refers to that amount of a bioactive agent alone, or together with other substances (as described herein), that produces the desired effect (such as treatment of a medical condition such as a disease or the like, or alleviation of pain) in a patient. During treatment, such amounts will depend upon such factors as the particular condition being treated, the severity of the condition, the individual patient parameters including age, physical condition, size and weight, the duration of the treatment, the nature of the particular bioactive agent thereof employed and the concurrent therapy (if any), and like factors within the knowledge and expertise of the health practitioner. A physician or veterinarian of ordinary skill can readily determine and prescribe the effective amount of the bioactive agent required to treat and/or prevent the progress of the condition.

The term "implantation site" refers to the site within a patient's body at which the implantable device is placed according to the invention. In turn, a "treatment site" includes the implantation site as well as the area of the body that is to receive treatment directly or indirectly from a device component. For example, bioactive agent can migrate from the implantation site to areas surrounding the device itself, thereby treating a larger area than simply the implantation site. The term "incision site" refers to the area of the patient's body (the skin and transdermal area) at which an incision or surgical cut is made to implant the device according to the invention. The incision site includes the surgical cut, as well as the area in the vicinity of the surgical cut, of the patient.

The term "treatment course" refers to the dosage rate over time of one or more bioactive agents, to provide a therapeutically effective amount to a patient. Thus, factors of a treatment course include dosage rate and time course of treatment (total time during which the bioactive agent(s) is administered).

Medical devices may encounter forces, such as frictional forces, in the course of their use. For example, some medical devices encounter frictional forces when they are inserted and/or withdrawn from the tissues of a patient. Frictional forces can damage coated compositions in the form of coating delamination or coating failure wherein the coated composition delaminates and then falls off the device. Other types of forces can also damage coated compositions including compression, flexion, impact, and the like.

Embodiments of the invention include coated medical devices that can elute one or more bioactive agents within the body, and methods for producing the same. In an embodiment, the invention includes a method of forming a coated medical device including depositing a coated composition onto a medical device, the medical device having a roughened segment and a smooth segment, the coated composition having a leading edge provided on the roughened segment, the coated composition having a polymer and a bioactive agent.

In an embodiment, the invention includes a method of forming a coated implantable medical device including depositing a coated composition onto a medical device, the medical device having a body segment and a piercing segment, the coated composition having a leading edge provided over the body segment, the coating layer having a polymer and a bioactive agent.

Embodiments of the invention also include coating methods for precisely controlling the placement of a coated composition on a medical device. In many applications, it is desirable to maximize the amount of coated composition on a medical device. This is because maximizing the amount of coated composition can allow a greater amount of a bioactive agent to be delivered to a patient over a greater amount of time. This can extend the time period over which the medical device is effective. This could also extend the time period over which the medical device can be left in the body of a patient. Yet, some medical devices include segments or features that are to remain uncovered by the coated composition for proper performance (see Example 5). One approach to maximizing the amount of coated composition, while keeping some portion(s) uncovered, is to position an edge of the coated composition as close as possible to the segments or features that are to remain uncovered. This approach creates a need for coating techniques with positional accuracy.

Prior art coating applicators, such as those that rely on airflow for atomization (air-atomization), generally lack positional accuracy below about 1.0 mm. That is, the precise location on a medical device wherein a coating would begin cannot be reliably and reproducibly controlled with an accuracy of greater than about 1.0 mm. Therefore, if a given medical device had a segment which was to remain uncovered, the edge of a coating could not be consistently or reliably positioned closer than 1.0 mm from the uncovered segment because it may extend onto the uncovered portion due to the inaccuracy of the coating system.

Attempts have been made to improve the accuracy of air-atomization coating systems by using masking techniques to shield portions of the medical device from the spray stream. However, these attempts have failed to yield the desired end result in practice because of issues including build-up of coating material on the mask, webbing between the mask and the device, and/or an inability to process commercial quantities in a reproducible manner. Other coating techniques such as dip coating have similarly proven unsatisfactory because of a lack of positional accuracy below about 1.0 mm and/or an inability to precisely control the amount deposited. Still other techniques are too slow for use in commercial production, lack the ability to function properly with the solids percentages of the coating compositions used herein, don't work well with volatile organic solvents, and/or have clogging problems.

In an embodiment, the invention includes a method for disposing a coated composition on a medical device with an ultrasonically atomized spray stream including atomizing a coating composition with an ultrasonic spray head to produce a spray stream, moving the spray stream in a pattern having a plurality of transverse sweeps and a plurality of longitudinal movements, wherein the longitudinal movements are less than about 0.4 mm and each longitudinal movement is separated from the next longitudinal movement by one or more transverse sweeps.

In an embodiment, the invention includes a medical device having a substrate, a coated composition having an edge provided on the substrate surface, the composition including a bioactive agent and a polymer. The medical device includes an uncoated component disposed in or on the substrate surface, wherein the edge of the coating layer is within 0.5 mm of the uncoated component.

In an embodiment, the invention includes a medical device having a substrate, a first coated composition and a second coated composition. The first coated composition having an edge within 0.5 mm of the second coated composition edge.

In order to be properly introduced and utilized, implantable devices of all sorts of types are preferably designed to accommodate needs for advanceability, manipulability, and crossability to the distal end of the device as such is applied to the proximal end of the device. For purposes of this application, the following terms are given the following meaning.

Advanceability is the ability to transmit force from the proximal end of the device to the distal end of the device. The body member of the device should have adequate strength for advanceability and resistance to buckling or kinking. Manipulability is the ability to navigate tortuous vasculature or other body passages to reach the treatment site. A more flexible distal portion is known to improve manipulability. Thus, it can be desirable to provide a device having a body member with some elastomeric properties to improve flexibility in some applications. Crossability is the ability to navigate the device across tissue barriers or narrow restrictions in the vasculature.

Optimization of advanceability, manipulability, crossability and torque transmission can be accomplished by carefully choosing the device material and its physical characteristics, such as thickness of the material forming the body member. Further, in order to achieve a combination of desired properties at different parts of the device itself, the device can be fabricated to combine a plurality of components together to define a device body member. That is, a portion of the overall length of a body member of the device can comprise a different component than another portion. These one or more portions can comprise components of different physical characteristics and/or different materials. For example, a distal tip portion can be provided that is more resilient than the remainder of the device body member for better crossability and to provide a softer leading end of the device for abutting body internal membranes and the like. Different materials include different metallic materials or polymeric materials from one another, for example, or similar polymers of different densities, fillers, crosslinking or other characteristics. In particular, a portion of a device body member can comprise a material chosen for flexibility to allow flexion of the device during residence within the body (for example, in such areas as joints, where movement of the tissues in the area is likely) while another portion can comprise a material chosen for axial and/or torque transmission.

According to the present invention, a device has been developed that can be used to treat any implantation site within the body in which it is desirable to provide controlled release of one or more bioactive agents. In preferred embodiments, the device can be used to provide one or more bioactive agents to a treatment site that comprises a limited access region of the body, such as the eye, ear, brain, spine, and joints. More specifically, the device of the invention includes a body member having a direction of extension and at least a portion of the body member deviating from the direction of extension, and a polymeric coating composition in contact with the body member. The body member and polymeric coating composition are configured to provide controlled release of a bioactive agent to a treatment site. As described herein, controlled release at the treatment site can mean control both in dosage (including dosage rate and total dosage) and duration of treatment.

To facilitate discussion of the invention, use of the invention to treat an eye will be addressed. Eyes are selected as a result of the particular difficulties encountered when treating medical conditions of the eye, as described above. Further, in terms of lowering the risk of damage to body tissues while providing a superior device, the advantages of this controlled release device can be clearly presented. However, it is understood that the device and methods disclosed are applicable to any treatment needs. For example, embodiments of the invention can be used for treatment of limited access regions of the body where controlled release of a bioactive agent is desired during treatment, such as, for example, the central nervous system (the brain and spinal cord), the ear (such as the inner ear), and joints. Embodiments of the invention can also be used for treatment of non-limited access regions of the body.

In one aspect, the invention provides a controlled release bioactive agent delivery device comprising: (a) a body member having a direction of extension, a longitudinal axis along the direction of extension, and a proximal end and a distal end, wherein at least a portion of the body member deviates from the direction of extension; and (b) a polymeric coated composition in contact with the body member, the polymeric coated composition comprising a first polymer, a second polymer, and a bioactive agent, wherein the first polymer comprises polyalkyl(meth)acrylate, aromatic poly(meth)acrylate, or a combination of polyalkyl(meth)acrylate and aromatic poly(meth)acrylate, and wherein the second polymer comprises poly(ethylene-co-vinyl acetate).

Generally speaking, the body member of the implantable device is the portion of the controlled release device that is inserted into a patient. The body member can be described as including a proximal end (which is located, upon implantation, towards the exterior of the body), a distal end (which is located, upon implantation, towards the interior of the body), and a longitudinal axis. In use, at least a portion of the body member is inserted into a patient's body. For example, in some embodiments, it can be preferable to position less than 100% of the body member inside the patient's body. The amount of the body member positioned within the body can be determined by the interventionalist, based upon such factors as desired treatment parameters, the particular configuration of the device, the implantation site, and the like.

The body member further includes a direction of extension, and in preferred embodiments, at least a portion of the body member deviates from the direction of extension. In preferred embodiments, the body member includes at least two, three, four, five, six, seven, eight, nine, ten, or more deviations from the direction of extension. In some alternative embodiments, where the body does not include multiple deviations from the direction of extension, the body member can be provided in a "J" or a hook-type configuration.

The deviations from the direction of extension can be provided in any suitable configuration. Exemplary embodiments of such deviations will be described herein for illustrative purposes only, and without intending to be bound by any particular embodiment described herein. The deviations need not be rounded or arcuate. For example, in some embodiments, the body member is provided with a Z-shaped configuration, such that the deviations are angular. Moreover, the deviations need not be in a regular pattern, but can alternatively be provided in a random manner, such that the body member contains random curls or turns. In some embodiments, the deviations are provided in a patterned configuration about the longitudinal axis. Examples of these patterned embodiments include coils, spirals, or patterned Z-shaped turns in the body. Alternatively, the deviations can be provided in a random or non-patterned configuration about the longitudinal axis. According to these particular non-patterned embodiments, the distance of the individual deviations from the longitudinal axis to the outermost periphery of the body member can be selected to provide a desired overall profile of the body member, depending upon the application of the device. For example, it can be desirable, in some applications, to provide an overall profile of the body member having an hourglass shape, alternating ring circumference shapes, and the like.

In some embodiments, the deviations from the direction of extension can be provided in the form of rings. Such individual rings can be concentric (that is, having a common axis, or being coaxial about the longitudinal axis) or eccentric (deviating from a circular path). According to these embodiments, the individual rings are noncontiguous along the body member length, thereby forming individual ribs at positions along the direction of extension of the body member.

Preferred configurations of the body member are coiled or spiral. Generally, in a coil configuration, the individual rings of the coil rotate about the longitudinal axis, and the overall coil is substantially symmetrical about the longitudinal axis. A preferred coil is composed of multiple rings that are substantially similar in circumference along the length, from proximal to distal, of the device. In some preferred embodiments, the rings form a spiral pattern, wherein the circumference of the rings changes over the length of the device. Preferably, the circumference of the rings decreases toward the distal direction of the device, so that the largest ring circumference is located at the proximal region of the device, and the smallest ring circumference is located at the distal region of the device.

Inclusion of deviating portions of the body member provides an increased surface area for delivery of a bioactive agent to an implantation site as compared to a linear device having the same length and/or width. This can provide advantages during use of the device, since this configuration allows a greater surface area to be provided in a smaller length and/or width of the device. For example, in some applications, it can be desirable to limit the length of the device. For example, as will be discussed in more detail herein, it is desirable to limit the length of implants in the eye to prevent the device from entering the central visual field of the eye and to minimize risk of damage to the eye tissues. By providing a body member that has at least a portion of the body member deviating from the direction of extension, the device of the invention has greater surface area (and thus can hold a greater volume of bioactive agent) per length of the device without having to make the cross section of the device, and thus the size of the insertion incision, larger.

Still further, in preferred embodiments, the shape of the body member can provide a built-in anchoring system that reduces unwanted movement of the device and unwanted ejection of the device out of the patient's body, since the shape of the body member requires manipulation to remove it from an incision. For example, for a coil-shaped body member, the device would require twisting, and a Z-shaped body member would require back and forth movement, to remove the device from the implantation site. According to some preferred embodiments, the device does not require additional anchoring mechanisms (such as suturing) to the body tissues, as a result of the self-anchoring characteristics of the device itself. As described in more detail herein, inclusion of a cap 8 on the device can provide further anchoring features of the device.

In some embodiments, when the body member includes two or more deviations from the direction of extension, the spacing of the individual deviations can be selected to provide an optimum combination of such features as increased coatable surface area, overall dimensions of the device, and the like. For example, when the body member is provided in the form of a coil that includes two or more deviations from the direction of extension, the distance between the individual coils can be selected to be equal to or greater than the diameter of the material forming the body member. In some aspects, if the distance between coils is less than the diameter of the material forming the body member, the amount of coatable surface area of the body member can decrease, since it can be more difficult to access portions of the surface area of the body member with the coating compositions. In one illustrative embodiment of this aspect of the invention, the body member is formed of a material having a diameter of 0.5 mm, and the distance between each coil of the body member is at least 0.5 mm. These principals can be applied to any configuration of the body member and is not limited to coiled configurations.

The overall dimensions of the implantable device can be selected according to the particular application. For example, the length and/or width of the device can be selected to accommodate the particular implantation site. Some factors that can affect the overall dimensions of the implantable device include the potency of any bioactive agent to be delivered (and thus the volume of bioactive agent required, which impacts the surface area of the device, as discussed herein), the location of the implantation site within the body (for example, how far within the body the implantation site is located), the size of the implantation site (for example, a small area such as the eye or inner ear, or a larger area, such as a joint or organ area), the tissue surrounding the implantation site (for example, vascular tissue or hard, calcinous tissue, such as bone), and the like.

By way of example, when the implantable device is used to deliver bioactive agent(s) to the eye, the device is preferably designed for insertion through a small incision that requires few or no sutures for scleral closure at the conclusion of the surgical procedure. As such, the device is preferably inserted through an incision that is no more than about 1 mm in cross-section, for example, in the range of about 0.25 mm to about 1 mm in diameter, preferably in the range of about 0.25 mm to about 0.5 mm in diameter. As such, the cross-section of the material forming the body member 2 is preferably no more than about 1 mm, for example, in the range of about 0.25 mm to about 1 mm in diameter, preferably in the range of about 0.25 mm to about 0.5 mm in diameter. When the material forming the body member 2 is not cylindrical, the largest dimension of the cross-section can be used to approximate the diameter of the body member for this purpose, for example, when the body member cross-section is square.

When used to deliver bioactive agent(s) to the eye, the body member of the controlled release device preferably has a total length from its proximal end to its distal end that is less than about 1 cm, for example, in the range of about 0.25 cm to about 1 cm. Upon implantation, the body member is positioned within the eye, such that the portion of the controlled delivery device that delivers bioactive agent to the eye chamber is positioned near the posterior segment of the eye. When the controlled delivery device includes a cap 8, the cap is preferably provided with a thickness of less than about 1 mm, more preferably less than about 0.5 mm. According to this particular embodiment, the total length of the controlled delivery device is less than about 1.1 cm, preferably less than about 0.6 cm.

Turning to FIG. 1, a preferred embodiment of the controlled delivery device is illustrated. The controlled delivery device includes a body member 2 having a proximal end 4 and a distal end 6. FIG. 1 illustrates the body member in a coil configuration. According to this embodiment, the coil shape of the body member allows the device to be screwed or twisted into the body through an incision approximately the same size as the outer diameter of the material forming the body member 2. Still further, the coil shape of the body member can act as an anchoring mechanism to maintain the controlled delivery device within the implantation site, and can prevent unwanted movement of the device and unwanted ejection of the device from the implantation site and/or the body. As a result of the coil shape, the controlled delivery device is twisted and unscrewed out of the body during removal of the device.

The distal end 6 of the body member 2 can be positioned at any desirable location relative to the longitudinal axis of the body member. As shown in FIGS. 1 and 2, the distal end 6 of the body member according to one embodiment of the invention can include a tip 10 that is spaced from the longitudinal axis. This configuration is similar to a standard "cork screw" type configuration. In use, the device is inserted through the incision site and then twisted until the controlled delivery device is properly positioned at the treatment site.

Another embodiment is shown in FIGS. 3 and 4, wherein the distal end 6 of the body member includes tip 10 that is positioned at the longitudinal axis of the body member 2. In some embodiments, placement of the tip 10 of the body member 2 at the longitudinal axis can provide advantages, such as ease of insertion of the device at the distal end. It will be readily apparent that various other configurations of the distal end of the body member can be provided, depending upon the desired application.

Further, the proximal end 4 of the body member 2 can also be positioned at any desirable location relative to the longitudinal axis of the body member. FIGS. 1 and 3 illustrate the proximal end 4 of the body member as spaced from the longitudinal axis. However, the proximal end 4 of the body member can be provided at the longitudinal axis as well (not shown in the figures). In some embodiments, placement of the proximal end 4 of the body member 2 at the longitudinal axis can provide advantages, such as ease of fabrication of the device, increased mechanical strength, improved translation of force (since a uniform force can be applied and translated to the body member, with less risk of bending or other deformation of the body member), and the like.

In general, materials used to fabricate the body member 2 are not particularly limited. In some embodiments, the body member 2 can be fabricated of a flexible material, so that small movements of the controlled delivery device will not be translated to the implantation site. In some embodiments, as described in further detail herein, it can be preferable to fabricate at least the distal end 6 of the body member 2 of a rigid, non-pliable material. For example, when the device is designed for implantation in the eye, it is preferable to fabricate the device of a rigid material, to provide improved implant/explant characteristics to the device. In some embodiments, as described herein, it can be preferable to fabricate the body member 2 of a material having shape memory and/or superelastic characteristics.

In some embodiments, the body member 2 can be fabricated from any suitable material used to manufacture medical devices, such as, for example, stainless steel (for example, 316L); platinum; titanium; and gold; and such alloys as cobalt chromium alloys, nitinol, or the like. In further embodiments, suitable ceramics can be used to fabricate the body member 2, such as, for example, silicon nitride, silicon carbide, zirconia, alumina, glass, silica, sapphire, and the like. In still further embodiments, the body member 2 can be fabricated of a suitable composite material, such as composite materials commonly used to fabricate implantable devices. Such composite materials can, in some embodiments, provide such advantages as increased strength of the material, as well as increased flexibility. Examples of suitable composite materials include polymers or ceramics (such as high density polyethylene (HDPE), ultra high molecular weight polyethylene (UHMWPE), polymethylmethacrylate bone cement (PMMA), dental polymer matrix (such as crosslinked methacrylate polymers), and glass-ceramics) reinforced with fibers or particulate material (such as carbon fibers, bone particles, silica particles, hydroxyapatite particles, metal fibers or particles, or zirconia, alumina, or silicon carbide particles). Nano-composite materials are also contemplated.

In one embodiment, the body member 2 is fabricated of a nonbiodegradable polymer. Such nonbiodegradable polymers are well known and can include, for example, oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; and vinyls such as ethylene, propylene, styrene, vinyl chloride, vinyl acetate, and vinylidene difluoride. Examples of condensation polymers include, but are not limited to, nylons such as polycaprolactam, polylauryl lactam, polyhexamethylene adipamide, and polyhexamethylene dodecanediamide, as well as polyurethanes, polycarbonates, polyamides, polysulfones, poly(ethylene terephthalate), polylactic acid, polyglycolic acid, polydimethylsiloxanes, and polyetherketone. Other suitable nonbiodegradable polymers include silicone elastomers; silicone rubber; polyolefins such as polypropylene and polyethylene; homopolymers and copolymers of vinyl acetate such as ethylene vinyl acetate 2-pyrrolidone copolymer; polyacrylonitrile butadiene; fluoropolymers such as polytetrafluoroethylene and polyvinyl fluoride; homopolymers and copolymers of styrene acrylonitrile; homopolymers and copolymers of acrylonitrile butadiene styrene; polymethylpentene; polyimides; natural rubber; polyisobutylene; polymethylstyrene; latex; and other similar nonbiodegradable polymers.

At least a portion of the body member 2 can deviate from the direction of extension prior to, during, and after insertion of the device in the body. Alternatively, the device can be fabricated of a material having shape memory and/or superelastic characteristics that allow the device to be deformed into a configuration that is more easily inserted into the body. In one such embodiment, for example, the body member can be deformed into a substantially linear configuration, for insertion into the body. According to this particular embodiment, the body member can return to its original shape after it is inserted into the body. In this embodiment, the body member of the device has a "memory shape" that it will assume under certain conditions. For example, the body member can have a zigzag or coiled memory shape. When the interventionalist desires to implant the device into the body, the interventionalist can deform the device into a substantially linear shape for insertion of the device through an incision the size of the cross section of the linear shaped device. Upon implantation of the device into the body, the device can then resume its zigzag, coiled, or other memory shape. Preferably, the overall dimensions of the controlled delivery device (the maximum length and width) according to these shape memory embodiments do not significantly change by virtue of utilization of the shape memory material and deformation of the body member for implantation and/or explantation of the device in the body.

Shape memory alloys generally have at least two phases, namely, a martensite phase, which has a relatively low tensile strength and which is stable at relatively low temperatures, and an austenite phase, which has a relatively high tensile strength and which is stable at temperatures higher than the martensite phase. The shape memory characteristics are imparted to the material by heating the material to a temperature above the temperature at which the austenite phase is stable. While the material is heated to this temperature, the device is held in the "memory shape," which is the shape that is desired to be "remembered." Materials having shape memory and/or superelastic characteristics are well known and can include, for example, shape memory alloys (SMA) such as nitinol (a nickel-titanium alloy), and shape memory polymers (SMP) such as AB-polymer networks based upon oligo(e-caprolactone)dimethylacrylates and n-butyl acrylate. Such materials and methods of imparting shape memory characteristics are known and will not be described further herein.

Preferably, the controlled delivery device of the invention takes advantage of the material properties of the body member (for example, superelastic properties) to extend the body member into a linear shape. Once placed at the implantation site in an unconstrained form, the body member can resume its memory shape.

The distal end 6 of the body member can include any suitable configuration, depending upon the application of the device and the site of the body at which the device is to be implanted. For example, in some embodiments, the distal end 6 can be blunt or rounded. In preferred embodiments, the distal end 6 of the body member is configured to pierce the body during implantation of the device into the body. For example, the distal end 6 of the body member can include a sharp or pointed tip. In one preferred embodiment, the distal end 6 of the body member has a ramp-like angle. Preferably, the device according to this embodiment can be utilized to make an incision in the body, rather than requiring separate equipment and/or procedures for making the incision site. If the distal end 6 of the body member 2 is used to pierce the body during insertion, at least the distal end 6 is preferably fabricated of a rigid, non-pliable material suitable for piercing the body. Such materials are well known and can include, for example, polyimide and similar materials. In one such preferred embodiment, the distal end 6 of the body member 2 is utilized to pierce the eye for insertion of the controlled delivery device in the interior of the eye.

In another preferred embodiment, the distal end 6 of the body member 2 can be shaped or bent to form a portion (for example, the distal-most portion of the body member) that is parallel to the longitudinal axis. In one embodiment illustrated in FIGS. 3 and 4, for example, the distal end 6 includes a sharp or pointed tip that is parallel to the longitudinal axis. According to this particular embodiment, the tip located at the distal end 6 of the body member is perpendicular to the plane of incision, thus providing a self-starting tip of the device. While these figures illustrate a sharp tip of the body member, it is understood that any suitable configuration of the distal tip can be provided, utilizing the teaching herein.

The body member 2 can be fabricated from a solid material (a material that does not contain a lumen) or a material containing a lumen, as desired. In the embodiment illustrated in FIGS. 1 to 4, for example, the body member 2 is fabricated from a solid material that is shaped into a coil. Alternatively, the body member 2 can be fabricated from a tubular material that includes a lumen. The choice of a solid or lumen-containing material is not critical to the invention and can be determined based upon availability of materials and processing considerations.

When included, the lumen(s) can extend along the length of the body member 2 or only a portion of the length of the body member 2, as desired. In some embodiments, the lumen(s) can serve as a delivery mechanism for delivery of a desired substance to the implantation site. The substance delivered via the lumen can comprise any of the bioactive agents described herein. The substance delivered via the lumen can be the same or different bioactive agent(s) from that included in the coating composition. Further, the substance can be provided in addition to the bioactive agent of the polymeric coating composition, or in place of the bioactive agent. For example, in one embodiment, one or more substances can be delivered via the lumen, and one or more bioactive agents can be provided to the implantation site from the coated composition.

In some embodiments, the lumen can contain a polymeric coated composition as described herein. According to these particular embodiments, the body member of the device can be provided with or without a coating on its external surface. In some such embodiments, the lumen can be utilized to deliver the bioactive agent(s) to the implantation site. For example, the lumen can contain the polymeric coated composition, including first polymer, second polymer, and bioactive agent. According to this particular embodiment, the body member can be provided with a coating on an external surface comprising the first polymer and second polymer only (that is, lacking any bioactive agent). Thus, the bioactive agent is provided to the implantation site in this embodiment principally via the lumen of the body member. In other embodiments, the lumen can include the inventive polymeric coated composition (including first polymer, second polymer, and bioactive agent), and the body member is not provided with a coated composition on its external surface.

The lumen can contain any combination of elements, as desired. For example, in some embodiments, the lumen can include only the substance to be delivered. In other embodiments, the lumen can include the substance to be delivered, as well as the polymeric coated composition. The particular combination of elements to be included in the lumen can be selected depending upon the desired application of the device.

When the lumen is to be provided with a substance and/or polymeric coating composition, the lumen can be filled with the desired substance and/or polymeric coating composition prior to inserting the device into the body, or after the device has been inserted into the body. When it is desired to fill the device with the substance after insertion into the body, a port can be provided near the proximal end 4 of the body member 2 for such purpose. The port is in fluid communication with the lumen(s) of the body member and can also be used for refilling the device with the substance and/or polymeric coating composition after implantation, when desired.

When the device includes a port, the port is preferably designed such that the needle of an injection mechanism (for example, a syringe) can be inserted into the port and the material to be included in the lumen injected by the injection mechanism. Thus, the material can travel through the port and into the lumen(s) of the body member. The port preferably forms a snug seal about the needle of the injection mechanism to prevent leakage of the material out of the port around the injection mechanism and to provide sterile injection of material into the lumen(s). If desired, fittings or collars (not shown), through which an injection mechanism can be inserted and which form a snug seal about the injection mechanism, can be mounted on the port. Upon injection of the material into the delivery device, the needle of the injection mechanism is removed from the port and the port sealed. Sealing can be accomplished by providing a removable cover (not shown) on the port that can be removed for injection of the substance and replaced when the material has been injected. In a preferred embodiment, the port is fabricated of a self-sealing material through which the injection mechanism can be inserted and which seals off automatically when the injection mechanism is removed. Such materials are known and include, for example, silicone rubber, silicone elastomers, polyolefin, and the like.

In further embodiments, when the device includes more than one lumen, the device can include more than one port. For example, each lumen can be in fluid communication with a plurality of ports. These ports are similar to the single port described above. If desired, the lumens and ports can be arranged such that each lumen can be filled with a different material through a corresponding port (for example, each lumen has its own dedicated port). It can be desirable to include more than one lumen when it is desirable to deliver more than one additional material to the implantation site.

In embodiments where it is desired to deliver one or more additional substances to the implantation site via one or more lumens, the individual lumens can include one or more apertures to allow such delivery. In one embodiment, such apertures are provided at the distal end 6 of the device. In other embodiments, the apertures are provided along the length of the body member 2. The number and size of the apertures can vary depending upon the desired rate of delivery of the substance (when provided) and can be readily determined by one of skill in the art. The apertures are preferably designed such that the substance to be delivered is slowly diffused rather than expelled as a fluid stream from the device. For example, when the device is implanted in the eye, it is preferable to deliver the substance through slow diffusion rather than expulsion of the substance as a fluid stream, which can damage the delicate tissues of the eye. In some embodiments, the polymeric coating composition in contact with the body can provide a particular porosity to the substance and can assist in controlling the rate of diffusion of the substance from the lumen. When included in the device, the particular location of the apertures can be situated so as to deliver the substance at a particular location once the device is implanted into the body.

In another embodiment, when the body member 2 includes a lumen for delivery of an additional substance to the implantation site, the material forming the body member 2 can be chosen to be permeable (or semi-permeable) to the substance to be delivered from the lumen. According to this particular embodiment, the material can be chosen depending upon the particular application of the device and the substance to be delivered and can be readily determined by one of skill in the art. Examples of suitable permeable materials include polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, silicone rubbers, porous fibers, and the like.

According to these particular embodiments, the material used to fabricate the body member 2 can be chosen to provide a particular rate of delivery of the substance, which can be readily determined by one of skill in the art. Further, the rate of delivery of the substance can be controlled by varying the percentage of the body member 2 formed of the permeable (or semi-permeable) material. Thus, for example, to provide a slower rate of delivery, the body member 2 can be fabricated of 50% or less permeable material. Conversely, for a faster rate of delivery, the body member 2 can be fabricated of greater than 50% of permeable material. When one or more portions of the body member 2, rather than the whole body member 2, is fabricated of a permeable or semi-permeable material, the location of the permeable or semi-permeable material can be situated so as to deliver the substance at a particular location once the device is implanted at the implantation site.

In another embodiment, the lumen of the body member 2 can include impermeable dividers located along the length of the lumen. Thus, the lumen of the body member can contain a plurality of compartments, each of which can be filled with a different substance, as desired. These compartments could be filled prior to insertion through an injection port located, for example, in the side of each compartment. In another embodiment, the device can be filled after it is implanted by providing a plurality of conduits, each conduit in fluid communication with a corresponding compartment. These conduits can be provided within the wall of the body member 2, along the circumference of the body member 2. The substances could then be injected through a plurality of ports, each port in fluid communication with a corresponding conduit. Thus, a substance could be injected into the first compartment just below the cap 8 by a port in the center of the cap 8, which delivers the substance directly into the first compartment. A substance injected into the second port, would flow through conduit and would flow through an aperture in the wall of body member 2 into second compartment, and so on. The substance(s) to be delivered can be delivered to the implantation site via any of the methods described herein for the lumen(s).

In another embodiment, each lumen or compartment (as desired) can be designed for selected "opening" or activation by a laser (via heat or photodisruption). For example, a laser could be used to create apertures in the walls of the desired lumen and/or compartment when the particular substance is to be delivered. As such, release of each substance could be controlled upon demand by an interventionalist. Preferably, when a laser is utilized to create such apertures, the wavelength and temperature are controlled to minimize any effects on the polymeric coating composition.

In preferred embodiments, the body member 2 can be fabricated in a way that further increases the surface area of the body member, preferably without increasing the overall dimensions of the device. For example, in one embodiment, the device can be fabricated of multiple strands of material that are entwined or twisted around each other to form the body member 2 (for example, multiple strands of wire can be twisted around each other to form the body member). According to these particular embodiments, any number of individual strands can be utilized to form the body member, for example, 2, 3, 4, or more strands. The number of individual strands twisted to form the body member can be selected depending upon such factors as, for example, the desired diameter of the material forming the body member and/or the overall body member diameter, the desired flexibility or rigidity of the device during insertion and/or implantation, the size of the implantation, the desired incision size, the material used to form the body member, and the like.

In another embodiment, the surface area of the body member 2 can be increased by including surface configurations on the body member 2. According to these embodiments, any suitable type of surface configuration can be provided to the body member 2, such as, for example, dimples, pores, raised portions (such as ridges or grooves), indented portions, and the like. Surface configuration can be accomplished by roughening the surface of the material used to fabricate the body member 2. In one such embodiment, the surface of the body member is roughened using mechanical techniques (such as mechanical roughening utilizing such material as 50 μm silica), chemical techniques, etching techniques, or other known methods. In other embodiments, surface configuration can be accomplished by utilizing a porous material to fabricate the body member 2. Examples of porous material are described elsewhere herein. Alternatively, materials can be treated to provide pores in the material, utilizing methods well known in the art. In still further embodiments, surface configuration can be accomplished by fabricating the body member 2 of a machined material, for example, machined metal. The material can be machined to provide any suitable surface configuration as desired, including, for example, dimples, pockets, pores, and the like.

In still further embodiments, increased device surface area can be provided by utilizing a body member configured as a threaded shaft that is tapered or untapered, as desired. Such threaded shaft embodiments are similar to a typical wood screw. The threaded shaft can be fabricated using any suitable techniques, such as molding or machining the threads of the shaft. Further, the threading on the shaft can be a continuous spiral thread that runs continually from the proximal to the distal end of the body member, or the threading can be provided as noncontiguous rings about the body member. Although these particular embodiments can require a larger incision site for implantation of the device in a patient, in some applications, the increased surface area provided by the threaded shaft (discussed in more detail herein) can outweigh the larger incision required.

In preferred embodiments, surface configuration of the body member 2 can provide advantages, such as, for example, increased surface area of the body member for application of the polymeric coating composition, increased durability of the device, increased tenacity of the polymeric coating composition to the body member (for example, by virtue of a roughened surface, increased surface area for adherence, and the like), enhanced removability of the device after a desired treatment duration, and the like.

The body member 2 can include surface configurations along its entire length, or only a portion of the length of the body member, as desired.

As shown in FIG. 1, the body member 2 is preferably cylindrical in shape, with a circular cross-section. However, the cross-sectional shape of the body member 2 is not limited and, for example, can alternatively have square, rectangular, octagonal or other desired cross-sectional shapes.

As shown in FIGS. 1 and 3, a preferred embodiment can include a cap 8 positioned at the proximal end 4 of the body member 2. When included in the device, the cap 8 can assist in stabilizing the device once implanted in the body, thereby providing additional anchoring features of the device. Preferably, the device is inserted into the body through an incision until the cap 8 abuts the incision on the exterior of the body. If desired, the cap 8 can then be sutured to the body at the incision site to further stabilize and prevent the device from moving once it is implanted in its desired location. When the device is implanted in the eye, for example, the device can be inserted into the eye through an incision until the cap 8 abuts the incision. If desired, the cap 8 can then be sutured to the eye, to provide further stabilization as discussed above.

The overall size and shape of the cap 8 is not particularly limited, provided that irritation to the body at the incision site is limited. Preferably, the cap 8 is sized such that it provides a low profile. For example, the dimensions of the cap 8 are preferably selected to provide a small surface area to accomplish such desired features as additional anchoring characteristics of the device, without substantially increasing the overall profile of the device upon implantation. In some embodiments, for example, the cap can be covered by a flap of tissue at the incision site upon implantation, to further reduce potential irritation and/or movement of the device at the implantation and/or incision sites. One illustrative example described in more detail elsewhere herein is the covering of the cap with a scleral cap upon implantation of the device in the eye.

Further, while the cap 8 is illustrated with a circular shape, the cap can be of any shape, for example, circular, rectangular, triangular, square, and the like. In order to minimize irritation to the incision site, the cap preferably has rounded edges. The cap 8 is designed such that it remains outside the implantation site and, as such, the cap 8 is sized so that it will not pass into the implantation site through the incision through which the device is inserted.

As described herein, inclusion of a cap 8 in the device can provide additional anchoring features to the device itself. However, in some embodiments, it can be desirable to further secure the device to provide additional anchoring or securing features at the implantation site. Thus, when desired, the cap 8 can be further designed such that it can be easily sutured or otherwise secured to the surface surrounding the incision and can, for example, contain one or more holes (not shown) through which sutures can pass.

The materials used to fabricate the cap 8 are not particularly limited and include any of the materials previously described for fabrication of the body member 2. Preferably, the materials are insoluble in body fluids and tissues with which the device comes in contact. Further, it is preferred that the cap 8 is fabricated of a material that does not cause irritation to the portion of the body that it contacts (such as the area at and surrounding the incision site). For example, when the device is implanted into the eye, the cap 8 is preferably fabricated from a material that does not cause irritation to the portion of the eye that it contacts. As such, preferred materials for this particular embodiment include, by way of example, various polymers (such as silicone elastomers and rubbers, polyolefins, polyurethanes, acrylates, polycarbonates, polyamides, polyimides, polyesters, polysulfones, and the like), as well as metals (such as those described previously for the body member).

In some embodiments, the cap 8 can be fabricated from the same material as the body member 2. Alternatively, the cap 8 can be fabricated from a material that is different from the body member 2. The cap 8 can be fabricated separately from the body member 2, and subsequently attached to the body member 2, using any suitable attachment mechanism (such as, for example, suitable adhesives or soldering materials). For example, the cap 8 can be fabricated to include an aperture, into which the body member 2 is placed and thereafter soldered, welded, or otherwise attached. In alternative embodiments, the cap 8 and body member 2 are fabricated as a unitary piece, for example, utilizing a mold that includes both components (the body member 2 and cap 8) of the device. The precise method of fabricating the device can be chosen depending upon such factors as availability of materials and equipment for forming the components of the device.

In some embodiments, the cap 8 can be provided with a polymeric coating composition. According to these particular embodiments, the polymeric coating composition provided in connection with the cap 8 can be the same as, or different from, the polymeric coating composition provided in connection with the body member 2. For example, the particular bioactive agent included in the polymeric coating composition for the cap 8 can be varied to provide a desired therapeutic effect at the incision site. Exemplary bioactive agents that could be desirable at the incision site include antimicrobial agents, anti-inflammatory agents, and the like, to reduce or otherwise control reaction of the body at the incision site. It will be readily apparent upon review of this disclosure that the first polymer and second polymer can also be selected for the polymeric coating composition provided in connection with the cap 8, to provide a desired polymeric coating composition specific for the cap, when desired.

In some embodiments, the cap 8 can include a polymeric coated composition that is the same as the polymer coated composition provided in connection with the body member 2.

According to the invention, a polymeric coated composition is provided in contact with the body member of the device. The polymeric coated composition can comprise one or more polymers and a bioactive agent.

The coated composition is provided in contact with at least a portion of the body member of the device. In some embodiments, for example, it can be desirable to provide the coated composition in contact with the entire surface of the body member. Alternatively, the coated composition can be provided on a portion of the body member (such as, for example, an intermediate portion of the body member located between the proximal and distal ends thereof). In some preferred embodiments, for example, it can be desirable to provide the coated composition in contact with a portion of the body member that does not include a sharp distal tip of the body member. This can be desirable, for example, to reduce risk of delamination of the coated composition at the sharp tip and/or to maintain the sharpness of the tip. The amount of the body member that is in contact with the coated composition can be determined by considering such factors as the amount of bioactive agent to be provided at the implantation site, the choice of first polymer and/or second polymer for the coated composition, the characteristics of the implantation site, risk of delamination of the coated composition, and the like. For example, in some embodiments, it can be desirable to provide the coated composition on portions of the body member other than the proximal and distal ends of the device, so as to reduce risk of delamination upon implant and/or explant of the device. Optionally, such delamination can also be minimized, in some embodiments, by providing a stepped coating thickness, such that the coating thickness decreases towards the proximal and/or distal ends of the body member. In still further optional embodiments, the body member can be provided with a coated composition at its distal and/or proximal ends that differs from the composition of the coating at other portions of the body member. One example of such an embodiment includes a body member having a lubricious coating at the distal and/or proximal end of the body member, with a different coated composition in the intermediate portion of the body member that is located between the proximal and distal ends of the body member. Utilizing the concepts described herein, one of skill in the art can determine the amount of body member to be provided in contact with the coated composition, and/or the composition of coated composition provided at one or more distinct regions of the body member, as desired.

Suitable polymers and bioactive agents for use in preparing coating compositions in accordance with the invention can be prepared using conventional organic synthesis procedures and/or are commercially available from a variety of sources. Preferably, such polymers are either provided in a form suitable for in vivo use in a coating composition, or are purified for such use to a desired extent (for example, by removing impurities) by conventional methods available to those skilled in the art.

A coating composition can be prepared to include a solvent, one or more polymers dissolved in the solvent, and the bioactive agent or agents dispersed in the polymer/solvent mixture. The solvent is preferably one in which the one or more polymers form a true solution. The bioactive agent can either be soluble in the solvent or form a dispersion throughout the solvent. In some embodiments, the coating composition can provide a one-part system that can be applied to the device in one composition. For example, U.S. Pat. No. 6,214,901 exemplifies the use of tetrahydrofuran (THF) as a solvent. While THF is suitable, and at times preferred, for certain coating compositions, other solvents can be used in accordance with the invention as well, including, for example, alcohols (such as methanol, butanol, propanol, isopropanol, and the like), alkanes (such as halogenated or unhalogenated alkanes such as hexane and cyclohexane), amides (such as dimethylformamide), ethers (such as dioxolane), ketones (such as methylketone), aromatic compounds (such as toluene and xylene), acetonitrile, and esters (such as ethyl acetate).

The coated composition can be biocompatible, such that it results in no significant induction of inflammation or irritation when implanted in the body. In addition, the coated composition is preferably useful under a broad spectrum of both absolute concentrations and relative concentrations of the polymers. In the context of the previous sentence, the physical characteristics of the coated composition (such as tenacity, durability, flexibility and expandability) will typically be suitable over a broad range of polymer concentrations.

Turning to the polymeric coating composition itself, in an embodiment, the polymeric coating composition comprises one or more polymers and one or more bioactive agents. In an embodiment, the polymeric coating composition comprises a first polymer, a second polymer, and a bioactive agent. The first polymer can provide one or more desirable properties, such as compatibility with the second polymer and bioactive agent, hydrophobicity, durability, bioactive agent release characteristics, biocompatibility, molecular weight, and commercial availability. The first polymer can comprise polyalkyl (meth)acrylate, aromatic poly(meth)acrylate, or a combination of polyalkyl(meth)acrylate and aromatic poly(meth)acrylate, where "(meth)" will be understood by those skilled in the art to include such molecules in either the acrylic and/or methacrylic form (corresponding to the acrylates and/or methacrylates, respectively).

Examples of suitable first polymers include polyalkyl (meth)acrylates, and in particular, those with alkyl chain lengths from 2 to 8 carbons, and with molecular weights from 50 kilodaltons to 900 kilodaltons. An exemplary first polymer is poly(n-butyl methacrylate) (pBMA). Such polymers are available commercially, e.g., from Aldrich, with molecular weights ranging from about 200,000 daltons to about 320,000 daltons, and with varying inherent viscosity, solubility, and form (e.g., as crystals or powder).

As used herein "weight average molecular weight" or $M_w$, is an absolute method of measuring molecular weight and is particularly useful for measuring the molecular weight of a polymer preparation. The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\sum_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry*; pg 271 (1990).

Coating compositions including aromatic poly(meth)acrylates can provide unexpected advantages in certain embodiments. Such advantages relate, for instance, to the ability to provide coatings having different characteristics (such as different solubility characteristics) than other coatings (for example, those that include a polyalkyl(meth)acrylate polymer), while maintaining a desired combination of other properties. Without intending to be bound by a particular theory, it appears that the increased solubility (particularly in more polar solvents) that is provided by an aromatic, rather than an alkyl poly(meth)acrylate of this invention, permits the use of poly(ethylene-co-vinyl acetate) polymers that are themselves more polar (for example, having significantly greater vinyl acetate concentrations) than those typically preferred for use with the polyalkyl(meth)acrylates.

Examples of suitable aromatic poly(meth)acrylates include polyaryl(meth)acrylates, polyaralkyl(meth)acrylates, and polyaryloxyalkyl(meth)acrylates, in particular those with aryl groups having from six to sixteen carbon atoms and with weight average molecular weights in the range of about 50 kD to about 900 kD. Preferred aromatic poly(meth)acrylates include those compounds wherein at least one carbon chain and at least one aromatic ring are combined with acrylic groups (typically esters). For example, a polyaralkyl (meth)acrylate or polyarylalkyl(meth)acrylate can be made from aromatic esters derived from alcohols also containing aromatic moieties.

Examples of polyaryl(meth)acrylates include poly-9-anthracenylmethacrylate, polychlorophenylacrylate, polymethacryloxy-2-hydroxybenzophenone, polymethacryloxybenzotriazole, polynaphthylacrylate, polynapthylmethacrylate, poly-4-nitrophenylacrylate, polypentachloroacrylate, polypentabromoacrylate, polypentafluoroacrylate, polypentachloromethacrylate, polypentabromomethacrylate, polypentafluoromethacrylate, polyphenylacrylate, and polyphenylmethacrylate.

Examples of polyaralkyl(meth)acrylates include polybenzylacrylate, polybenzylmethacrylate, poly-2-phenethylacrylate, poly-2-phenethylmethacrylate, and poly-1-pyrenylmethylmethacrylate.

Examples of polyaryloxyalkyl(meth)acrylates include polyphenoxyethylacrylate, polyphenoxyethylmethacrylate, and polyethyleneglycolphenylether acrylates and polyethyleneglycolphenylether methacrylates with varying polyethyleneglycol molecular weights.

The polymeric coating composition can include a second polymer providing one or more desirable properties, such as compatibility with the first polymer and bioactive agent, hydrophobicity, durability, bioactive agent release characteristics, biocompatibility, molecular weight, and commercial availability, particularly when used in admixture with the first polymer.

Examples of suitable second polymers are commercially available and include poly(ethylene-co-vinyl acetate) having vinyl acetate concentrations in the range of about 10% to about 90% by weight of the pEVA copolymer, or in the range of about 20% to about 60% by weight of the pEVA copolymer, or in the range of about 30% to about 34% by weight of the pEVA copolymer. Poly(ethylene-co-vinyl acetate) co-polymers having lower percent vinyl acetate can become increasingly insoluble in typical solvents, such as THF, toluene, and the like. The second polymer can be obtained commercially in the form of beads, pellets, granules, and the like.

In an embodiment, the polymer composition includes a first polymer with a weight average molecular weight in the range of about 100 kD to about 500 kD, and a pEVA copolymer with a vinyl acetate content in the range of about 10% to about 90% by weight, and more preferably in the range of about 20% to about 60% by weight. In a particularly preferred embodiment, the polymer composition includes a first polymer with a weight average molecular weight in the range of about 200 kD to about 500 kD, and a pEVA copolymer with a vinyl acetate content in the range of about 30% to about 34% by weight.

In an embodiment, the coating composition in accordance with the invention comprises polyalkyl(meth)acrylates (for example, poly(n-butyl)methacrylate) or aromatic poly(meth) acrylates (for example, polybenzyl(meth)acrylates) and poly (ethylene-co-vinyl acetate) copolymers. This particular composition can be used with absolute polymer concentrations (as defined herein) in the range of about 0.05% to about 70% by weight of the total coating composition.

In an embodiment, the polymeric coating composition comprises poly(n-butyl)methacrylate ("pBMA") and poly (ethylene-co-vinyl acetate) as the second polymer ("pEVA"). This composition has proven useful with absolute polymer concentrations in the range of about 0.05% to about 70% by weight of the coating composition. As used herein "absolute polymer concentration" refers to the total combined concentration(s) of polymer(s) in the coating composition. In an embodiment, the coating composition comprises polyalkyl (meth)acrylate (such as poly(n-butyl)methacrylate with a weight average molecular weight in the range of about 100 kilodaltons (kD) to about 1000 kD and a pEVA copolymer with a vinyl acetate content in the range of about 10% to about 90% by weight of the pEVA copolymer. In an embodiment, the polymer composition comprises polyalkyl(meth)acrylate (such as poly(n-butyl)methacrylate) with a molecular weight in the range of about 200 kD to about 500 kD and a pEVA copolymer with a vinyl acetate content in the range of about 30% to about 34% by weight. The concentration of the bioactive agent in the polymeric coating composition of this embodiment can be in the range of about 0.01% to about 90% by weight, based upon the weight of the final coating composition.

Second polymers of the invention can also comprise one or more polymers selected from the group consisting of (i) polyalkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers.

Polyalkylene-co-alkyl(meth)acrylates include those copolymers in which the alkyl groups are either linear or branched, and substituted or unsubstituted with non-interfering groups or atoms. Such alkyl groups preferably comprise from 1 to 8 carbon atoms, inclusive, and more preferably, from 1 to 4 carbon atoms, inclusive. In an embodiment, the alkyl group is methyl. In some embodiments, copolymers that include such alkyl groups can comprise from about 15% to about 80% (wt.) of alkyl acrylate. When the alkyl group is methyl, the polymer contains from about 20% to about 40% (wt.) methyl acrylate in some embodiments, and from about 25 to about 30% (wt.) methyl acrylate in a particular embodiment. When the alkyl group is ethyl, the polymer contains from about 15% to about 40% (wt.) ethyl acrylate in an embodiment, and when the alkyl group is butyl, the polymer contains from about 20% to about 40% (wt.) butyl acrylate in an embodiment.

Alternatively, second polymers for use in this invention can comprise ethylene copolymers with other alkylenes, which in turn, can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), poly(ethylene-co-1-butene-co-1-hexene) and/or poly(ethylene-co-1-octene).

"Polybutenes" suitable for use in the present invention includes polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative second polymers include diolefin-derived, non-aromatic polymers and copolymers, including those in which the diolefin monomer used to prepare the polymer or copolymer is selected from butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, trans- and/or 1,2- monomer units, or from a mixture of all three monomers, and polyisoprenes prepared by the polymerization of cis-1,4- and/or trans-1,4- monomer units. Alternatively, the polymer is a copolymer, including graft copolymers, and random copolymers based on a non-aromatic mono-olefin monomer such as acrylonitrile, and an alkyl(meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a Mw between about 150 kilodaltons and about 1,000 kilodaltons. In an embodiment, polymers and copolymers have a Mw between about 200 kilodaltons and about 600 kilodaltons.

Additional alternative second polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl(meth)acrylate (e.g., methyl methacrylate) and/or butene. Useful block copolymers include copolymer containing (a) blocks of polystyrene, (b) blocks of an polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative second polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have an Mw from about 100 kilodaltons to about 300 kilodaltons.

Polymers of the invention can also include a poly(ether ester) multiblock copolymer based on poly(ethylene glycol) (PEG) and poly(butylene terephthalate) and can be described by the following general structure:

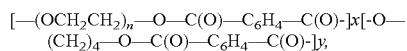

where —$C_6H_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. Preferably, n is selected such that the molecular weight of the PEG block is between about 300 and about 4000. Preferably, x and y are selected so that the multiblock copolymer contains from about 55% up to about 80% PEG by weight.

The block copolymer can be engineered to provide a wide array of physical characteristics (e.g., hydrophilicity, adherence, strength, malleability, degradability, durability, flexibility) and active agent release characteristics (e.g., through controlled polymer degradation and swelling) by varying the values of n, x and y in the copolymer structure. Degradation of the copolymer does not create toxic degradation products or an acid environment, and its hydrophilic nature conserves the stability of labile active agents, such as proteins (e.g., lysozymes). Microspheres containing mixtures of block copolymers and active agents can easily be designed for use in situations requiring faster degradation.

In an embodiment, polymers of the present invention include microspheres based on dextran microspheres cross-linked through ester linkages. The microspheres are produced using a solvent-free process, thus avoiding the possibility of denaturing incorporated protein molecules. Loading levels as high as 15% (wt) protein can be achieved along with high encapsulation efficiencies (typically greater than 90%). Microsphere sizes of less than 50 um are possible, allowing for subcutaneous injection. The microsphere particles degrade through bulk erosion rather than surface erosion. No acidification occurs upon degradation, thus preserving the structural integrity of the protein molecules.

Polymers of the invention also include biodegradable polymers. Suitable biodegradable polymeric materials are selected from: (a) non-peptide polyamino polymers; (b) polyiminocarbonates; (c) amino acid-derived polycarbonates and polyarylates; and (d) poly(alkylene oxide) polymers. The biodegradable polymeric materials can break down to form degradation products that are non-toxic and do not cause a significant adverse reaction from the body.

In an embodiment, the biodegradable polymeric material is composed of a non-peptide polyamino acid polymer. Suitable non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, comprising two or three amino acid units having one of the following two structures illustrated below:

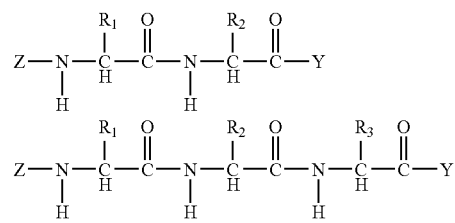

wherein the monomer units are joined via hydrolytically labile bonds at not less than one of the side groups $R_1$, $R_2$, and $R_3$, and where $R_1$, $R_2$, $R_3$ are the side chains of naturally occurring amino acids; Z is any desirable amine protecting group or hydrogen; and Y is any desirable carboxyl protecting group or hydroxyl. Each monomer unit comprises naturally occurring amino acids that are then polymerized as monomer units via linkages other than by the amide or "peptide" bond. The monomer units can be composed of two or three amino acids united through a peptide bond and thus comprise dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are non-toxic, are biodegradable, and can provide zero-order release kinetics for the delivery of active agents in a variety of therapeutic applications. According to these aspects, the amino acids are selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, omithine, lanthionine, hypoglycin A, β-alanine, γ-amino butyric acid, alpha aminoadipic acid, canavanine, venkolic acid, thiolhistidine, ergothionine, dihydroxyphenylalanine, and other amino acids well recognized and characterized in protein chemistry.

In an embodiment, the biodegradable polymeric material can be composed of polyiminocarbonates. Polyiminocarbonates are structurally related to polycarbonates, wherein imino groups (>C=NH) are present in the places normally occupied by carbonyl oxygen in the polycarbonates. Thus, the biodegradable component can be formed of polyiminocarbonates having linkages

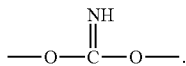

For example, one useful polyiminocarbonate has the general polymer structural formula

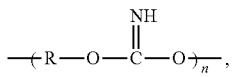

wherein R is an organic divalent group containing a non-fused aromatic organic ring, and n is greater than 1. Preferred embodiments of the R group within the general formula above is exemplified by, but is not limited to the following:
R group

(a)

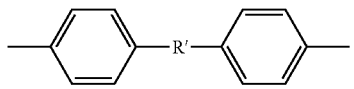
(b)

wherein R' is lower alkene $C_1$ to $C_6$

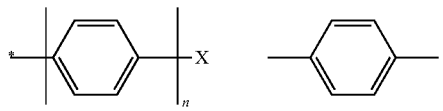
(c)

wherein n is an integer equal to or greater than 1, X is a hetero atom such as —O—, —S—, or a bridging group such as —NH—, —S(=O)—, —SO$_2$—, —C(=O)—, —C(CH$_3$)$_2$—, —CH(CH$_3$)—, —CH(CH$_3$)—CH$_2$—CH(CH$_3$)—,

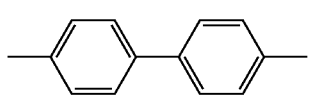
(d)

Also, compounds of the general formula

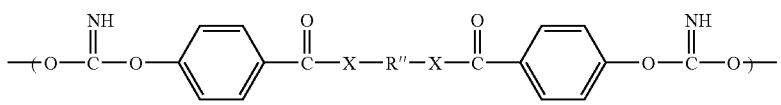

can be utilized, wherein X is O, NH, or NR''', wherein R''' is a lower alkyl radical; and R'' is a divalent residue of a hydrocarbon including polymers such as a polyolefin, an oligoglycol or polyglycol such as polyalkylene glycol ether, a polyester, a polyurea, a polyamine, a polyurethane, or a polyamide. Exemplary starting material for use in accordance with these embodiments include diphenol compounds having the formula

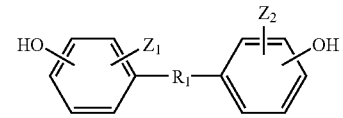

and dicyanate compounds having the formula

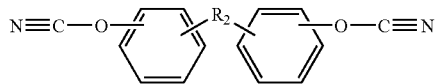

with $R_1$ and $R_2$ being the same or different and being alkylene, arylene, alkylarylene or a functional group containing heteroatoms. $Z_1$, and $Z_2$ can each represent one or more of the same or different radicals selected from the group consisting of hydrogen, halogen, lower-alkyl, carboxyl, amino, nitro, thioether, sulfoxide, and sulfonyl. Preferably, each of $Z_1$ and $Z_2$ are hydrogen.

In an embodiment, the biodegradable polymeric material can be composed of various types of amino acid-derived polycarbonates and polyarylates. These amino acid-derived polycarbonates and polyarylates can be prepared by reacting certain amino acid-derived diphenol starting materials with either phosgene or dicarboxylic acids, respectively. Exemplary amino acid-derived diphenol starting materials for the preparation of the amino acid-derived polycarbonates and/or polyarylates of this embodiment are monomers that are capable of being polymerized to form polyiminocarbonates with glass transition temperatures ("Tg's") sufficiently low to permit thermal processing. The monomers according to this embodiment are diphenol compounds that are amino acid ester derivatives having the formula shown below:

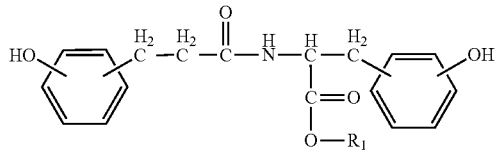

in which $R_1$ is an alkyl group containing up to 18 carbon atoms.

In yet another embodiment, the biodegradable polymeric material can be composed of copolymers containing both hydrophilic poly(alkylene oxides) (PAO) and biodegradable sequences, wherein the hydrocarbon portion of each PAO unit contains from 1 to 4 carbon atoms, or 2 carbon atoms (i.e., the PAO is poly(ethylene oxide)). For example, useful biodegradable polymeric materials can be made of block copolymers containing PAO and amino acids or peptide sequences and contain one or more recurring structural units independently represented by the structure -L-$R_1$-L-$R_2$—, wherein $R_1$ is a poly(alkylene oxide), L is —O— or —NH—, and $R_2$ is an amino acid or peptide sequence containing two carboxylic acid groups and at least one pendent amino group. Other useful biodegradable polymeric materials are composed of polyarylate or polycarbonate random block copolymers that include tyrosine-derived diphenol monomers and poly(alkylene oxide), such as the polycarbonate shown below:

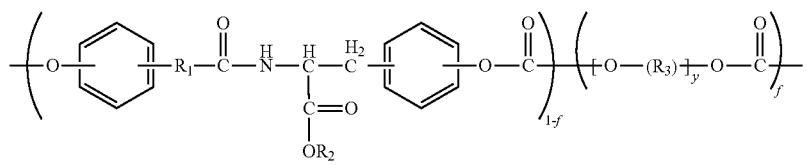

wherein $R_1$ is —CH=CH— or (—$CH_2$—)$_j$, in which j is 0 to 8; $R_2$ is selected from straight and branched alkyl and alkylaryl groups containing up to 18 carbon atoms and optionally containing at least one ether linkage, and derivatives of biologically and pharmaceutically active compounds covalently bonded to the copolymer; each $R_3$ is independently selected from alkylene groups containing 1 to 4 carbon atoms; y is between 5 and about 3000; and f is the percent molar fraction of alkylene oxide in the copolymer and ranges from about 0.01 to about 0.99.

In some embodiments, pendent carboxylic acid groups can be incorporated within the polymer bulk for polycarbonates, polyarylates, and/or poly(alkylene oxide) block copolymers thereof, to further control the rate of polymer backbone degradation and resorption.

The coating material can also include natural polymers such as polysaccharides such as polydextrans, glycosaminoglycans such as hyaluronic acid, and polypeptides or soluble proteins such as albumin and avidin, and combinations thereof. Combinations of natural and synthetic polymers can also be used. The synthetic and natural polymers and copolymers as described can also be derivitized with a reactive group, for example, a thermally reactive group or a photoreactive group.

In preferred embodiments, the coating composition comprises a bioactive agent. For purposes of the description herein, reference will be made to "bioactive agent," but it is understood that the use of the singular term does not limit the application of bioactive agents contemplated, and any number of bioactive agents can be provided using the teaching herein. As used herein, "bioactive agent" refers to an agent that affects physiology of biological tissue. Bioactive agents useful according to the invention include virtually any substance that possess desirable therapeutic characteristics for application to the implantation site.

Exemplary bioactive agents include, but are not limited to, thrombin inhibitors; antithrombogenic agents; thrombolytic agents; fibrinolytic agents; vasospasm inhibitors; calcium channel blockers; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 13-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); mydriatics (such as atropinsurface, cyclopentolate, homatropine, scopolamine, tropicamide, eucatropine, hydroxyamphetamine); sympathomimetics (such as epinephrine); antineoplastics (such as carmustine, cisplatin, fluorouracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); beta adrenergic blockers (such as timolol maleate, levobunolol HCl, betaxolol HCl); immunosuppressive agents (such as rapamycin, cyclosporin, tacrolimus, pimecrolimus, etc.), growth hormone antagonists, growth factors (such as epidermal growth factor, fibroblast growth factor, platelet derived growth factor, transforming growth factor beta, somatotropin, fibronectin); carbonic anhydrase inhibitors (such as dichlorophenamide, acetazolamide, methazolamide); inhibitors of angiogenesis (such as angiostatin, anecortave acetate, thrombospondin, anti-VEGF antibody); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and the like.

The particular bioactive agent, or combination of bioactive agents, can be selected depending upon one or more of the following factors: the application of the controlled delivery device, the medical condition to be treated, the anticipated duration of treatment, characteristics of the implantation site, the number and type of bioactive agents to be utilized, and the like.

The concentration of the bioactive agent in the coating composition can be provided in the range of about 0.01% to about 90% by weight, based on the weight of the final coating composition. Preferably, the bioactive agent is present in the coating composition in an amount in the range of about 75% by weight or less, preferably about 50% by weight or less. The amount of bioactive agent in the coating composition can be in the range of about 1 µg to about 10 mg, or about 100 µg to about 1500 µg, or about 300 µg to about 1000 µg.

Application of a coating composition with a lower percentage by weight of solvents can offer advantages. For example, using less solvent results in less evaporative cooling which can negatively affect the resulting coated composition. Using less solvent also results in less solvent evaporating into the air and less waste and less exposure for operators of the coating equipment. In an embodiment of the invention, the coating composition contains at least about 10 mg/ml total solids. In an embodiment, the coating composition contains at least about 40 mg/ml.

In some embodiments, the coating composition contains less than about 100 mg/ml total solids. In an embodiment, the coating composition contains less than about 80 mg/ml total solids. The coating composition can contain from about 10 mg/ml to about 100 mg/ml total solids. The coating composition can also contain from about 40 mg/ml to about 80 mg/ml total solids. In an embodiment, the coating composition contains from about 50 mg/ml to about 60 mg/ml total solids. In an embodiment, the coating composition contains about 60 mg/ml total solids.

In some embodiments, the coated composition comprises at least two layers, wherein each layer comprises the same or different coated compositions. In one such embodiment, a first layer having either bioactive agent alone, or bioactive agent(s) together with one or more of the polymers (first polymer and/or second polymer) is applied, after which one or more additional layers are applied, each with or without bioactive agent. These different layers, in turn, can cooperate in the resultant composite coating to provide an overall release profile having certain desired characteristics, and is particularly preferred for use with bioactive agents having high molecular weight. According to the invention, the composition of individual layers of the coating can include any one or more of the following: one or more bioactive agents, and one or more polymers, as desired.

In some embodiments, the coated composition can be subsequently dried by evaporation of the solvent. The drying process can be performed at any suitable temperature, (for example, room temperature or elevated temperature), and optionally with the assistance of vacuum.

In some embodiments, the coating composition is applied to the body member under conditions of controlled relative humidity. As used herein, "relative humidity" is the ratio of the water vapor pressure (or water vapor content) to the saturation vapor pressure (or the maximum vapor content) at a given temperature of the air. The saturation vapor pressure in the air varies with air temperature: the higher the temperature, the more water vapor it can hold. When saturated, the relative humidity in the air is 100% relative humidity. According to some embodiments of the invention, the coating composition can be applied to the body member under conditions of increased or decreased relative humidity as compared to ambient humidity.

According to the invention, humidity can be controlled in any suitable manner, including at the time of preparing and/or applying the coating composition to the body member. For example, when humidity is controlled at the time of preparing the coating composition, the water content of the coating composition can be adjusted, before and/or after the coating composition is applied to the body member. When humidity is controlled at the time of applying the coating composition, the coating composition can be applied to the body member in a confined chamber or area adapted to provide a relative humidity that differs from ambient humidity. Generally, it has been found that applying coating compositions under conditions of increased humidity will typically accelerate release of the bioactive agent, while applying coating compositions under conditions of decreasing humidity levels will tend to decelerate release of the bioactive agent. As contemplated in the invention, even ambient humidity can be considered "controlled" humidity if it has been correlated with and determined to provide a corresponding controlled release of the bioactive agent.

Moreover, and particularly when coating a plurality of coating compositions onto the body member of the controlled delivery device to provide the final coated composition, humidity can be controlled in different ways (for example, using a controlled environment as compared to adjusting the water content of the coating composition) and/or at different levels to provide a desired release profile for the resulting coated composition. As described previously, a coated composition can be provided using a plurality of individual steps or layers of coating composition, including, for instance, an initial layer having only bioactive agent (or bioactive agent with one or both polymers), over which is coated one or more additional layers containing suitable combinations of bioactive agent, first polymer, and/or second polymer, the combined result of which is to provide a coated composition of the invention.

Thus, in preferred embodiments, the invention provides the ability to reproducibly control the release of a bioactive agent from a controlled delivery device.

In some embodiments, a plurality of coating compositions and corresponding coating steps can be employed, each with its own controlled humidity (when desired), in order to provide a desired combination of layers, each with its corresponding release profile. Those skilled in the art will appreciate the manner in which the combined effect of these various layers can be used and optimized to achieve various effects in vivo.

In yet another embodiment, the desired release rate of the bioactive agent from the coated composition can be selected by applying the coating composition to surfaces at a plurality of different humidity levels, and evaluating the corresponding release profiles to determine a controlled humidity level corresponding to a desired profile. In one such embodiment, for instance, the coating composition is applied to the device under relative humidity controlled at a level in the range of about 0% to about 95% relative humidity (at a given temperature, in the range of about 15° C. to about 30° C.), and more preferably in the range of about 0% to about 50% relative humidity. Without intending to be bound by a particular theory, it has been found that potential differences in the ambient humidity, as between coating runs at the same location, and/or as between different coating locations, can vary significantly, and in a manner that might affect such properties as the release of the bioactive agent. By using a controlled humidity, the invention can provide a coated composition that displays significantly more controllable and reproducible release characteristics.

The coating composition of the invention can be provided in any suitable form, for example, in the form of a true solution, or fluid or paste-like emulsion, mixture, dispersion, or blend. In turn, the coated composition will generally result from the removal of solvents or other volatile components and/or other physical-chemical actions (for example, heating or illumination) affecting the coated composition in situ upon the controlled delivery device surface.

The weight of the coated composition attributable to the bioactive agent can be in the range of about 1 µg to about 10 mg of bioactive agent per $cm^2$ of the surface area of the controlled delivery device. In some embodiments, the surface area can comprise all or a portion of the body member 2 of the device. In alternative embodiments, the surface area can comprise the body member 2 and the cap 8 of the device. Preferably, the weight of the coated composition attributable to the bioactive agent is in the range of about 0.01 mg to about 10 mg of bioactive agent per $cm^2$ of the surface area of the controlled delivery device. This quantity of bioactive agent is generally effective to provide adequate therapeutic effect under physiological conditions. As used herein, the surface area is the macroscopic surface area of the device.

In preferred embodiments, the final coating thickness of the coated composition on the controlled delivery device will typically be in the range of about 0.1 µm to about 100 µm, or in the range of about 5 µm to about 60 µm. The final coating thickness can be varied, and at times be outside the preferred ranges identified herein, depending upon such factors as the total amount of bioactive agent to be included in the coated composition, the type of bioactive agent, the number of bioactive agents to be included, the treatment course, the implantation site, and the like.

Thickness of the coated composition on the controlled delivery device can be assessed using any suitable techniques. For example, portions of the coated composition can be delaminated by freezing the coated controlled delivery device, for example, utilizing liquid nitrogen. The thickness at the edge of a delaminated portion can then be measured by optical microscopy. Other visualization techniques known in the art can also be utilized, such as microscopy techniques suitable for visualization of coatings having the thickness described herein of the invention.

In preferred embodiments, the controlled delivery device is sterilized utilizing common sterilization techniques, prior to implantation into the body. Sterilization can be accomplished, for example, utilizing ethylene oxide or gamma sterilization, as desired. In preferred embodiments, sterilization techniques utilized do not affect the polymeric coated composition (for example, by affecting release of the bioactive agent, stability of the coating, and the like).

According to the invention, the controlled delivery device preferably provides the ability to deliver one or more bioactive agents in a controlled release manner. As used herein, "controlled release" refers to release of a compound (for example, a bioactive agent) into a patient's body at a desired dosage (including dosage rate and total dosage) and duration of treatment. For example, the particular composition of the coating composition (including the amounts and ratios of the individual components of the coating composition) can be modified to achieve a desired release profile (amount of bioactive agent released from the coating composition per unit time) of the bioactive agent. While not intending to be bound by one particular theory, the release kinetics of the bioactive agent in vivo are thought to generally include both a short term ("burst") release component, within the order of minutes to hours or less after implantation of the device, and a longer term release component, which can range from on the order of hours to days or even months of useful release. As used herein, the acceleration or deceleration of bioactive agent release can include either or both of these release kinetics components.

The desired release profile of the bioactive agent can depend upon such factors as the particular bioactive agent selected, the number of individual bioactive agents to be provided to the implantation site, the therapeutic effect to be achieved, the duration of the implant in the body, and other factors known to those skilled in the art.

The ability to provide controlled release of a bioactive agent at an implantation site can provide many advantages. For example, the controlled delivery device can be maintained at an implantation site for any desired amount of time, and the release kinetics of the bioactive agent can be adjusted to deliver the total amount of bioactive agent, at the desired rate, to achieve a desired therapeutic effect. In some embodiments, the ability to provide controlled release of bioactive agent at the implantation site allows implantation of only one device, which can be maintained in place until the desired therapeutic effect is achieved, without need to remove the device and replace the device with a new supply of bioactive agent. Preferably, some embodiments of the invention avoid the need to refill a reservoir of bioactive agent at the implantation site. In some embodiments, the controlled delivery device can avoid the need for systemic application of bioactive agents, which can harm other tissues of the body.

The controlled delivery device can be utilized to deliver any desired bioactive agent or combination of bioactive agents to the eye, such as the bioactive agents described herein. The amount of bioactive agent(s) delivered over time is preferably within the therapeutic level, and below the toxic level. For example, a preferred target dosage for triamcinolone acetonide for use in treating diseases or disorders of the eye is preferably in the range of about 0.5 µg/day to about 2 µg per day. Preferably, the treatment course is greater than 6 months, more preferably greater than one year. Thus, in preferred embodiments, the bioactive agent is released from the coated composition in a therapeutically effective amount for a period of 6 months or more, or 9 months or more, or 12 months or more, or 36 months or more, when implanted in a patient.

Preferred embodiments of the invention provide a controlled delivery device that can release bioactive agent at a constant rate over extended periods of time. Moreover, the controlled delivery device preferably provides the ability to control the rate of release of bioactive agent by altering the formulation of the coating composition (for example, by providing the first polymer and second polymer in different relative amounts, and/or by altering the amount of bioactive agent included in the coating composition). As illustrated in the Examples, preferred coated compositions can provide release of a bioactive agent in a reproducible manner, for varying time periods, over a range of release rates. In the Examples, coating compositions having varying amounts of poly(ethylene-co-vinyl acetate) relative to the amount of poly (n-butyl)methacrylate, and a constant amount of a bioactive agent, were prepared and coated onto stainless steel substrates. The release rates of bioactive agent from the coated composition were determined in PBS utilizing the Elution Assay described herein. Results illustrated that the bioactive agent could be released from the coated composition for surprisingly long periods of time in vitro. Moreover, the coating compositions could be formulated to provide substantially linear release rates. Based upon the observed release rates in vitro, it is expected that in vivo release rates will be higher than those in PBS. See Jaffe et al., supra. Differences in release rates were observed among the coated compositions, which relate to differences in polymer composition of the coated compositions. Thus, in preferred embodiments, the polymer composition of the coating compositions can be manipulated to control the release rate of the bioactive agent.

Figure 6:
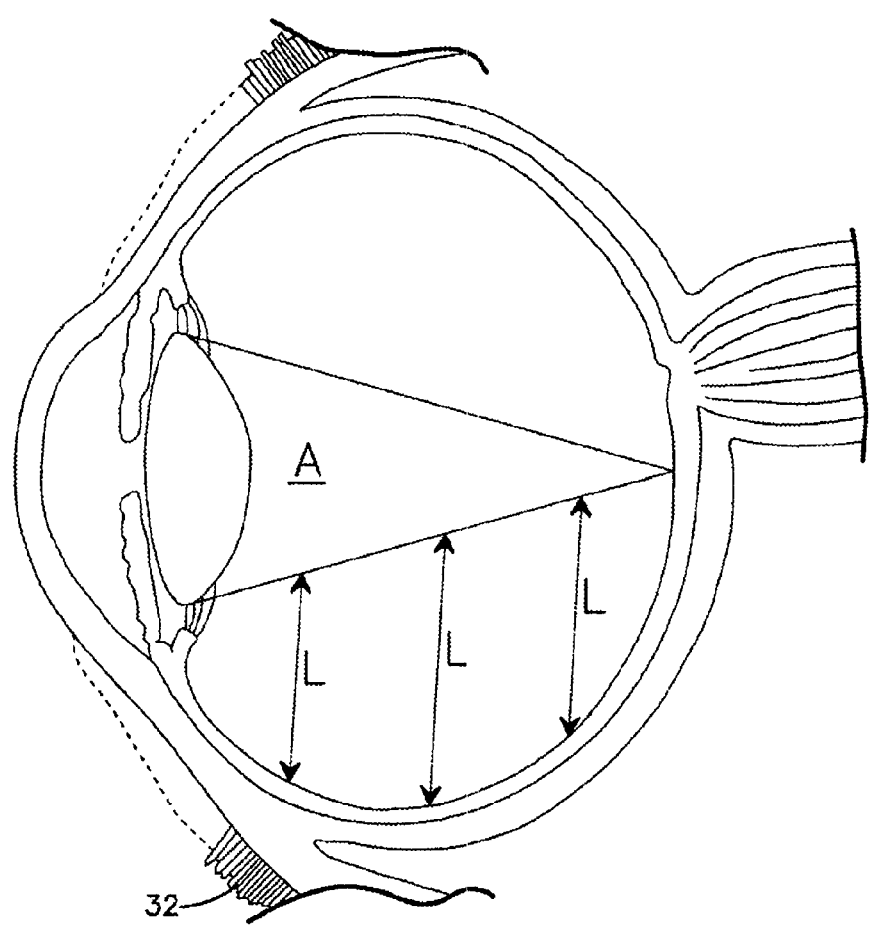
FIG. 6 is a cross-sectional view of an eye illustrating the central visual field "A" of the eye.

Use of the controlled delivery device can be further understood from the following discussion relating to a method for controlled release of a bioactive agent to the eye and with reference to FIGS. 5 and 6. However, it will be understood that the principles described below can be applied to any implantation site within a patient's body.

In accordance with the invention, the controlled delivery device is fabricated, utilizing the teaching herein, in preparation for the surgical procedure. An incision in the body is made to provide access to the implantation site. For example, when used to deliver bioactive agent to the eye, a sclerotomy is created for insertion of the controlled delivery device. Conventional techniques can be used for the creation of the sclerotomy. Such techniques include the dissection of the conjunctiva 32 and the creation of pars plana scleral incisions through the sclera 28. As shown in FIGS. 5 and 6, the dissection of the conjunctiva 32 typically involves pulling back the conjunctiva 32 about the eye so as to expose large areas of the sclera 28, and the clipping or securing of the conjunctiva 32 in that pulled back state (the normal position of the conjunctiva is shown in phantom). In other words, the sclera 28 is exposed only in the areas where the pars plana scleral incisions are to be made. Surgical instruments used in the procedure are then passed through these incisions. Thus, the incisions should be made large enough to accommodate the instruments required for the procedure.

Alternatively, the creation of the sclerotomy can be accomplished by use of an alignment device and method, such as that described in U.S. patent application Ser. No. 09/523,767, that enables sutureless surgical methods and devices thereof. In particular, such methods and devices do not require the use of sutures to seal the openings through which instruments are inserted. The alignment devices are inserted through the conjunctiva and sclera to form one or more entry apertures. Preferably, the alignment devices are metal or polyimide cannulas through which the surgical instruments used in the procedure are inserted into the eye.

In further embodiments, the device can be implanted directly through a self-starting transconjunctival trans-scleral "needle stick." For example, the body member 2 of the device can include a sharp tip 10, such as that illustrated in FIG. 3. According to this embodiment, the sharp tip 10 can be utilized to pierce the body and thereby create the incision site and access to the implantation site. In this case, no conjunctival surgery or extraneous alignment device is necessary.

In further embodiments, the conjunctival tissue can be dissected to expose a portion of the pars plana region, and a needlestick can be made into the sclera in the exposed region. A self-starting coil that includes a sharp tip is then inserted through the pars plana at the site of the needlestick, and the coil is rotated through the sclera until the cap of the device abuts the sclera. In some preferred embodiments, the needlestick is smaller than the diameter of the body member of the implantable device (for example, a 30-gauge needlestick can be used with an implantable device having a body member with a diameter of 0.5 mm or less). The conjunctival tissue is then pulled over the cap, to provide a flap or "seal" over the device, thus minimizing irritation of the implantation site, foreign body sensation, and the like. Optionally, the conjunctival tissue can be further secured by a single suture (in preferred embodiments, a biodegradable suture).

In some embodiments, it can be preferable to create an incision site that is slightly larger than the dimensions of the proximal portion of the body member. For example, when the device includes a cap 8 and is implanted into the eye, it can be preferable to create an incision that is larger than the largest diameter of the cap 8, such that the cap sits below the outer surface of the sclera. For example, a partial incision in the sclera can be made to create a scleral flap. Once the device has been implanted, and the cap 8 is placed so that it abuts the incision site, the scleral flap can be folded back over the device, thus providing a covering over the cap. Alternatively, when the proximal end of the body member does not include a cap 8, a flap-like cover can still be utilized to cover the proximal end of the device, in accordance with the description above. Preferably, these embodiments minimize the contact of the proximal end (for example, the cap 8) of the device with other body tissues, thereby reducing such risks as irritation of body tissues, and/or translation of movement of the eye to the device, thereby potentially damaging eye tissues. This can provide one or more advantages, such as reduced tendency for movement of the eye to be translated to the controlled delivery device, since the proximal end of the device will not be sitting at the surface of the eye and thus in contact with other body tissues; and reduced irritation of surrounding tissues.

The body member 2 is then inserted into the eye. For example, in embodiments wherein the body member 2 has a coil shape, the body member 2 is inserted into the eye by rotating or twisting the body member 2 into the eye until the cap 8 abuts the outer surface of the eye. In embodiments wherein the body member 2 is fabricated of a shape memory material, the shape memory material is first cooled to a temperature at which the martensite phase is stable and the device is deformed, for example, into a linear shape. The device is then inserted into the eye. To return the device to its memory shape, the device is left unrestrained and is simply allowed to reach a temperature (for example, by heating the device) above the martensite phase temperature. For example, the shape memory material can be heated by a laser to return the device to a temperature above the martensite phase temperature. The shape memory material can also be selected such that the martensite phase temperature is below body temperature so that the material is simply cooled to below body temperature, deformed to a linear shape, and inserted into the eye. Then, as the material warms up within the eye to body temperature, the device can return to its remembered shape. As discussed herein, when laser application is utilized, conditions are preferably controlled to maintain such parameters as wavelength and temperature, to minimize adverse effect on the polymeric coated composition.

FIG. 5 illustrates a controlled delivery device according to one embodiment of the invention that is implanted in the eye. When implanted into the eye, it is desirable to limit the length L of controlled delivery devices to prevent the controlled delivery device from entering the central visual field A (see FIG. 6). If the implant enters the central visual field A, this can result in blind spots in the patient's vision and can increase the risk of damage to the retinal tissue and lens capsule. Thus, for example, when the controlled delivery device is inserted at the pars plana (as shown in FIG. 5), the distance from the implantation site on the pars plana to the central visual field A is preferably less than about 1 cm.

Optionally, after the device is implanted into the eye, the cap 8 can then be sutured or otherwise secured to the sclera to maintain the controlled delivery device in place. In preferred embodiments, no further manipulation of the device is required for delivery of one or more bioactive agents to the interior of the eye. The conjunctiva can be adjusted to cover the cap 8 of the device, when desired, and the surgical procedure is completed.

In other embodiments, when a lumen is included in the device for delivery of one or more additional substances to the interior of the eye, further steps can be included as follows. If a cover is used to close the port(s), it is removed at this time, and if used, a collar for providing a snug fit about the injection mechanism (such as a syringe) is provided. The injection mechanism is then connected with the port(s) for injection of one or more substances to the controlled delivery device. If the port(s) are composed of an self-sealing material through which the needle of an injection mechanism can be inserted and which seals off automatically when the injection mechanism is removed, the injection mechanism is simply inserted through the port and the substance injected. Following injection, the conjunctiva can be adjusted to cover the cap 8 of the device, if desired.

The controlled delivery device of the invention can be used to deliver one or more bioactive agents to the eye for the treatment of a variety of ocular conditions such as, for example, retinal detachment; occlusions; proliferative retinopathy; proliferative vitreoretinopathy; diabetic retinopathy; inflammations such as uveitis, choroiditis, and retinitis; degenerative disease (such as age-related macular degeneration, also referred to as AMD); vascular diseases; and various tumors including neoplasms. In yet further embodiments, the controlled delivery device can be used post-operatively, for example, as a treatment to reduce or avoid potential complications that can arise from ocular surgery. In one such embodiment, the controlled delivery device can be provided to a patient after cataract surgical procedures, to assist in managing (for example, reducing or avoiding) post-operative inflammation.

In some applications, additives can further be included with the bioactive agent and/or additional substance to be delivered to the implantation site. Examples of suitable additives include, but are not limited to, water, saline, dextrose, carriers, preservatives, stabilizing agents, wetting agents, emulsifying agents, excipients, and the like.

Once the bioactive agent has been delivered to the implantation site, the controlled delivery device can be removed if the required therapeutically effective amount of bioactive agent has been delivered for treatment of the condition.

Coating Configurations

Figure 7:
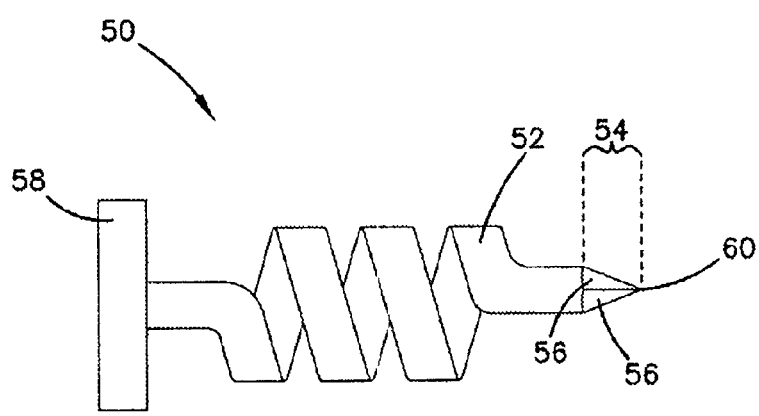
FIG. 7 is a perspective view of an implantable device according to another embodiment of the invention.
Figure 8:
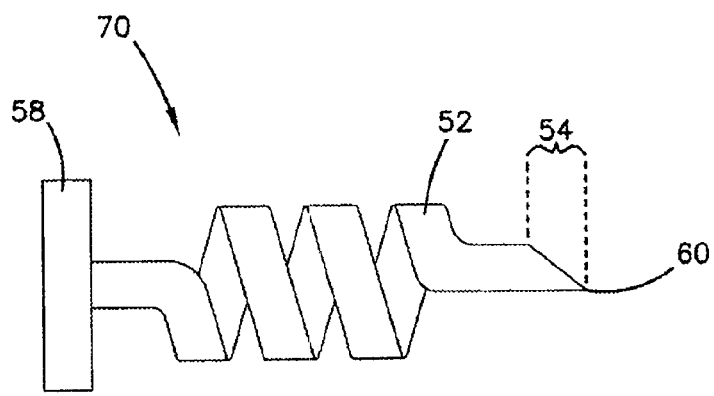
FIG. 8 is a perspective view of an implantable device according to another embodiment of the invention.

FIG. 7 shows a perspective view of an implantable device 50 according to another embodiment of the invention. The implantable device 50 has a body member 52 coupled to a cap 58. The implantable device 50 further has a tapered portion 54 and a tip 60. The tapered portion 54 and the tip 60 can together be referred to as a piercing portion. The tapered portion 54 has an increasingly smaller diameter with increasing proximity to the tip 60. The tapered portion 54 may have one or more facets 56. The tapered portion 54 may take on various configurations. By way of example, the tapered portion 54 may be pyramidal, in the shape of a cone, frusto-conical, or the like. By way of example, an alternative configuration 70 wherein the tapered portion 54 takes on a wedge shape is shown in FIG. 8.

Figure 9:
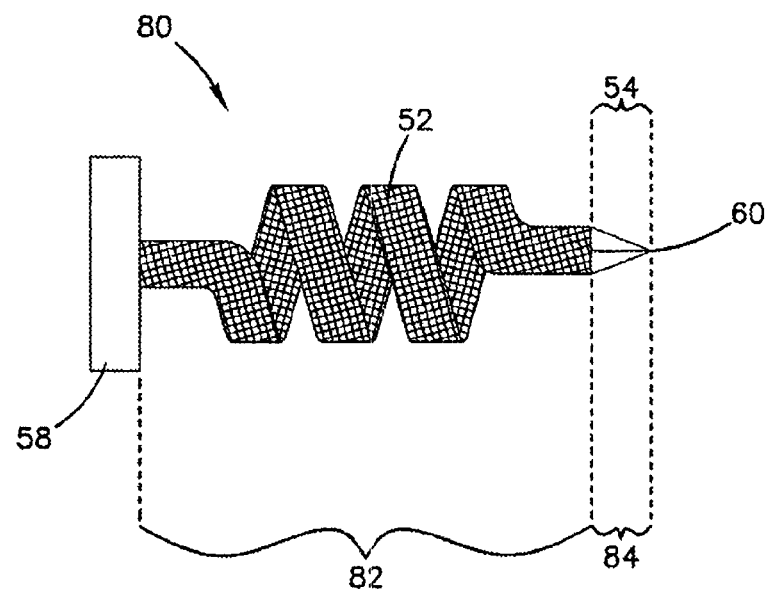
FIG. 9 is a perspective view of an implantable device having a roughened surface portion according to another embodiment of the invention.

Referring now to FIG. 9, a perspective view of an implantable device 80 according to another embodiment of the invention is shown. The implantable device 80 has a body member 52 coupled to a cap 58. The implantable device 80 further has a tapered portion 54 and a tip 60. The implantable device has a rough segment 82 and a smooth segment 84. The rough segment 82 may be roughened by sandblasting or other techniques known to those of skill in the art.

Surface roughness can be measured using the vertical scanning interferometry (VSI) mode of an optical interferometer. Based on surface data gathered with the interferometer, various measures of surface roughness can be calculated including: 1) Roughness Average ($R_a$)—the arithmetic mean of the absolute values of the surface departures from the mean plane, 2) Maximum Height (peak to valley distance) ($R_t$)—the vertical distance between the highest and lowest points over the entire dataset (highest and lowest single pixels), and 3) Average Maximum Height (average peak to valley distance) ($R_z$)—the average of the difference of the ten highest and ten lowest points in the dataset (10 highest and 10 lowest pixels—at least 4.6 μm apart from each other laterally). While not intending to be bound by theory, it is believed that $R_z$ represents the most relevant measurement for the devices of the present invention. This is because $R_z$ is least susceptible to error caused by single data pixels (points) that are random noise, or uncommon surface features like scratches or pits.

In an embodiment, the $R_z$ of the rough segment is greater than about 4.0 μm. In an embodiment, the $R_z$ of the rough segment is greater than about 6.0 μm. In an embodiment, the $R_z$ of the rough segment is greater than about 8.0 μm. In an embodiment, the $R_z$ of the rough segment is about 4.0 μm to about 12.0 μm. In an embodiment, the $R_z$ of the rough segment is about 6.0 μm to about 12.0 μm. In an embodiment, the $R_z$ of the rough segment is about 8.0 μm to about 10.0 μm.

In an embodiment, the $R_z$ of the smooth segment is less than about 4.0 μm. In an embodiment, the $R_z$ of the smooth segment is less than about 2.0 μm. In an embodiment, the $R_z$ of the smooth segment is less than about 1.0 μm. In an embodiment, the $R_z$ of the smooth segment is from about 0.0 μm to about 4.0 μm. In an embodiment, the $R_z$ of the smooth segment is from about 0.0 μm to about 2.0 μm. In an embodiment, the $R_z$ of the smooth segment is from about 0.0 μm to about 1.0 μm.

The smooth segment 84 may be formed by shielding a portion of the device while the other segment is being treated to be rough, such as being sandblasted. Alternatively, the smooth segment may be formed by removing material to form the tapered portion 54 after the roughened segment is made rough.

Figure 10:
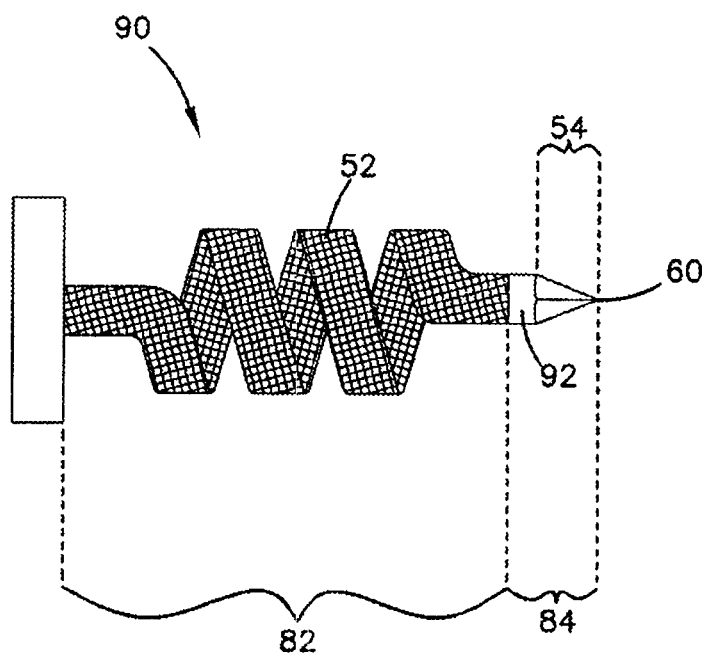
FIG. 10 is a perspective view of an implantable device having a roughened surface portion according to another embodiment of the invention.

The roughened segment may begin at various points along the body member 52 or tapered portion 54. Referring now to FIG. 10, an implantable medical device 90 is shown having a rough segment 82 and a smooth segment 84. The end of the rough segment 82 closest to the tip 60 does not extend to the tapered portion 54. Accordingly, there is a gap portion 92 disposed between the end of the rough segment 82 and the tapered portion 54. In some embodiments, the gap portion 92 is at least about 0.5 mm in length.

Figure 11:
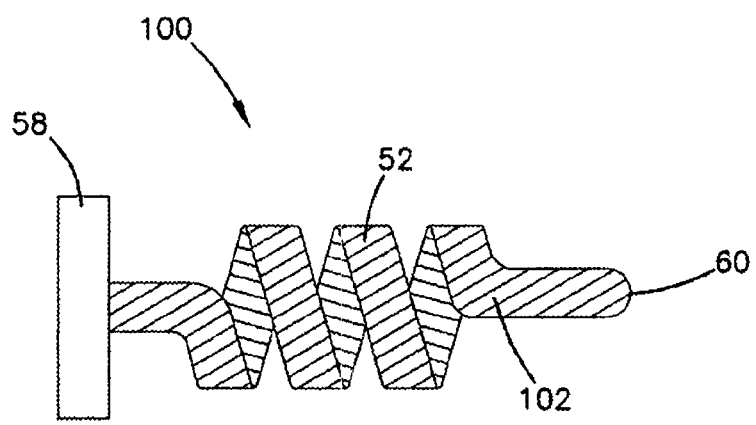
FIG. 11 is a perspective view of a coated implantable device.

Referring now to FIG. 11, an implantable medical device 100 is shown with a coated composition 102 disposed over it. The implantable medical device 100 has a body member 52 coupled to a cap 58. The implantable medical device also has a tip 60. In FIG. 11, the coated composition 102 is disposed over the entire implantable medical device except for the cap 58. In this manner, the coated composition 102 effectively blunts the sharpness of the tip 60. As described below in Example 5, blunting the tip by having a coated composition disposed over it can lead to an increase in the force necessary to insert the implantable medical device into a patient. Increased force can result in increased discomfort for the patient and/or increased chances of device breakage.

Figure 12:
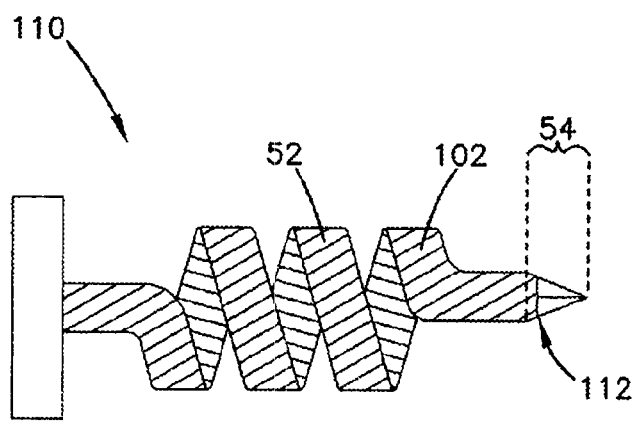
FIG. 12 is a perspective view of another coated implantable device.

Referring now to FIG. 12, an implantable medical device 110 is shown with a coated composition 102 disposed over the body member 52 as well as a part of the tapered portion 54. Specifically, the coated composition 102 has a leading edge 112 that is disposed over the tapered portion 54. In an embodiment, the body member 52 may be roughened and the tapered portion 54 may be smooth. As described below in Example 5, where the leading edge 112 of the coated composition 102 is disposed on the tapered portion 54, frictional forces encountered when the implantable medical device 110 is inserted into a patient can be sufficient to delaminate the coated composition or otherwise cause coating failure.

Figure 13:
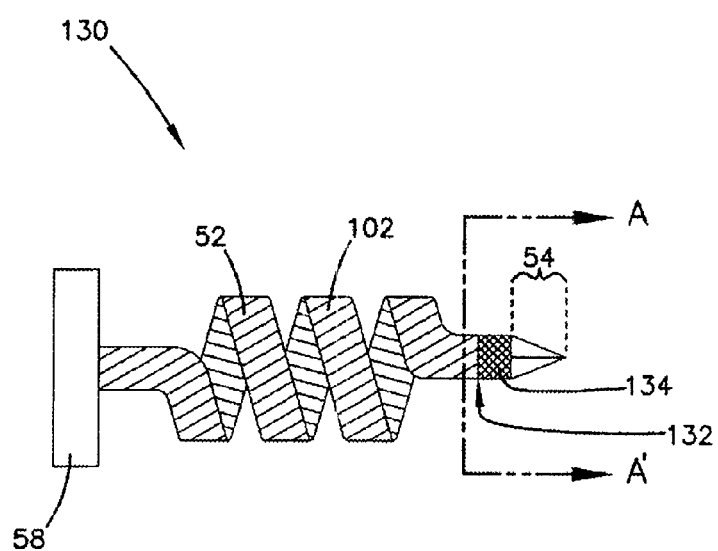
FIG. 13 is a perspective view of a coated implantable device according to an embodiment of the invention.

In an embodiment of the invention, as shown in FIG. 13, the coated composition 102 can be disposed over the implantable medical device 130 such that the coated composition 102 has a leading edge 132 disposed over a roughened segment 134 of the implantable medical device 130. As shown below in Example 5, this configuration results in a reduced incidence of coating failure. In some embodiments, the leading edge 132 is about 0.5 mm from the beginning (the side closest to the coated composition) of the tapered portion 54. In some embodiments, the leading edge is about 0.4 mm from the beginning of the tapered portion 54. The leading edge may also be about 0.3 mm, 0.2 mm, or 0.1 mm from the beginning of the tapered portion 54. In some embodiments, the leading edge is between 0.5 mm and 0.1 mm from the beginning of the tapered portion 54.

Figure 14:
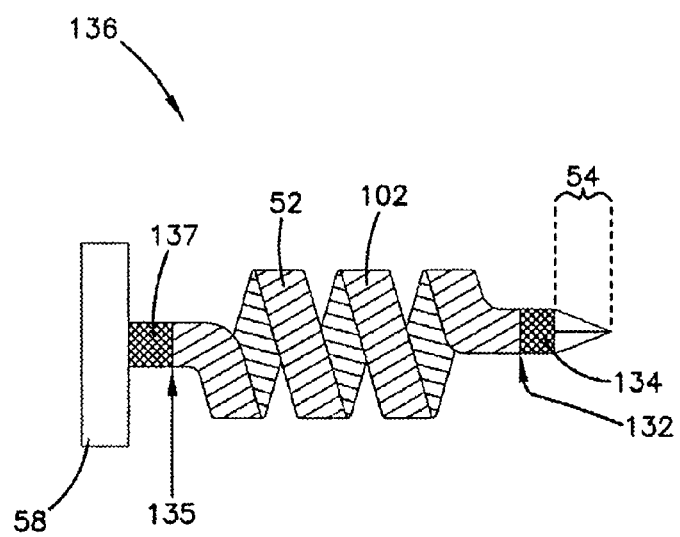
FIG. 14 is a perspective view of a coated implantable device according to another embodiment of the invention.

Referring now to FIG. 14, a perspective view of a coated implantable device 136 according to another embodiment of the invention is shown. A coated composition 102 is disposed over the implantable medical device 136 having a leading edge 132 disposed over a roughened segment 134 of the implantable medical device 130. The implantable medical device 136 has a body member 52 coupled to a cap 58 and has a tapered portion 54. The coated composition 102 has a trailing edge 135 and a gap 137 in between the cap 58 and the trailing edge 135. In some embodiments, the trailing edge 135 is about 0.5 mm from the beginning of the cap 58. In some embodiments, the trailing edge is about 0.4 mm, 0.3 mm, 0.2 mm, or 0.1 mm from the cap. In some embodiments, the trailing edge is between 0.5 mm and 0.1 mm from the cap.

Figure 15:
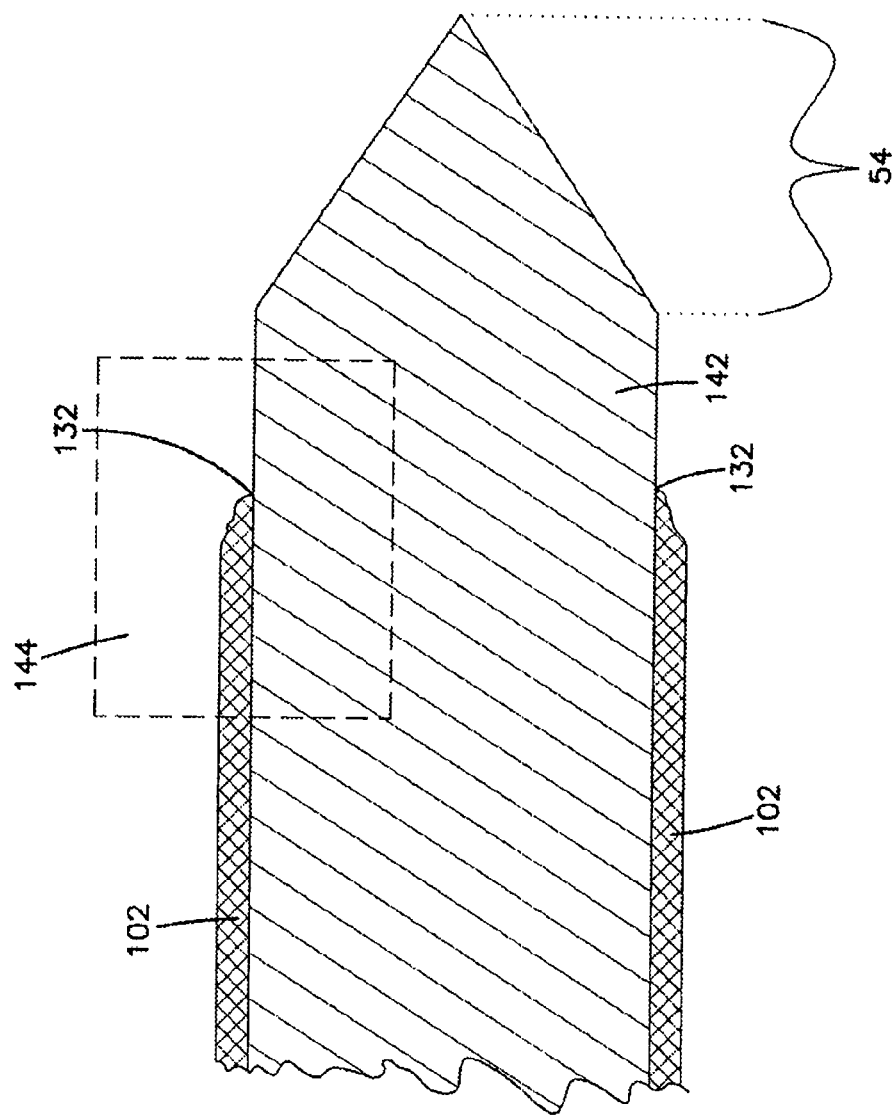
FIG. 15 is a schematic cross-sectional view of a portion of a coated implantable device taken along line A-A' of FIG. 13.

FIG. 15 is a schematic cross-sectional view of the implantable medical device of FIG. 13 taken along lines A-A' of FIG. 13. The implantable medical device includes a substrate 142. The coated composition 102 is disposed over the substrate 142. Though not shown in this view, the surfaces of the medical device, other than the tapered portion 54, are rough. The coated composition 102 has a leading edge 132 that is disposed over the rough segment.

Figure 16:
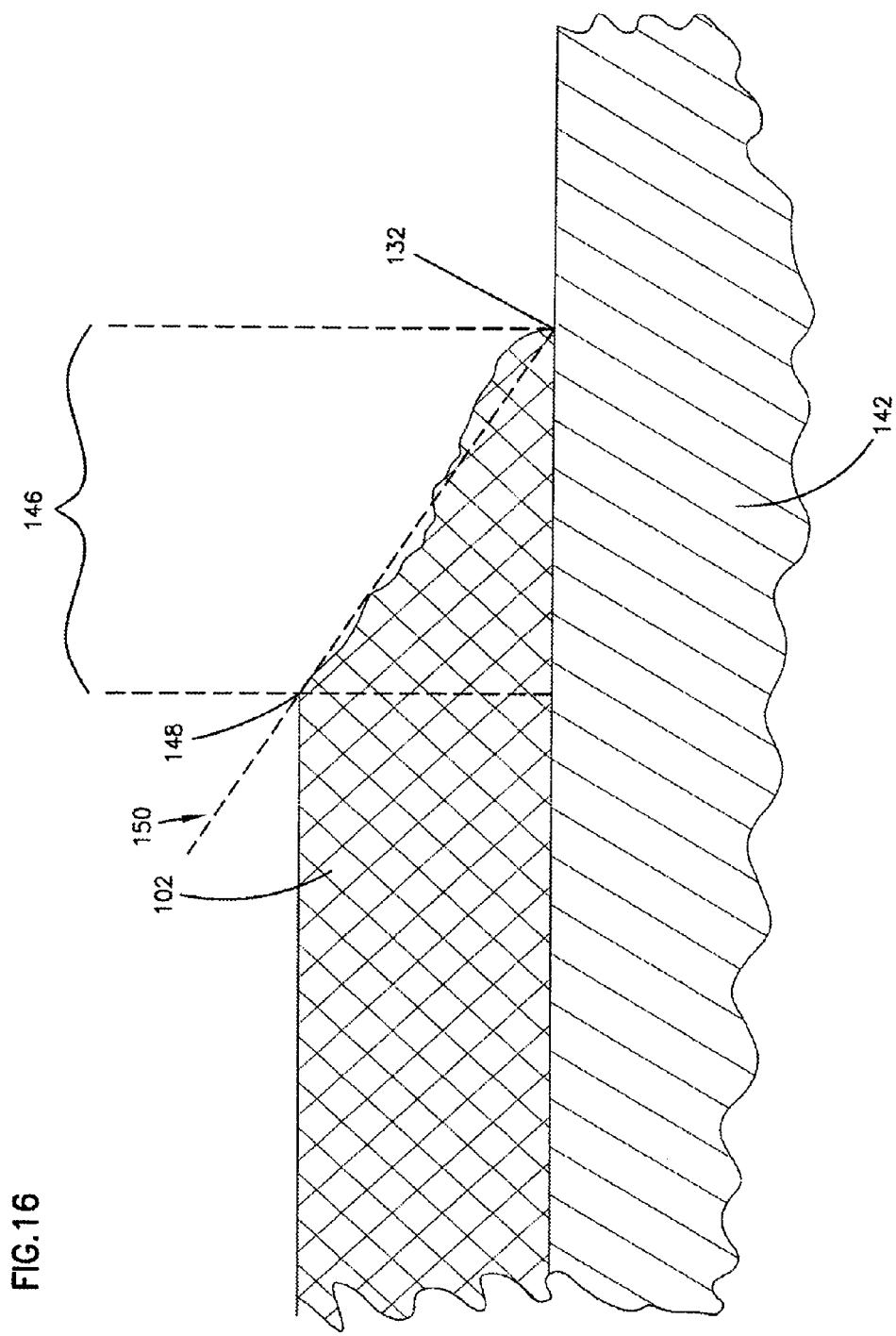
FIG. 16 is an enlarged cross-sectional view of a portion of the coated implantable device of FIG. 15.

Referring now to FIG. 16, an enlarged view of the portion of the implantable medical device in box 144 of FIG. 15 is shown. The coated composition 102 has a transition segment 146 ending at the leading edge 132. In an embodiment, a line 150 connecting the thickest point 148 of the transition segment with the leading edge 132 has a slope with respect to the surface of the substrate 142 that is less than 1.2. In an embodiment, a line 150 connecting the thickest point 148 of the transition segment with the leading edge 132 has a slope with respect to the surface of the substrate 142 that is less than 1.0. In an embodiment, a line 150 connecting the thickest point 148 of the transition segment with the leading edge 132 has a slope with respect to the surface of the substrate 142 that is less than 0.8. As used herein, slope is measured as the vertical change (in the direction of the depth of the coated composition) divided by the horizontal change (in the direction of the surface of the substrate). In an embodiment, the slope is sufficient to prevent coated composition delamination and/or coating failure.

Figure 17:
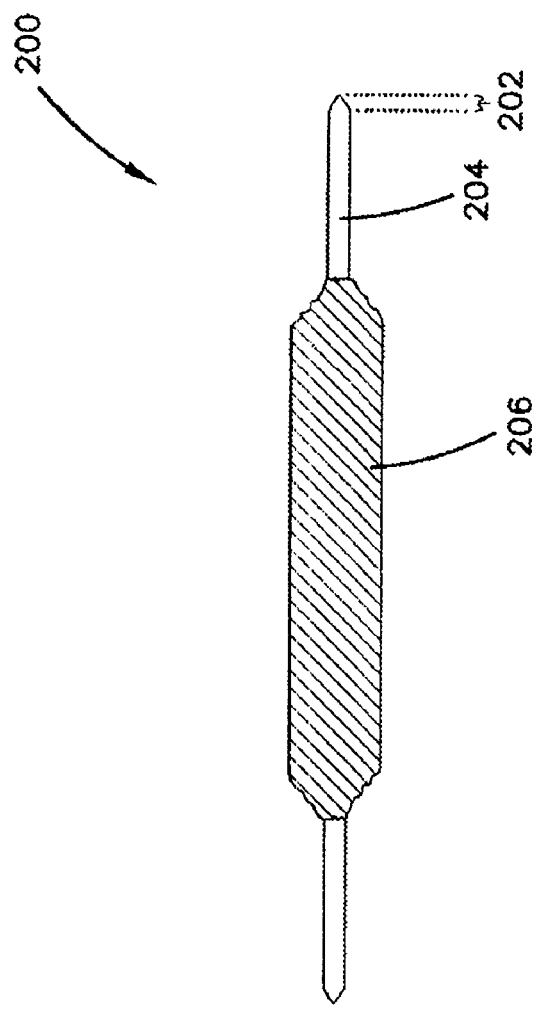
FIG. 17 is perspective view of a coated implantable device according to another embodiment of the invention.

FIG. 17 shows a perspective view of a coated implantable device 200 according to another embodiment of the invention. The coated implantable device 200 has a piercing segment 202 and a body segment 204. A coated composition 206 is disposed on the body segment 204. While piercing segment 202 is shown as pointed, it may also be non-pointed. By way of example, if the diameter of body segment 204 is relatively small, the insertion force required to place the coated implantable device 200 may not be unacceptably high even if piercing segment is non-pointed.

Figure 18:
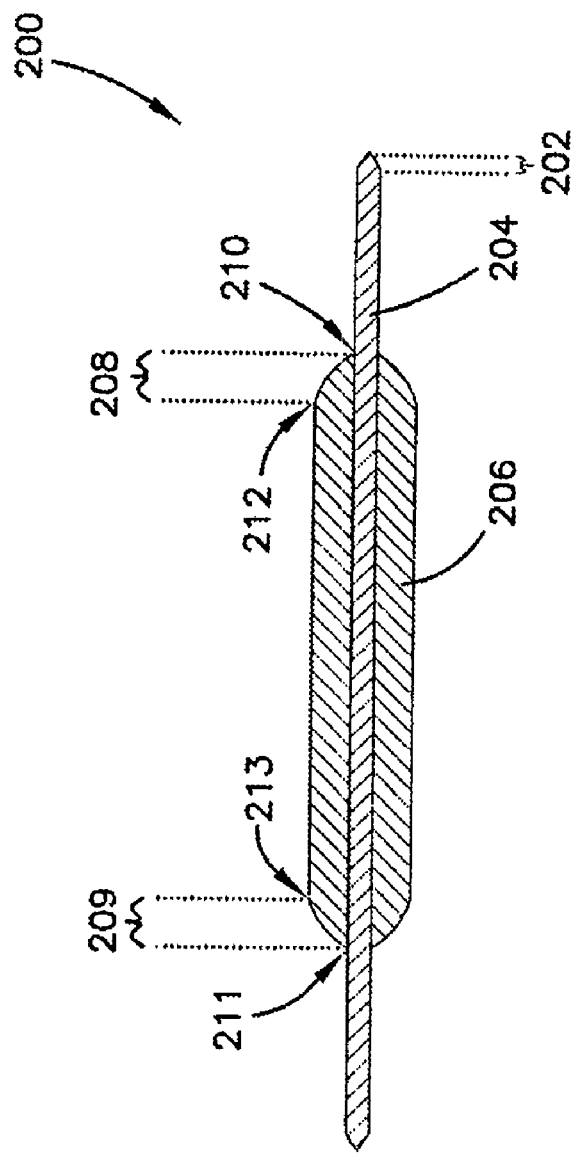
FIG. 18 is a cross-sectional view of the coated implantable device of FIG. 17.

FIG. 18 is a cross-sectional view of the coated implantable device of FIG. 17. The coated composition 206 has a leading transition segment 208 ending at the leading edge 210 and a trailing transition segment 209 ending at the trailing edge 211. In an embodiment, a line connecting the thickest point 212 of the transition segment with the leading edge 210 has a slope with respect to the surface of the substrate 204 that is less than 1.2. In an embodiment, a line connecting the thickest point 213 of the transition segment with the trailing edge 211 has a slope with respect to the surface of the substrate 204 that is less than 1.2. In an embodiment, the slope of the leading transition segment is less than 1.0. In an embodiment, the slope of the trailing transition segment is less than 1.0. In an embodiment, the slope of the leading transition segment is less than 0.8. In an embodiment, the slope of the trailing transition segment is less than 0.8.

Coating Methods

Coated compositions of the invention may be deposited using a coating system wherein the coating material is atomized ultrasonically (ultrasonic coating system). An exemplary ultrasonic coating system is disclosed in U.S. Published Application 2004/0062875 (Chappa et al.) the contents of which are herein incorporated by reference.

Figure 19:
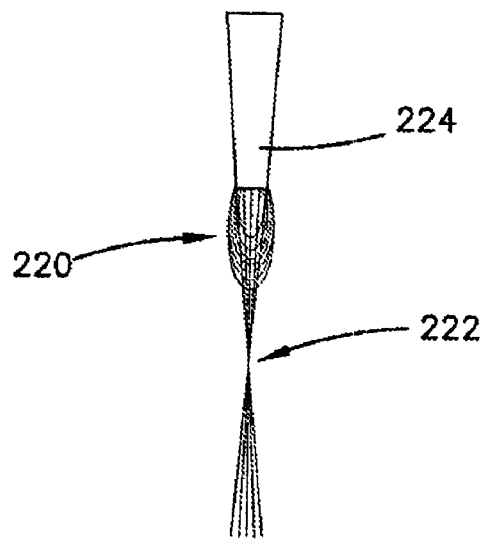
FIG. 19 is a schematic diagram of a spray stream that passes through a focal point.
Figure 20:
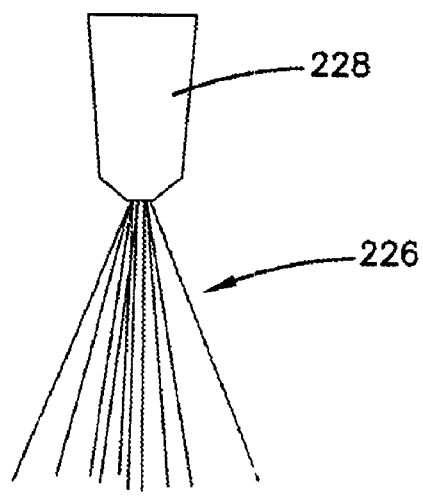
FIG. 20 is a schematic diagram of a spray stream that expands continuously as it moves away from the spray head.

Ultrasonic coating systems can produce a spray stream that narrows as it moves away from the coating head. Referring to FIG. 19, the spray stream 220 narrows as it travels away from the coating head 224 before passing through a focal point 222 (or point of smallest spray stream diameter) before starting to expand. In an embodiment, the focal point has cross-sectional diameter of about 0.5 mm to about 1.0 mm. In contrast, some other types of spray systems frequently produce a spray stream that continuously expands in diameter as it leaves the spray head. For example, referring to FIG. 20, the spray stream 226 continues to get wider as it travels away from the coating head 228.

Ultrasonic coating systems can be used to coat a device with a large degree of accuracy, particularly where the device to be coated is positioned at or near the distance of the focal point from the spray head. This is because the spray stream has a relatively small cross-sectional area at this distance and because the spray stream has a relatively small amount of spray droplets that are outside of the focal point. In an embodiment, the position of the spray stream with respect to the device to be coated is moved to cover a broader area of the device with a coated composition. In some embodiments, the device to be coated is moved. In some embodiments, the spray head is moved.

The coating solution can be pumped from a supply tube onto the ultrasonic spray head at various rates. In an embodiment, about 0.025 mls/minute to about 0.2 mls/minute of a coating solution are pumped onto the ultrasonic spray head. In an embodiment, about 0.05 to about 0.1 mls/minute of a coating solution are pumped onto the ultrasonic spray head. In an embodiment, about 1.5 mg to about 12 mg per minute of total solids are pumped onto the ultrasonic spray head. In an embodiment, about 3 mg to about 6 mg per minute of total solids are pumped onto the ultrasonic spray head.

Figure 21:
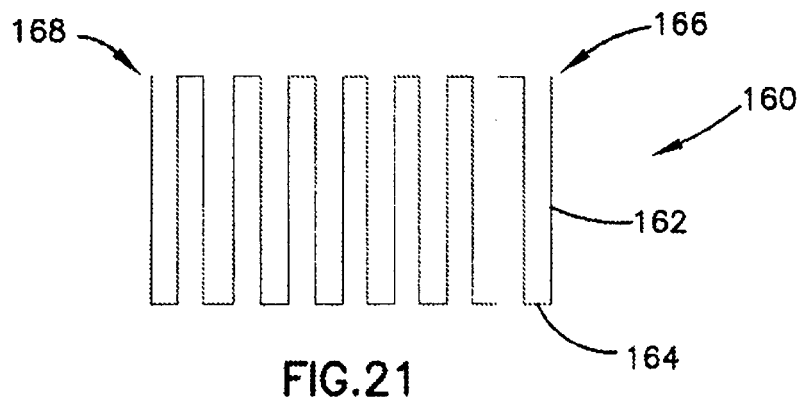
FIG. 21 is a schematic view of a grid-like coating pattern of an embodiment of the invention.

In an embodiment, a device to be coated is mounted in a pin vise, or a similar device, that is capable of rotating the device about its major or longitudinal axis. In an embodiment, the device is rotated and the ultrasonic spray head is passed back and forth over the rotating device perpendicular to the longitudinal axis. In an embodiment, the ultrasonic spray head is moved back and forth over the rotating device to be coated in a grid-like or grating-like pattern. By way of example, an exemplary grid-like pattern 160 is shown in FIG. 21. The ultrasonic spray head could be configured so that the center of the spray pattern is directly below it. Alternatively, the ultrasonic spray head could be configured so that the spray pattern is at an angle and thus the center of the spray pattern is not directly below it. Therefore, the pattern 160 shown in FIG. 21 (in addition to the patterns shown in FIGS. 22-24) indicates the path taken by the center of the spray pattern produced by the ultrasonic spray head.

The grid-like pattern starts at point 166 and ends at point 168. However, it will be appreciated that pattern can also start at point 168 and end at point 166. Alternatively, the pattern can start at any point in between point 168 and point 166. The grid-like pattern has a series of transverse sweeps 162 and longitudinal movements 164. Depending on the length of the longitudinal movements 164, any number of transverse sweeps can be used to cover a given device length. In an embodiment, the grid-like pattern includes between 3 and 100 transverse sweeps. In an embodiment, the grid-like pattern includes between 3 and 100 longitudinal movements 164.

The length of the longitudinal movements 164 can be varied depending on various factors including the cross-sectional diameter of the spray pattern as it meets the surface of the device to be coated. It has been found that when the longitudinal movements are greater than a desired amount, and when the grid-like pattern is followed from the same starting place on each pass, then the surface of the coated composition becomes bumpy. For example, the coated composition can become bumpy where the longitudinal movements are greater than about 0.2 mm. FIG. 26 shows a schematic cross-sectional view 190 of a coated composition 192 having a bumpy surface. The surface has a regular pattern of peaks 194 and valleys 196. It will appreciated that the specific limit on how big the longitudinal movements can be before the resulting surface of the coated composition becomes bumpy will depend on a number of factors including the diameter of the spray pattern and the relative spray density of various parts of the spray pattern. In an embodiment, the longitudinal movements are less than or equal to about 0.4 mm. In an embodiment, the longitudinal movements are less than or equal to about 0.3 mm. In an embodiment, the longitudinal movements are less than or equal to about 0.2 mm.

FIGS. 22-24 show exemplary grid-like patterns superimposed over exemplary devices. In FIG. 22, the first transverse sweep passes beyond the end of the tapered portion 172 and tip 176 of the device. Coating a device using this orientation of the grid-like pattern with respect to the implantable device generally results in the coated composition covering the tip 176 and the tapered portion 172 of the device. An example of this coated composition deposition pattern is shown in FIG. 11. Where the coated composition covers the tip 176, the tip 176 is blunted.

In FIG. 23, the first transverse sweep of the ultrasonic coating head passes over the tapered portion 172 of the device. Coating a device using this orientation of the grid-like pattern generally results in the coated composition covering at least a part of the tapered portion 172 of the device but not the tip 176. An example of this deposition pattern is shown in FIG. 12.

In FIG. 24, the first transverse sweep of the ultrasonic coating head passes over the body portion 178 of the device. Coating a device using this orientation of the grid-like pattern with respect to the device generally results in the coated composition covering the body portion 178 of the device but not the tip 176 or the tapered portion 172 of the device. Using other terms, in this embodiment, the coated composition covers the body of the device but not the piercing portion. An example of this deposition pattern is shown in FIG. 13.

In an embodiment, the grid-like pattern is followed by the ultrasonic coating head multiple times (performs multiple passes) in order to deposit a coated composition onto the implantable device. On each pass through the grid-like pattern, an amount of the coated composition is deposited. Thus, the precise number of passes made by the ultrasonic coating head can be changed based on the total amount of coated composition desired. In an embodiment, the mass of the coated composition is from about 500 μg to about 5000 μg dry weight. In an embodiment, the mass of the coated composition is from about 1000 μg to about 3000 μg dry weight.

In some embodiments, the same longitudinal starting position is used with respect to the device to be coated for each additional pass. By way of example, for each pass, the ultrasonic coating head would start at the same point on the longitudinal axis of the device and follow the same pattern. Alternatively, the longitudinal starting position of the ultrasonic coating head may change with each additional pass. In an embodiment, the ultrasonic coating head may advance to a position somewhat closer to the proximal end of the device with each additional pass made. Thus, referring to FIG. 25, the first transverse sweep of the first pass may start at a point 182. Then, the first transverse sweep of the second pass may start at an offset position such as point 184 that is farther away from the tip 176. Similarly, the first transverse sweeps of the third pass and fourth pass begin at points 186 and 188 respectively that are even farther away from the tip 176. This technique of moving the starting position in the direction of arrow 180 can be used to extend the distance over which the coated composition builds up to its full thickness and thereby reduce the slope of the transition segment of the coated composition.

Successive passes can be performed with or without a time delay in between passes. By way of example, depending on the coating composition used and the solvents therein, extra time can be inserted in between successive passes to allow for solvent evaporation, or for other chemical processes to occur, before the next pass is performed.

Methods of applying a coating composition in accordance with embodiments of the invention can be used to manipulate or control the slope of the transition segment of the coated composition. Where it is desired to make the slope as low as possible, the longitudinal starting position of each additional pass can be increased. This can also be described as changing the offset between successive passes. By way of example, the offset between successive passes could be 0.5 mm. This would generally result in a longer transition segment with a lower slope in comparison with a coated composition that was applied with an offset between successive passes of less than 0.5 mm, such as 0.2 mm. In an embodiment, the offset between successive passes in between about 0.1 mm and 2.0 mm.

Embodiments of the invention allow the slope of the transition segment to be selected to suit the particular application. By way of example, for coated compositions that are disposed on devices that will undergo greater stresses, such as frictional stresses, the slope of the transition segment can be reduced to prevent damage to the coated composition such as delamination or failure. Bone screws are an example of a device that encounter significant stresses when inserted into the tissues of a patient. Embodiments of the invention can be used to dispose coated compositions on devices with a transition segment having a slope of less than 1.0. A slope of 1.0 is equivalent to an angle of 45 degrees with respect to the surface of the device. In an embodiment, the slope of the transition segment can be less than about 0.8, 0.6, 0.4, or 0.2.

Conversely, where it is desired to maximize the amount of coated composition on a device, and where stresses that could lead to delamination are a lesser concern, embodiments of the invention can allow the slope of the transition segment to be increased. By way of example, some intra-arterial devices undergo lesser frictional stresses, depending on how they are inserted into the body. In an embodiment, the slope of the transition segment may be greater than 1.0. Specifically, the slope of the transition segment on such a device can be greater than about 1.2, 1.4, 1.6, or 1.8.

In some embodiments of the invention, such as described in FIGS. 14 and 17, coated compositions have both a leading transition segment and a trailing transition segment. The leading transition segment and the trailing transition segment may have slopes that are the same or different. By way of example, in some embodiments, the leading transition segment has a slope that is less than the trailing transition segment. An example of this would be in a device where it is believed that the leading transition segment will encounter greater frictional stresses than the trailing transition segment.

Embodiments of the invention can be used to dispose a coating composition onto the surface of a device with a high degree of precision. In an embodiment, the edge of a coated composition can be positioned with a degree of precision equal to about 0.5 mm. By way of example, if there is a portion of a device that should not be covered, embodiments of the invention allow a coated composition to be directed to point within 0.5 mm of this portion while minimizing overspray onto the portion not to be covered. Embodiments of the invention can allow the edge of a coated composition to be positioned less than or equal to about 0.4, 0.3, 0.2, or 0.1 mm away from an uncovered portion of a device.

Figure 27:
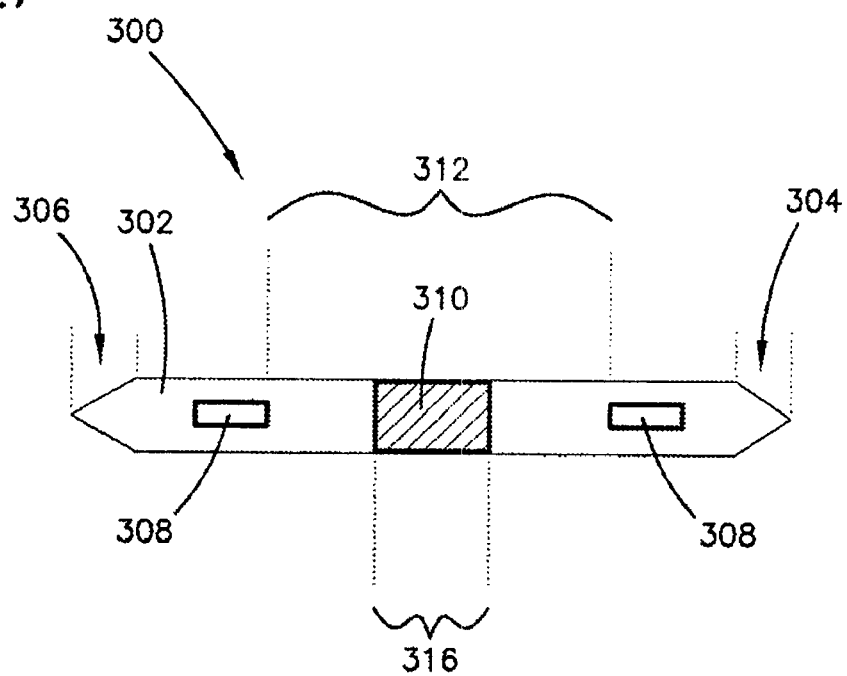
FIG. 27 shows a device in accordance with an embodiment of the invention.

Referring now to FIG. 27, a device 300 is shown in accordance with an embodiment of the invention. The device 300 has a body segment 302 and a first tapered segment 304 and a second tapered segment 306. The first tapered segment 304 and/or the second tapered segment 306 can be piercing segments. The device has two components 308 and a coated region 310. Such a device could be produced in various sizes. By way of example, the distance 312 between the two components 308 could be about 1.5 mm. Embodiments of the invention allow the coated region 310 to have a length 316 of about 0.5 mm. That is, because the coated composition can be directed to a point within 0.5 mm of a portion that remains uncoated (components 308) there is still room to make the coated region 310 about 0.5 mm in length.

The components 308 can be any type of device or feature that should remain uncoated. By way of example, components 308 can be sensors for measuring temperature, pulse, blood composition, infectious agents, or any other physiological properties. Components 308 can also be electrical contacts for providing an electrical stimulus or for interfacing with tissues of the patient such as nerves. Components 308 can also be apertures to one or more lumens within the device. Components 308 can be any type of structure that remains uncoated.

While device 300 is described as having components 308, one of skill in the art will appreciate that embodiments of the invention can be similarly used to precisely coat devices having other types of features that should remain uncoated.

Figure 28:
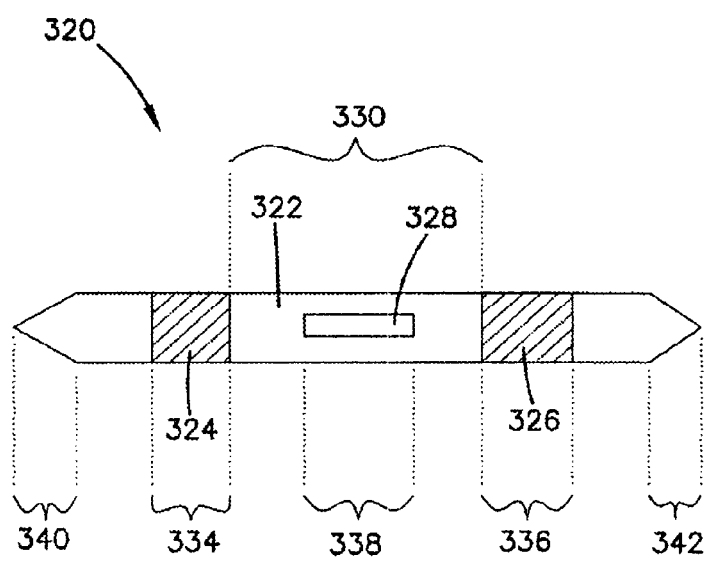
FIG. 28 shows a device in accordance with another embodiment of the invention.

Referring now to FIG. 28, a device 320 is shown in accordance with an embodiment of the invention. The device 320 has a body segment 322, a first coated segment 324 and a second coated segment 326. The device has a component 328 having a length 338 and a first and second tapered segment 340, 342. The component 328 is disposed on the surface of device 320. As used herein, when a component is described as being disposed on the surface of a medical device, this includes where the component is partially or fully disposed within the body of the medical device such as with a lumen or an aperture to a lumen. This phrase also includes where the component only contacts the surface of the medical device, such as with a contact plate adhered to the surface of a medical device. The device 320 could be produced in various sizes. By way of example, the distance 330 between the first coated segment 324 and the second coated segment 326 could be about 1.5 mm. Embodiments of the invention allow the first coated segment 324 and the second coated segment 326 to each have a length of about 0.5 mm, while remaining at least about 0.5 mm away from the tapered segments and the component 328.

Figure 29:
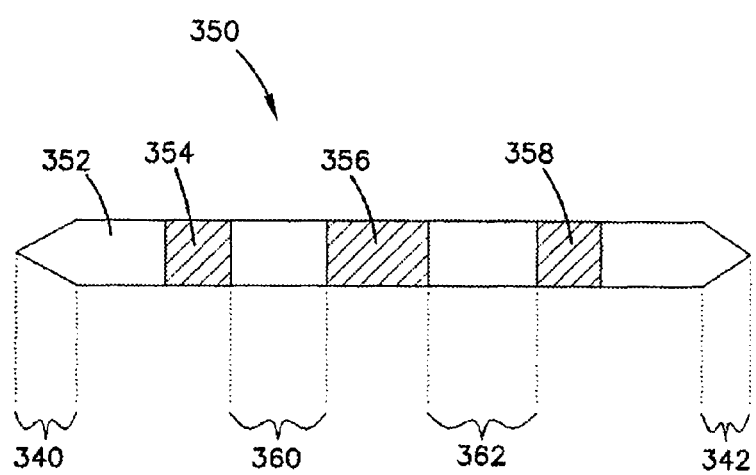
FIG. 29 shows a device in accordance with another embodiment of the invention.

Referring now to FIG. 29, a device 350 is shown in accordance with another embodiment of the invention. The device 350 has a body segment 352, a first coated segment 354, a second coated segment 356, and a third coated segment 358. The device has a first and second tapered segment 340, 342. In an embodiment of the invention, the coated segments release different bioactive agents. In an embodiment, the coated segments release the same bioactive agent but at different rates. In an embodiment, the coated segments release the same bioactive agent at the same rate. For example, the first coated segment 354 and the third coated segment 358 could release a first agent, such as tacrolimus, while the second coated segment 356 could release a second agent, such as rapamycin. It will be appreciated that many different combinations of bioactive agents and release rates are possible.

In some embodiments, it may be desirable to prevent the coated segments from overlapping or touching on their edges. However, it may be desirable to position the coated segments close to one another in order to maximize the amount of coated composition that can be deposited on the device. Embodiments of the invention include devices having coated segments, such as in FIG. 29, that can be positioned close to one another without having an overlap between them. Embodiments of the invention also include methods for producing the same. For example, the distance between the coated segments can be about 0.5 mm or less. In an embodiment, the distance between the coated segments can be about 0.4 mm or less. In some embodiments, the distance between the coated segments can be about 0.3 mm or less. In an embodiment, the distance between the coated segments can be about 0.2 mm or less.

Figure 30:
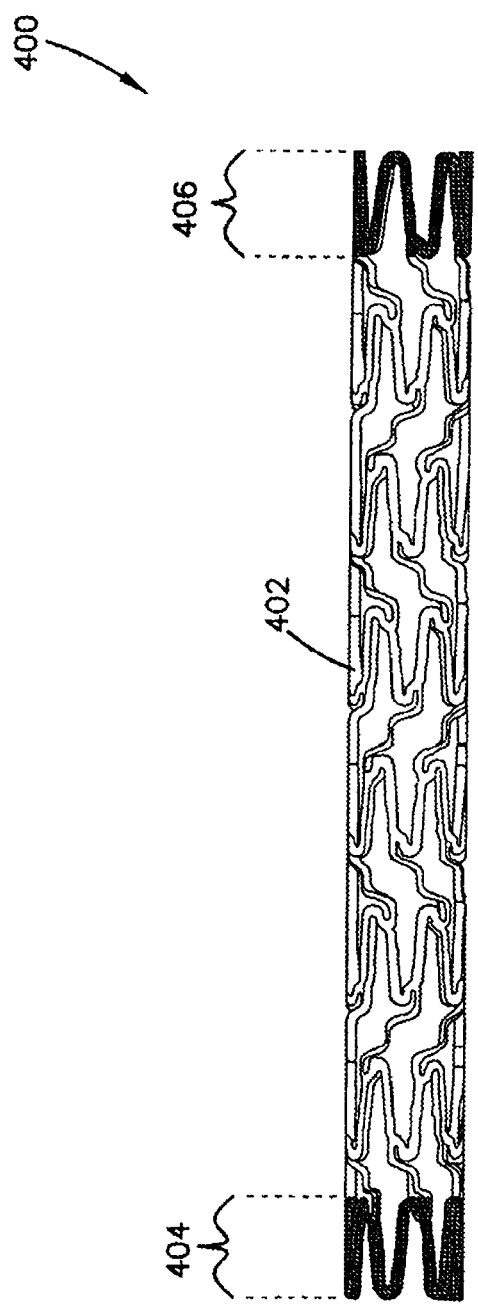
FIG. 30 shows a device in accordance with another embodiment of the invention.

Embodiments of the invention can be used with many different types of devices. For example, radioactive stents have been used in the past in an attempt to reduce restenosis. However, many studies have found that radioactive stents allow restenosis to occur in a characteristic "candy wrapper" pattern wherein restenosis occurs primarily beyond either end of the stent but not in the middle. Embodiments of the invention can allow a coated composition to be positionally deposited in a location on the device to reduce this type of restenosis. More generally, embodiments of the invention include a device having coated segments on one or both ends. Referring now to FIG. 30, another embodiment of the invention is shown. A device 400 is shown having a substrate 402, a first end segment 404, and a second end segment 406. The first end segment 404 and the second end segment 406 both have a coated composition comprising a bioactive agent disposed thereon. The coated compositions of the first end segment 404 and the second end segment 406 may have the same bioactive agent or different bioactive agents. For example, in an embodiment, the device is a stent that is radioactive and both the coated compositions of the first end segment 404 and the second end segment 406 comprise a bioactive agent effective to reduce restenosis. In an embodiment, the substrate 402 is not covered by a coated composition in between the first end segment 404 and the second end segment 406. In an embodiment, the substrate 402 is covered by a coated composition that is different from the coated compositions of the first end segment 404 and the second end segment 406.

With some stent designs, after the stent is inserted into a patient, blood flows through the stent in one direction. This one-way flow can affect delivery of a bioactive agent to the tissue surrounding the stent. For example, it can be more difficult to provide a therapeutic amount of a bioactive agent to the region of tissue on the upstream side of the stent compared to the downstream side. Accordingly, it can be advantageous to provide different bioactive agents on the two ends of a stent or provide the same drug in different amounts or with different release rates on the two ends. In another embodiment, the device is a stent (radioactive or not) and the coated compositions of the first end segment 404 and the second end segment 406 comprise different bioactive agents or comprise the same bioactive agents but in different amounts or with different release rates. In an embodiment, the first end segment 404 and the second end segment 406 are about 2.0 mm in length or less. In an embodiment, the first end segment 404 and the second end segment 406 are about 1.5 mm in length or less. In an embodiment, the first end segment 404 and the second end segment 406 are about 1.0 mm in length or less. In an embodiment, the first end segment 404 and the second end segment 406 are about 0.5 mm in length or less.

Many stents are expanded into position inside a patient by a balloon that is inflated. For many types of stent delivery systems, the stent is crimped onto the deflated balloon. If the stent is not crimped onto the balloon tightly enough, there is a risk that the stent disengage from the delivery device inappropriately. However, particularly where the stent has a coated composition disposed thereon, the action of crimping the stent tightly onto the balloon can lead to damage to the device. For example, the coated composition can be damaged during the crimping process.

In an embodiment, the invention provides a method of adhering the stent to the balloon that reduces or eliminates the need for crimping of the stent. In an embodiment, the invention provides a method of increasing the static friction of the surface of an implantable medical device. Some compositions, such as poly(ethylene-co-vinyl acetate) pEVA, have adhesive like properties. Application of a pEVA layer over a coated composition comprising a bioactive agent generally does not interfere with release of the bioactive agent. Accordingly, a pEVA layer can be used over a coated composition to promote adhesion between a medical device, such as a stent, and a delivery device, such as a balloon. However, if the pEVA layer covers too much of the surface area of the stent, then sticking problems occur that can interfere with the use of the device. In an embodiment, one or more bands (or segments) of a composition having adhesive like properties is disposed over a coated composition on a device to provide a desired level of adhesion between the stent and the uninflated balloon.

Figure 31:
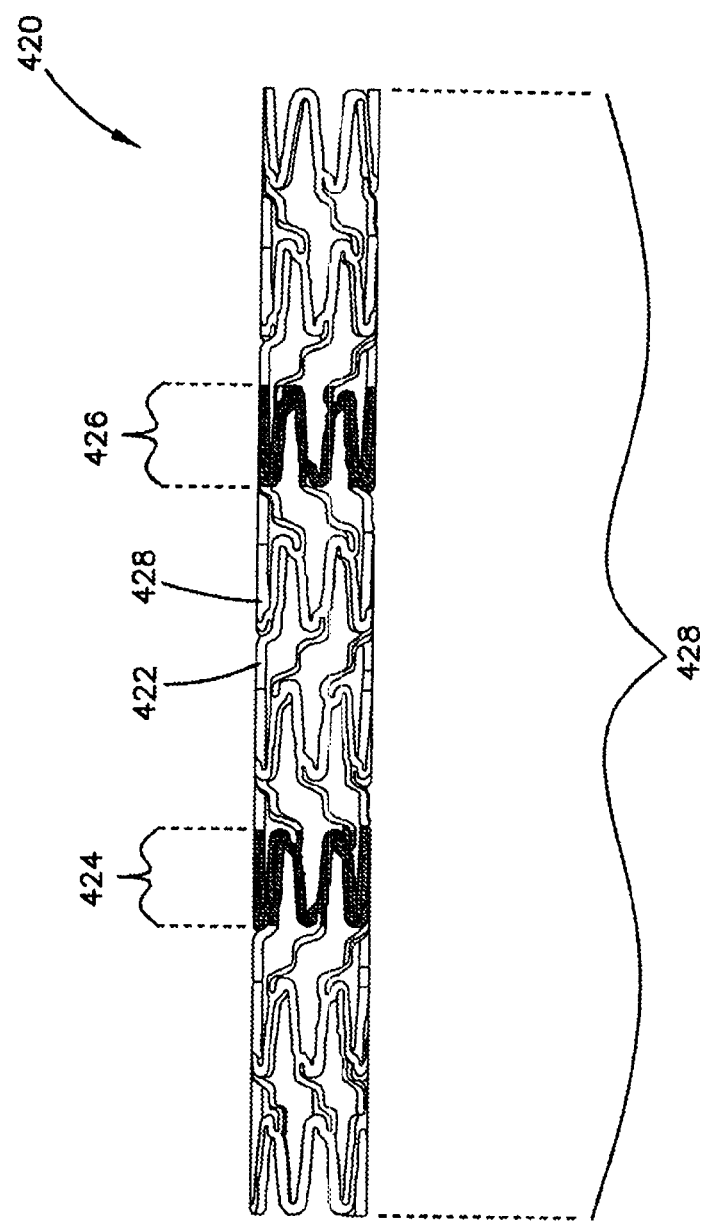
FIG. 31 shows a device in accordance with another embodiment of the invention.
Figure 32:
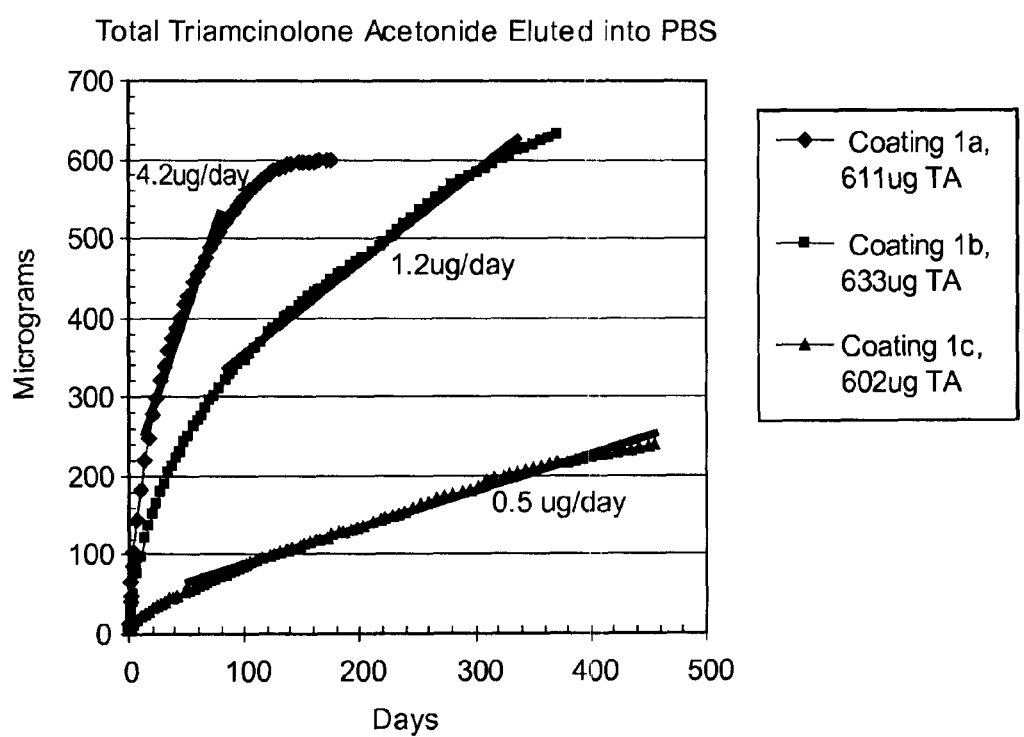
FIG. 32 is a graph showing the total triamcinolone acetonide eluted into PBS for coatings 1*a* (611 µg TA), 1*b* (633 µg TA), and 1*c* (602 mg TA).
Figure 33:
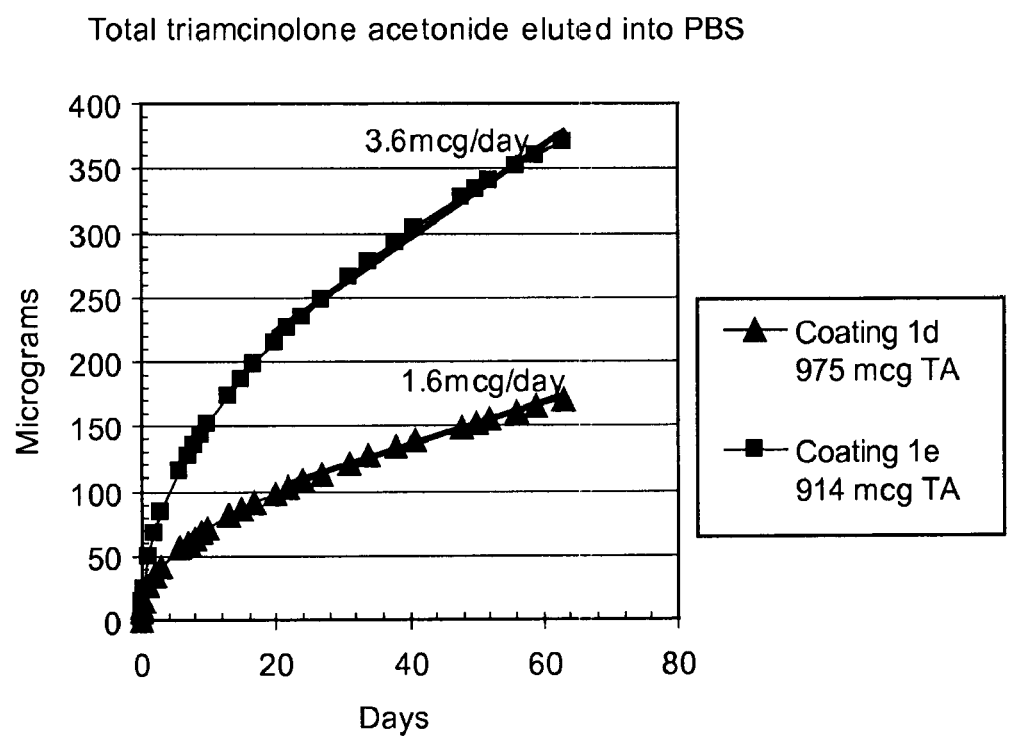
FIG. 33 is a graph showing the total triamcinolone acetonide eluted into PBS for coatings 1*d* (975 mcg TA) and 1*e* (914 mcg TA).
Figure 34:
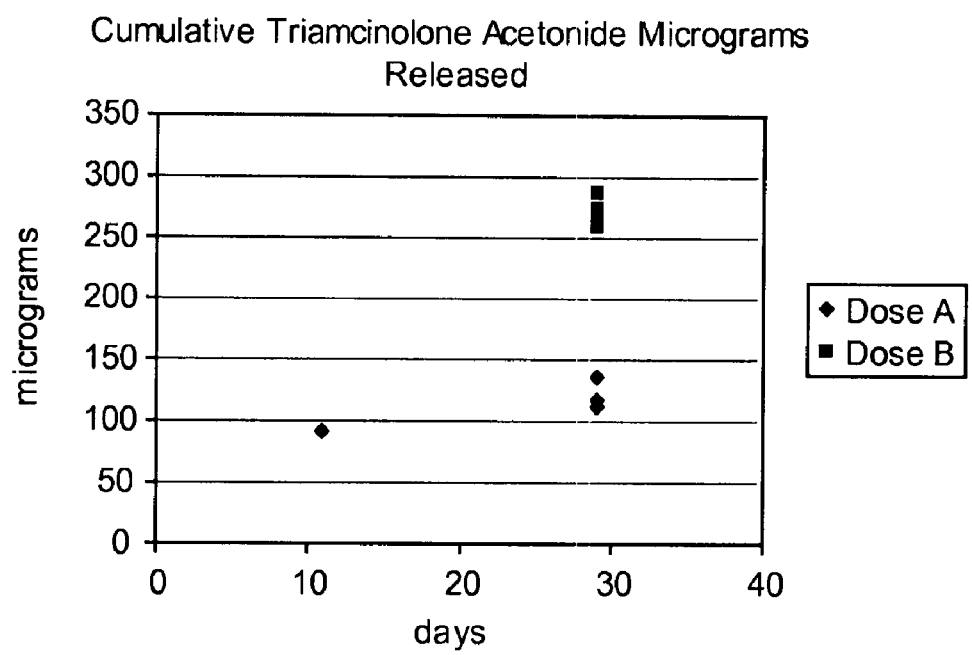
FIG. 34 is a graph showing the cumulative triamcinolone acetonide micrograms released for Dose A and B.

Referring now to FIG. 31, an embodiment of the invention is shown. A device 420 is shown having a substrate 422, a first adhesive segment 424, and a second adhesive segment 426. The substrate 422 can have a coated composition 428 disposed thereon. The first adhesive segment 424 and the second adhesive segment 426 can be disposed over the coated composition 428. In an embodiment, the first adhesive segment 424 and the second adhesive segment 426 comprise a composition having adhesive like properties. In an embodiment, the first adhesive segment 424 and the second adhesive segment 426 comprise a composition having adhesive like properties that does not interfere with the delivery of a bioactive agent from the coated composition 428. In an embodiment, the first adhesive segment 424 and the second adhesive segment 426 comprise at least about 90% pEVA by weight. In an embodiment, the first adhesive segment 424 and the second adhesive segment 426 comprise at least about 95% pEVA by weight.

It is believed that if the adhesive segments cover too much of the surface of the device, sticking problems may occur. In an embodiment, the first adhesive segment 424 and the second adhesive segment 426 are about 2.0 mm in length or less. In an embodiment, the first adhesive segment 424 and the second adhesive segment 426 are about 1.5 mm in length or less. In an embodiment, the first adhesive segment 424 and the second adhesive segment 426 are about 1.0 mm in length or less. In an embodiment, the first adhesive segment 424 and the second adhesive segment 426 are about 0.5 mm in length or less.

In some embodiments, the surface of the device can be pretreated prior to provision of the coating composition. Any suitable surface pretreatment commonly employed in coating implantable devices can be utilized in accordance with the invention, including, for example, treatment with silane, polyurethane, parylene, and the like. For example, Parylene C (commercially available from Union Carbide Corporation), one of the three primary variants of parylene, can be used to create a polymer layer on the surface of a medical device. Parylene C is a para-xylylene containing a substituted chlorine atom, which can be coated by delivering it in a vacuum environment at low pressure as a gaseous polymerizable monomer. The monomer condenses and polymerizes on substrates at room temperature, forming a matrix on the surface of the medical device. The coating thickness can be controlled by pressure, temperature, and the amount of monomer used. The parylene coating provides an inert, non-reactive barrier.

Specific Embodiments

The following illustrates some specific embodiments of the invention but is provided herein only as exemplary and does not serve to limit the scope of the invention.

In an embodiment, the invention includes a method of forming a coated medical device comprising depositing a coated composition onto a medical device comprising a roughened segment and a smooth segment, the coated composition comprising a polymer and a bioactive agent and having a leading edge provided on the roughened segment. The coated composition can include a trailing edge provided on the roughened segment. The coated composition can adhere to the substrate surface sufficiently to reduce delamination of the coated composition. The leading edge can be within about 0.5 mm of the smooth segment. The coated composition can be deposited only on the roughened segment. The roughened segment can have a roughness $R_z$ of greater than about 4 µm. The smooth segment can have a roughness $R_z$ of less than about 4 µm. The coated composition can be deposited onto the medical device with an ultrasonically atomized spray stream. The ultrasonically atomized spray stream can move in a grid-like pattern over the medical device. The grid-like pattern can include a plurality of sweeps and a plurality of longitudinal movements. The longitudinal movements can be about 0.4 mm or less. In an embodiment, the longitudinal movements are about 0.3 mm or less. In an embodiment, the longitudinal movements are about 0.2 mm or less. In an embodiment, each longitudinal movement is separated from the next longitudinal movement by one or more transverse sweeps. The grid-like pattern can be repeated a plurality of times. In an embodiment, each grid-like pattern of movement begins in the same location on the length axis of the medical device. In an embodiment, each grid-like pattern of movement begins in a different location on the length axis of the medical device. The coated composition can include a leading transition segment, the leading transition segment having increasing thickness with increasing distance from the leading edge. In an embodiment, the slope of a line connecting the leading edge to the outer surface of the thickest portion of the leading transition segment is no greater than 1.0 as measured relative to the surface of the medical device. The coated composition can include a trailing transition segment, the trailing transition segment having increasing thickness with increasing distance from the trailing edge. In an embodiment, the slope of a line connecting the trailing edge to the outer surface of the thickest portion of the trailing transition segment is no greater than 1.0 as measured relative to the surface of the medical device. The polymer can include polyalkyl(meth)acrylate, aromatic poly(meth)acrylate, or a combination of polyalkyl(meth)acrylate and aromatic poly(meth)acrylate. The polymer can include polyalkyl(meth)acrylate selected from the group consisting of polyalkyl(meth)acrylates having alkyl chain lengths in the range of 2 to 8 carbons. The polymer can include poly(n-butyl)methacrylate. The polymer can include aromatic poly(meth)acrylate selected from the group consisting of polyaryl(meth)acrylate, polyaralkyl(meth)acrylate, and polyaryloxyalkyl(meth)acrylate. The aromatic poly(meth)acrylate can include aryl groups having from 6 to 16 carbon atoms. The coated composition can include poly(ethylene-co-vinyl acetate). The poly(ethylene-co-vinyl acetate) can include a vinyl acetate concentration in the range of 10% to 90% by weight. The coated composition can include two or more layers. The method can further include applying a surface pretreatment. The surface pretreatment can include silane, polyurethane, parylene, or combinations thereof. The bioactive agent can include of triamcinolone acetonide, 13-cis retinoic acid, 5-fluorouridine, and combinations thereof. The bioactive agent can be released in a therapeutically effective amount for a period of 6 months or more when the medical device is implanted in a patient. In an embodiment, the bioactive agent is triamcinolone acetonide, and the triamcinolone acetonide has a release rate in the range of 0.5 µg/day to 2 µg/day when the medical device is implanted in an eye. In an embodiment, the coated composition has a thickness of 0.1 µm to 100 µm.

In an embodiment, the invention includes a method of forming a coated implantable medical device comprising depositing a coated composition onto a medical device, the medical device comprising a body segment and a piercing segment, the coated composition comprising a leading edge provided over the body segment, the coated composition comprising a polymer and a bioactive agent. The coated composition can include a trailing edge provided on the body segment. The coated composition can adhere to the substrate surface sufficiently to reduce delamination. In an embodiment, the leading edge is within about 0.5 mm of the piercing segment. In an embodiment, the coated composition is deposited only onto the body segment. The coated composition can be deposited onto the medical device with an ultrasonically atomized spray stream. The ultrasonically atomized spray stream can move in a grid-like pattern over the medical device. The grid-like pattern can include a plurality of sweeps and a plurality of longitudinal movements. In an embodiment, the longitudinal movements are less than about 0.4 mm and each longitudinal movement is separated from the next longitudinal movement by one or more transverse sweeps. The movement in a grid-like pattern can be repeated a plurality of times. In an embodiment, the coated composition can include a leading transition segment, the leading transition segment having increasing thickness with increasing distance from the leading edge, wherein the slope of a line connecting the leading edge to the outer surface of the thickest portion of the leading transition segment is no greater than 1.0 as measured relative to the surface of the medical device. In an embodiment, the coated composition can include a trailing transition segment, the trailing transition segment having increasing thickness with increasing distance from the trailing edge, wherein the slope of a line connecting the trailing edge to the outer surface of the thickest portion of the trailing transition segment is no greater than 1.0 as measured relative to the surface of the medical device. The polymer can include polyalkyl(meth)acrylate, aromatic poly(meth)acrylate, or a combination of polyalkyl(meth)acrylate and aromatic poly(meth)acrylate. The polymer can include polyalkyl(meth)acrylate selected from the group consisting of polyalkyl(meth)acrylates having alkyl chain lengths in the range of 2 to 8 carbons. The polymer can include poly(n-butyl)methacrylate. In an embodiment, the polymer includes aromatic poly(meth)acrylate selected from the group consisting of polyaryl(meth)acrylate, polyaralkyl(meth)acrylate, and polyaryloxyalkyl(meth)acrylate. The aromatic poly(meth)acrylate comprises aryl groups can have from 6 to 16 carbon atoms. The coated composition can further include poly(ethylene-co-vinyl acetate). In an embodiment, the poly(ethylene-co-vinyl acetate) has a vinyl acetate concentration in the range of 10% to 90% by weight. The coated composition can includes two or more layers. The method can further include applying a surface pretreatment. The surface pretreatment can be selected from the group consisting of silane, polyurethane, parylene, or combinations thereof. The bioactive agent can be selected from the group consisting of triamcinolone acetonide, 13-cis retinoic acid, 5-fluorouridine, and combinations thereof. In an embodiment, the coated composition has a thickness of 0.1 µm to 100 µm.

In an embodiment, the invention includes a medical device having a substrate with a surface, a coated composition having an edge provided on the substrate surface, the composition comprising a bioactive agent and a polymer, and an uncoated component disposed in or on the substrate surface, wherein the edge of the coated composition is within 0.5 mm of the uncoated component. In an embodiment, the coated composition adheres to the substrate surface sufficiently to reduce delamination. The uncoated component can be a sensor. The uncoated component can be a lumen. The uncoated component can be a piercing segment. The edge of the coated composition can be within about 0.4 mm of the uncoated component. The polymer can include polyalkyl(meth)acrylate, aromatic poly(meth)acrylate, or a combination of polyalkyl(meth)acrylate and aromatic poly(meth)acrylate. In an embodiment, the polymer includes polyalkyl(meth)acrylate selected from the group consisting of polyalkyl(meth)acrylates having alkyl chain lengths in the range of 2 to 8 carbons. In an embodiment, the polymer includes poly(n-butyl)methacrylate. The polymer can include aromatic poly(meth)acrylate selected from the group consisting of polyaryl(meth)acrylate, polyaralkyl(meth)acrylate, and polyaryloxyalkyl(meth)acrylate. The aromatic poly(meth)acrylate can include aryl groups having from 6 to 16 carbon atoms. The coated composition can include poly(ethylene-co-vinyl acetate). In an embodiment, the poly(ethylene-co-vinyl acetate) has a vinyl acetate concentration in the range of 10% to 90% by weight. In an embodiment, the coated composition can include two or more layers. The medical device of claim can have a surface pretreatment coating. The surface pretreatment coating can include silane, polyurethane, parylene, or combinations thereof. The bioactive agent can be selected from the group consisting of triamcinolone acetonide, 13-cis retinoic acid, 5-fluorouridine, and combinations thereof. The coated composition can have a thickness of 0.1 μm to 100 μm.

In an embodiment, the invention includes a medical device with a substrate having a surface, a first coated composition having an edge provided on the substrate surface, the first coated composition comprising a first bioactive agent and a first polymer, a second coated composition having an edge provided on the substrate surface, the second coated composition comprising a second bioactive agent and a second polymer. In an embodiment, the first coated composition and the second coated composition do not overlap. In an embodiment, the first coated composition edge is within 0.5 mm of the second coated composition edge. In an embodiment, the first coated composition is configured to release the first bioactive agent more quickly than the second coated composition releases the second bioactive agent. In an embodiment, the first bioactive agent is the same as the second bioactive agent. In an embodiment, the first polymer is the same as the second polymer. The first coated composition edge can be within about 0.4 mm of the second coated composition edge. The first polymer, the second polymer, or both the first and second polymers, can include polyalkyl(meth)acrylate, aromatic poly(meth)acrylate, or a combination of polyalkyl (meth)acrylate and aromatic poly(meth)acrylate. The first polymer, the second polymer, or both the first and second polymers, can include polyalkyl(meth)acrylate selected from the group consisting of polyalkyl(meth)acrylates having alkyl chain lengths in the range of 2 to 8 carbons. In an embodiment, the first polymer, the second polymer, or both the first and second polymers, include poly(n-butyl)methacrylate. The first polymer, the second polymer, or both the first and second polymers, can include aromatic poly(meth)acrylate selected from the group consisting of polyaryl(meth)acrylate, polyaralkyl(meth)acrylate, and polyaryloxyalkyl (meth)acrylate. The aromatic poly(meth)acrylate can include aryl groups having from 6 to 16 carbon atoms. The first polymer, the second polymer, or both the first and second polymers, can include poly(ethylene-co-vinyl acetate). In an embodiment, the poly(ethylene-co-vinyl acetate) has a vinyl acetate concentration in the range of 10% to 90% by weight. The medical device can include a surface pretreatment coating. In an embodiment, the surface pretreatment coating comprises silane, polyurethane, parylene, or combinations thereof. In an embodiment, the first bioactive agent, the second bioactive agent, or both the first and second bioactive agents, are selected from the group consisting of triamcinolone acetonide, 13-cis retinoic acid, 5-fluorouridine, and combinations thereof. The coated composition can have a thickness of 0.1 μm to 100 μm.

In an embodiment, the invention includes a method for disposing a coated composition on a medical device with an ultrasonically atomized spray stream including atomizing a coating composition with an ultrasonic spray head, to produce a spray stream, moving the spray stream in a pattern having a plurality of transverse sweeps and a plurality of longitudinal movements, wherein the longitudinal movements are less than about 0.4 mm, wherein each longitudinal movement is separated from the next longitudinal movement by one or more transverse sweeps. In an embodiment, the medical device comprises a segment that remains uncoated by the coating composition, wherein the pattern is started at a point within about 0.5 mm of the segment that remains uncoated. The method can include continuously rotating the medical device to be coated simultaneously with the step of moving the spray stream. The step of atomizing can be performed simultaneously with the step of moving the spray stream. The spray stream can have a concentration point wherein greater than 90% of the coating composition passes through a space having a cross-sectional diameter of less than 1 mm. In an embodiment, the coating composition has a solids concentration of about 40 to about 80 mg/ml.

In an embodiment, the invention includes an implantable medical device having a cylindrical body defining a cylindrical space therein and a first coating including an active agent disposed on the cylindrical body. One or more adhesive bands are provided over the first coating, the adhesive bands covering not more than about 50% of the first coating surface area, the adhesive bands including at least 90% wt. pEVA. In an embodiment, the implantable medical device is a stent. In an embodiment, the adhesive bands have a length of about 2.0 mm or less.

The following examples illustrate the present invention without, however, limiting the same thereto.

EXAMPLES

Test Methods

The suitability of particular coated compositions for in vivo use can be determined by one or more of a variety of methods, including the Durability Test and Elution Assay. Examples of each test are described herein.

Sample Preparation

One-millimeter diameter stainless steel wires (for example, 316 L grade) were cut into 2-centimeter lengths. The wire segments were treated with a Parylene C coating composition (Union Carbide Corporation), as described herein. The wire segments were weighed on a micro-balance.

Coating compositions were prepared at a range of concentrations in an appropriate solvent, in the manner described herein. The coating mixtures were applied to respective wires, or portions thereof, by dipping or spraying, and the coated wires were allowed to dry by solvent evaporation. The coated wires were then re-weighed. From this weight, the mass of the coatings was calculated, which in turn permitted the mass of the coated polymer(s) and bioactive agent(s) to be determined.

Elution Assay

Any suitable Elution Assay can be used to determine the extent and/or rate of bioactive agent release from the coated composition under physiological conditions. In general, it is desirable that less than 50% of the total quantity of the drug to be released is released in the first 24 hours after introduction into physiological conditions. It is frequently desirable for quantities of bioactive agent to be released for a duration of at least 30 days. After all of the bioactive agent has been released, SEM evaluation should reveal an intact coated composition.

The Elution Assay utilized herein was as follows. Phosphate buffered saline (PBS, 10 mM phosphate, 150 mM NaCl, pH 7.4, aqueous solution) was pipetted in an amount of 3 ml to 10 ml into an amber vial with a Teflon™ lined cap. A wire or coil treated with the coating composition was immersed into the PBS. A stir bar was placed into the vial and the cap was screwed tightly onto the vial. The PBS was stirred with the use of a stir plate, and the temperature of the PBS was maintained at 37° C. with the use of a water bath. The sampling times were chosen based upon the expected or desired elution rate. At the sampling time point, the wire or coil was removed from the vial and placed into a new vial containing fresh PBS. A UV/Vis spectrophotometer was used to determine the concentration of the drug in the PBS solution that previously contained the wire or coil treated with the coating composition. The cumulative amount of drug eluted versus time was plotted to obtain an elution profile.

At the conclusion of the Elution Assay, the wire or coil was washed with water, dried and re-weighed. Correlation between the percent bioactive agent eluted and the percent weight loss of the coated composition was verified.

When desired, the coated composition can also be evaluated by measuring the coated composition thickness (for example, using a Minitest 4100 thickness gauge), and the coated composition quality (such as roughness, smoothness, evenness, and the like) can be analyzed by SEM analysis.

Nomenclature

The following abbreviations are used in the examples:

| | |
|---|---|
| pEVA | poly(ethylene-co-vinyl acetate) (SurModics, Inc., Eden Prairie, MN) |
| PBMA | poly(n-butyl)methacrylate (SurModics, Inc., Eden Prairie, MN) |
| TA | triamcinolone acetonide (Sigma-Aldrich Chemical, St. Louis, MO) |

In the following examples, the compositional details of each coating composition are summarized as a ratio of the weight percentages of polymers used to create the coating composition. For example, a coating composition designated TA/pEVA/PBMA (50/49/1) is made by providing, on a relative basis, 50 parts by weight triamcinolone acetonide, 49 parts by weight poly(ethylene-co-vinyl acetate), and 1 part by weight of poly(n-butyl)methacrylate.

Example 1

Release of Triamcinolone Acetonide from Stainless Steel Wires

Three different polymer solutions were prepared in tetrahydrofuran (THF) in the manner provided below in order to provide coating compositions in the form of a one-part system. The three solutions contained varying amounts of poly (ethylene-co-vinyl acetate), with a vinyl acetate content of 33%(w/w), relative to the amount of poly(n-butyl)methacrylate, with an approximate weight average molecular weight of 337 kD. Each of the three solutions contained a constant amount of triamcinolone acetonide relative to the total polymer weight.

The coating compositions were prepared as follows. The polymers were initially added to the THF and dissolved overnight while mixing on a shaker at 200 revolutions per minute (rpm) at room temperature (approximately 20° C. to 22° C.). After dissolution of the polymer, the triamcinolone acetonide was added, and the mixture was placed back on the shaker at 100 rpm for 1 hour, to form the one-part coating composition. The compositions prepared are summarized below in Table I:

TABLE I

Coating Compositions applied to wire surfaces.

| Coating | Composition | Parts by weight (pbw) | Weight of Coating Composition (μg) |
|---|---|---|---|
| Coating 1a | TA/pEVA/PBMA | 50/49/1 | 1222 |
| Coating 1b | TA/pEVA/PBMA | 50/36/14 | 1266 |
| Coating 1c | TA/pEVA/PBMA | 50/15/35 | 1204 |

Stainless steel wire samples were prepared for coating as follows. The stainless steel wire was cleaned by soaking in a 6% (by volume) solution of ENPREP-160SE (Cat. #2108-100, Enthone-OMI, Inc., West Haven, Conn.) in deionized water for 1 hour. After soaking, the parts were then rinsed several times with deionized water. After rinsing, the stainless steel wire was soaked for 1 hour at room temperature in 0.5% (by volume) methacryloxypropyltrimethoxy silane (Cat.#M6514, Sigma Aldrich, St. Louis, Mo.) made in a 50% (by volume) solution of deionized water and isopropyl alcohol. The stainless steel wires were allowed to drain and air dry. The dried wires were then placed in a 100° C. oven for 1 hour.

After oven-drying, the stainless steel wires were placed in a parylene coating reactor (PDS 2010 LABCOTER™ 2, Specialty Coating Systems, Indianapolis, Ind.) and coated with 2 g of Parylene C (Specialty Coating Systems, Indianapolis, Ind.) by following the operating instructions for the LABCOTER™ system. The resulting Parylene C coating was approximately 1-2 μm thickness.

Solutions for Coatings 1a, 1b, and 1c were sprayed onto the Parylene C treated wires using an IVEK sprayer (IVEK Dispenser 2000, IVEK Corp., North Springfield, Vt.) mounting a nozzle with a 1.0 mm (0.04 inch) diameter orifice and pressurized at 421.84 g/cm$^2$ (6 psi). The distance from the nozzle to the wire surface during coating application was 5 to 5.5 cm. A coating application consisted of spraying 40 μl of the coating solution back and forth on the wire for 7 seconds. The spraying process of the coating was repeated until the amount of TA on the wire equaled the amount of TA listed for Coatings 1a, 1b, and 1c seen in Graph I. The coating compositions on the wire were dried by evaporation of solvent, approximately 8-10 hours, at room temperature (approximately 20° C. to 22° C.). After drying, the coated wires were re-weighed. From this weight, the mass of the coating was calculated, which in turn permitted the mass of the coated polymer(s) and bioactive agent to be determined.

The coated wires were then subjected to the Elution Assay described above. Results of the Elution Assay for each coating composition are illustrated in Graph I below.

The release rates of the coatings were determined for greater than 175 days. For Coating 1c, the calculated release rate was 0.5 μg/day between days 51 and 456, and the release rate was linear over the duration of the experiment. For Coating 1a, the calculated release rate was 4.2 μg/day between days 14 and 79, and for Coating 1b, the calculated linear release rate was 1.2 μg/day between days 84 and 337. Utilizing these release rates, it was calculated that Coating 1c would be released from the coated composition into PBS (assuming 100% release of TA) for a period exceeding 3 years.

As shown in the graph, Coating 1a included an initial loading of 611 μg of TA, and 600 μg of the bioactive agent was released within 190 days. Coating 1b included an initial loading of 633 μg of TA, and 631 μg of the bioactive agent was released within 372 days. Coating 1c included an initial loading of 602 μg of TA, and 240 μg of the bioactive agent was released within 456 days.

Results indicate that a bioactive agent, in this case, triamcinolone acetonide, was predicted to elute from a coated composition according to the invention for surprisingly long periods of time in vitro (over three years). Further, the coating composition can provide a substantially linear release rate over time. Moreover, as the results indicate, the coated composition can be varied, for example, by varying the weight ratio of the first polymer and second polymer, to control the elution rate of a bioactive agent, such as triamcinolone acetonide, as desired. Thus, a treatment course can be identified by an interventionalist, and the polymeric coating composition according to the invention can be formulated to provide a controlled release profile to achieve the designated treatment course. As described in more detail herein, the release profile can be further controlled by controlling humidity conditions of the coating composition.

At the conclusion of the Elution Assay, the wire was washed with water, dried and re-weighed. Pre- and post-elution data for coated compositions 1a and 1b are provided in Table II below:

TABLE II

Elution Data for Coated Compositions 1a and 1b.

| Coating | Coated coil weight before elution (mg) | Coated coil weight after elution (mg) | Drug released (µg) | Drug initial (µg) | % released as shown by coil weight loss during elution | % released as indicated by UV spec. |
|---|---|---|---|---|---|---|
| 1a | 25.775 | 25.183 | 592 | 611 | 97 | 98 |
| 1b | 30.187 | 29.567 | 620 | 633 | 98 | 105 |

As shown in the results, the amount of drug released correlated well with the initial drug weight in the coated composition and with the percent released as indicated by the Elution Assay.

Example 2

In Vitro Release of Triamcinolone Acetonide from Helical Coils

Two different solutions were prepared in tetrahydrofuran (THF) as in Example 1. The compositions prepared are summarized in Table III:

TABLE III

Coating Compositions applied to the Helical Coil.

| Coating | Composition | Parts by weight (pbw) | Weight of coated composition (µg) |
|---|---|---|---|
| Coating 1d | TA/pEVA/pBMA | 50/27.5/22.5 | 1950 |
| Coating 1e | TA/pEVA/pBMA | 50/40/10 | 1928 |

Helical coils with attached caps were fabricated from the alloy MP35N™ (commercially available from ESPI, Ashland, Oreg.). The coils were cleaned in an alkaline solution, then rinsed with deionized water. The coils underwent additional cleaning using an isopropyl alcohol wash and rinse. The coils were dried and weighed prior to coating.

Solutions for Coatings 1d and 1e were sprayed onto the coils using ultrasonic coater equipment that consisted of an ultrasonic spray head (Sono-Tek Milton, N.Y.) and syringe pump system for the coating solution. A pin vise was used to hold the cap of the coil and the coil was held perpendicular to the spray head and rotated. The spray head was moved over the coil to apply the coating composition. The spraying process was continued until the amount of TA on the coils equaled the amount of TA listed for Coatings 1d and 1e listed in Table III. The coating compositions on the helical coil were dried by evaporation of solvent at room temperature (approximately 20° C. to 22° C.). After drying, the coated coils were re-weighed. From this weight, the mass of the coating was calculated, which in turn permitted the mass of the coated polymer(s) and bioactive agent to be determined.

The coated coils were then subjected to the Elution Assay described above. Results of the Elution Assay for each coating composition are illustrated in Graph II below.

The release of TA was monitored over 63 days. As shown in Graph II, Coating 1d included an initial drug load of 975 µg of TA and approximately 171 µg of the bioactive agent was released within 63 days. Coating 1e included an initial drug load of 914 µg of TA and approximately 371 µg of the bioactive agent was released within 63 days. For coating 1d, the calculated release rate was 1.6 µg/day between days 20 and 63. For coating 1e, the calculated the calculated release rate was 3.6 µg/day between days 20 and 63.

Similar to the results discussed in Example I, the elution data for Coatings 1d and 1e indicate that a bioactive agent can be predicted to elute from a coated composition according to the invention for surprisingly long periods of time in vitro. Further, the coating compositions again showed a substantially linear release rate over time (between days 20 and 63). Similar to Example I, results illustrated that the elution rate of the bioactive agent can be controlled by varying the coated composition.

At the conclusion of the Elution Assay, the coils were washed with water, dried, and reweighed. Pre- and post-elution data for coated composition 1d and 1e along with the percent released as indicated by the Elution Assay is provided in Table IV below:

TABLE IV

Elution Data for Coated Composition 1d and 1e.

| Coating | Coated coil weight before elution (mg) | Coated coil weight after elution (mg) | Drug released (µg) | Drug initial (µg) | % released as shown by coil weight loss during elution | % released as indicated by UV spec. |
|---|---|---|---|---|---|---|
| 1d | 32.392 | 32.213 | 179 | 975 | 19 | 18 |
| 1e | 33.204 | 32.817 | 387 | 913.5 | 42 | 41 |

As shown in the results, the percent of drug released as determined by the coil weight before and after elution correlated well with the percent of drug released as determined by UV spectroscopy.

Example 3

In Vivo Release of Triamcinolone Acetonide from Helical Coils

Ten coils were coated with two different formulations, Dose A and Dose B, and were implanted into the vitreous chamber of rabbit eyes to provide sustained release of triamcinolone acetonide. Table V summarizes the coating compositions applied to the coils in this Example. Dose B was designated a "fast release" coating, and this coating composition included a relatively larger ratio of pEVA to PBMA, as compared to the "slow release" Dose A coating composition.

The coating solutions were prepared according to the procedure described in Example I. The coating solutions were applied to the coils according to the procedure described in Example II. The coated coils were implanted into the vitreous chamber of rabbit eyes as follows. The conjunctiva was dissected and pulled away from the incision site, and an incision was made into the eyes utilizing a needle stick through the sclera. A self-starting coil that included a sharp tip was utilized to insert the coil into the vitreous chamber of the eye. The coils were inserted until the cap of the coils abutted the outer surface of the eye, and the conjunctiva was pulled over the cap at the conclusion of the insertion procedure.

Five of the Dose B and four of the Dose A coils were implanted for 29 days. One of the Dose A coils was implanted for 11 days. After explantation of the coils, the residual drug within the coated coils was determined. The coatings were dissolved, and the drug and polymer were separated. The HPLC analysis consisted of a C18 column, a gradient elution using acetonitrile and deionized water and UV detection. The results from the solution containing the drug was compared to a calibration curve created from freshly prepared working standards. The amount of drug released was calculated and plotted in Graph III below.

TABLE V

Coating Composition Applied to the Helical Coil.

| Coil # | Dose Formulation | Coating Formulation | Parts by weight | Weight of TA in the Coated Composition (μg) |
|---|---|---|---|---|
| 1 | A | TA/pEVA/pBMA | 50/10/40 | 950 |
| 2 | A | TA/pEVA/pBMA | 50/10/40 | 936 |
| 3 | A | TA/pEVA/pBMA | 50/10/40 | 1012 |
| 4 | A | TA/pEVA/pBMA | 50/10/40 | 911 |
| 5 | A | TA/pEVA/pBMA | 50/10/40 | 932 |
| 6 | B | TA/pEVA/pBMA | 50/27.5/22.5 | 981 |
| 7 | B | TA/pEVA/pBMA | 50/27.5/22.5 | 974 |
| 8 | B | TA/pEVA/pBMA | 50/27.5/22.5 | 957 |
| 9 | B | TA/pEVA/pBMA | 50/27.5/22.5 | 975 |
| 10 | B | TA/pEVA/pBMA | 50/27.5/22.5 | 965 |

Results indicated the amount of TA released within 11 and 29 days from the Dose A implanted coated coil was approximately 92 and 126 μg, respectively. The amount of TA released within 29 days from the Dose B implanted coil was approximately 275 μg. The amount of TA released from the "fast release" formulation, Dose B, was approximately 2.2 times the amount of TA released from the "slow release" formulation, Dose A.

The implanted materials appeared to be well tolerated by ocular tissue throughout the 29-day follow-up period. No anterior or vitreous chamber inflammation was observed at either the 1-week or 4-week post-operative examination. Similarly, there was no elevation of intraocular pressure or conjunctival thinning associated with the implant.

Example 4

Surface Roughness Measurement

Helical coils with attached caps were fabricated from the alloy MP35N™ (commercially available from ESPI, Ashland, Oreg.). Two coils were then sandblasted with silica particles having an average diameter of 50 microns. The roughness of the surface after sandblasting was measured using the vertical scanning interferometry mode of an optical ferometer (WYKO NT1100 Optical Profiling System) (Veeco Instruments, Inc. Woodbury, N.Y.). Six sections (approximately 155 μm×120 μm surface area each) were tested for each of the coils. Three separate roughness parameters were calculated for each section using VISION32 software (Version 2.303) for the WYKO NT1100: Roughness Average ($R_a$)—the arithmetic mean of the absolute values of the surface departures from the mean plane, Maximum Height (peak to valley distance) ($R_t$)—the vertical distance between the highest and lowest points over the entire dataset (highest and lowest single pixels), Average Maximum Height (average peak to valley distance) ($R_z$)—the average of the difference of the ten highest and ten lowest points in the dataset (10 highest and 10 lowest pixels—at least 4.6 μm apart from each other laterally). The data are summarized in Table VI below:

TABLE VI

| | Test Section | $R_a$ (nm) | $R_t$ (μm) | $R_z$ (μm) |
|---|---|---|---|---|
| Coil 1 | 1 | 625.03 | 8.51 | 6.78 |
| | 2 | 756.07 | 9.11 | 7.84 |
| | 3 | 686.93 | 13.92 | 10.75 |
| | 4 | 795.54 | 9.24 | 8.29 |
| | 5 | 782.50 | 15.27 | 11.78 |
| | 6 | 778.56 | 10.46 | 8.95 |
| | Avg. +/− (SD) | 737.44 (67.28) | 11.09 (2.82) | 9.07 (1.87) |
| Coil 2 | 1 | 790.22 | 10.88 | 8.34 |
| | 2 | 626.39 | 10.01 | 7.35 |
| | 3 | 1170.03 | 11.41 | 10.11 |
| | 4 | 628.17 | 10.77 | 7.87 |
| | 5 | 727.82 | 13.00 | 8.98 |
| | 6 | 863.89 | 10.91 | 8.94 |
| | Avg. +/− (SD) | 801.08 (202.96) | 11.17 (1.01) | 8.60 (0.97) |

Example 5

Durability of Different Configurations of Coatings

A coating solution was prepared in tetrahydrofuran (THF) as follows. pEVA and pBMA polymers were initially added to THF and dissolved overnight while mixing on a shaker at 200 revolutions per minute (rpm) at room temperature (approximately 20° C. to 22° C.). After dissolution of the polymer, triamcinolone acetonide was added, and the mixture was placed back on the shaker at 100 rpm for 1 hour, to form the coating composition. The resulting coating composition had a solids content by weight of 50% TA/27.5% pEVA/22.5% pBMA.

Helical coils with attached caps were fabricated from the alloy MP35N™ (commercially available from ESPI, Ashland, Oreg.). However, one of skill in the art will appreciate that many different materials may be used to create the helical coils. The coils were sandblasted. Silica particles having an average diameter of 50 microns were used to sandblast the surface of the coils. The roughness of the surface after sandblasting was between about 8.0-10.0 $R_z$ (μm), as measured according to Example 4 above. Portions of the coils were then cut from the end opposite the cap creating a tapered portion with a sharp tip. The surface of the tapered portion had a roughness of less than the sandblasted portion. The tapered portion and tip can together be referred to as a piercing portion or piercing segment. The coils were cleaned in an alkaline solution, then rinsed with deionized water. The coils underwent additional cleaning using an isopropyl alcohol wash and rinse. The coils were dried and weighed prior to coating.

The coating solution described above was sprayed onto the coils using ultrasonic coater equipment that consisted of an ultrasonic spray head (Sono-Tek Milton, N.Y.) and syringe pump system for the coating solution. A pin vise was used to hold the coil held perpendicular to the spray head and rotated. The spray head was moved back and forth over the coil in a grid-like pattern having a plurality of transverse sweeps and longitudinal movements to apply the coating composition.

Three different types of coating patterns were generated with the ultrasonic coater equipment: Group A: fully-covered tapered segments ("Thick-Tip"), Group B: partially-covered tapered segments ("Partial-Tip"), and Group C: non-covered tapered segments ("Tip-Free").

Figure 22:
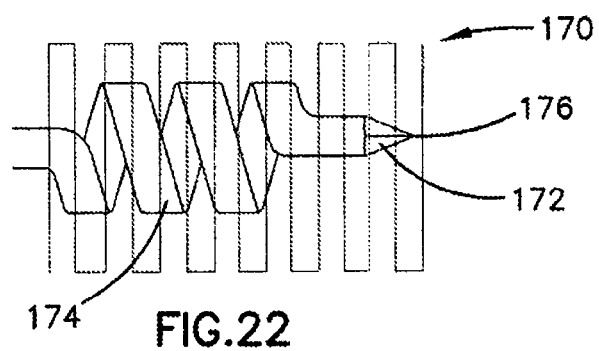
FIG. 22 is a schematic view of a grid-like coating pattern superimposed over an exemplary implantable device.

Thick-Tip: Fully-covered tapered segments were formed by having the grid-like pattern spray stream, such as shown in FIG. 22, start at a point beyond the end of the tip of the implantable tip and then work backward over the length of the implantable medical device. Fully-covered tapered segments were similar to that shown in FIG. 11, such that the coated composition completely covered the tapered segment and the tip of the coil, effectively blunting the sharpness of the tip. A plurality of grid-like pattern passes over the coil were made.

Figure 23:
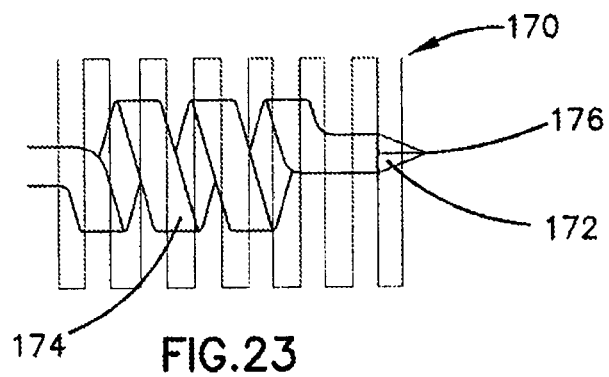
FIG. 23 is a schematic view of a grid-like coating pattern superimposed over an exemplary implantable device differently than in FIG. 22.

Partial-Tip: Partially-covered tapered segments were formed by having the grid-like pattern of the ultrasonic spray head spray stream start at a point over the tapered segment and then work backward over the length of the implantable medical device as shown in FIG. 23. Partially-covered tapered segments were similar to that shown in FIG. 12, such that at least some portions of the coated composition extended onto the smooth tapered portion. A plurality of grid-like pattern passes over the coil were made.

Figure 24:
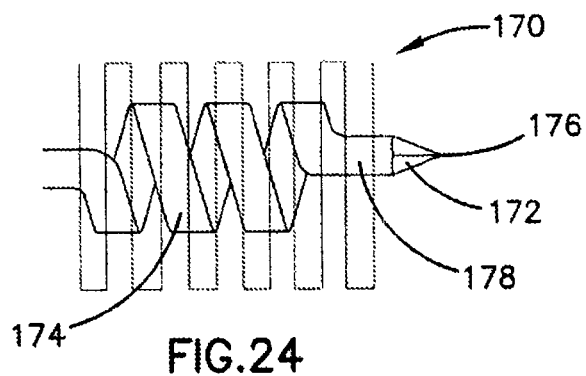
FIG. 24 is a schematic view of a grid-like coating pattern superimposed over an exemplary implantable device differently than in FIG. 23.
Figure 25:
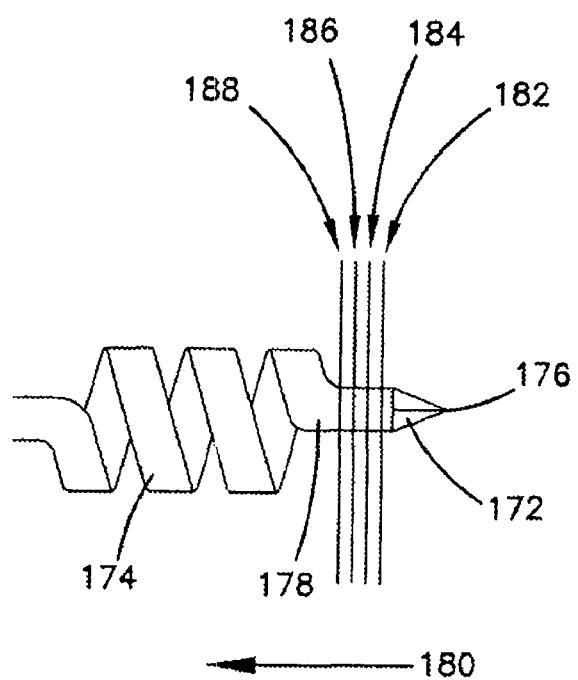
FIG. 25 is a schematic view of a series of first transverse sweeps superimposed over an exemplary implantable device.
Figure 26:
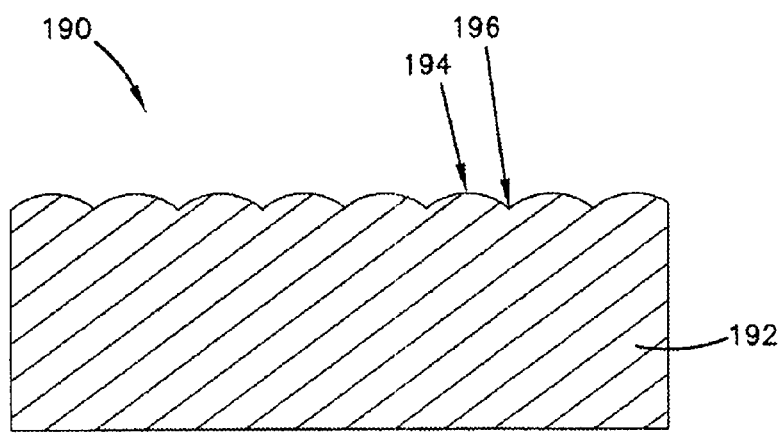
FIG. 26 shows a schematic cross-sectional view of a coating having a bumpy surface.

Tip-Free: Non-covered tapered segments were formed by having the grid-like pattern of the ultrasonic spray head spray stream start at a point over the rough segment within about 0.5 mm from the smooth tapered portion and then work backward over the length of the implantable medical device as shown in FIG. 24. Non-covered tapered segments were similar to that shown in FIG. 13, such that the coated composition did not extend onto the smooth tapered portion, but rather the coated composition had a leading edge disposed over the rough segment of the implantable medical device. A plurality of grid-like pattern passes over the coil were made.

The coating compositions on the helical coil were dried by evaporation of solvent at room temperature (approximately 20° C. to 22° C.). After drying, the coated coils were re-weighed. From this weight, the mass of the coated composition was calculated. The thick-tip group (n=8) had an average coated composition weight of 1801 µg. The partial-tip group (n=5) had an average coated composition weight of 1830 µg. The tip-free group (n=5) had an average coated composition weight of 1965 µg.

Next, silicone rubber sheets having Durometer hardness ratings of 40 shore A or 55 shore A were obtained from McMaster-Carr, Atlanta, Ga. The silicone rubber sheets were selected to provide a material for simulating insertion of the coil into a patient and simulate the frictional forces encountered by the implantable medical devices of the invention upon insertion and removal. The 40 shore A silicone rubber sheet had a thickness of approximately 1.5875 mm. The 55 shore A silicone rubber sheet had a thickness of approximately 0.508 mm.

For testing protocol 1 "Test 1", coated helical coils from the thick-tip, partial-tip, and tip-free groups were inserted and removed from the 55 shore A silicone rubber a total of 30 times. After each insertion and removal, each coil was visually inspected for damage. Specifically, each coil was inspected for tip delamination and tip coating failure. Tip delamination is defined as occurring when a region of the coated composition on the coil at or near the tip has detached from the metal substrate but is still linked to the rest of the coated composition. Tip coating failure is defined as occurring when some or all of the coating material at or near the tip has detached and fallen away leaving an exposed substrate. The data are summarized below in Table VII.

For testing protocol 2 "Test 2", coated helical coils from the thick-tip and tip-free groups were inserted and removed from the 40 shore A silicone rubber a total of 30 times. After each insertion and removal, each coil was visually inspected for damage. Specifically, each coil was inspected for tip delamination and tip coating failure. If tip delamination occurred after 10 cycles of insertion and retraction, then the individual device was given a score of 10. Where no damage was detected after 30 cycles the individual device was given a score of 30. Thus higher numbers indicate better performance. The average number of cycles before tip delamination or coating failure for each test group was then calculated. The data are summarized below in Table VII.

TABLE VII

| | | Tip Delamination (avg. cycles) | Tip Coating Failure (avg. cycles) |
|---|---|---|---|
| Test 1 | Thick Tip (n = 8) | 26.75 | 30 |
| | Partial-Tip (n = 5) | 2.2 | 11.4 |
| | Tip-Free (n = 5) | 30 | 30 |
| Test 2 | Thick Tip (n = 8) | 25.75 | 25.875 |
| | Tip-Free (n = 5) | 30 | 30 |

The results show that in Test 1 coils with a partially-covered tapered segment performed more poorly with respect to both tip delamination and tip coating failure than coils having a fully-covered tapered segment and coils having a non-covered tapered segment. Further, in Test 1, the coils with a non-covered tapered segment faired better with respect to tip delamination than either coils with a partially-covered tapered segment or coils with a fully-covered tapered segment. Test 2 showed that coils having a non-covered tapered segment performed better with respect to both tip delamination and tip coating failure than coils having a fully-covered tapered segment.

Accordingly, the data show that performance of the coated composition was enhanced when the leading edge of the coated composition was disposed over the roughened segment of the medical device. Stated in different terms, the data show that performance of the coated composition was enhanced when the coated composition was not disposed on the piercing segment of the medical device.

It was further observed during testing that additional force was required to insert the thick-tip devices into the silicone rubber. One of the thick-tip devices broke during the testing and it is believed that this was at least partially as a result of the additional force put on the device.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

I claim:

1. A medical device comprising:
a substrate having a surface;
a coating composition provided on the substrate surface, the coating composition comprising a bioactive agent and a polymer; and
an uncoated component-comprising a piercing segment;
wherein the coating composition is within 0.5 mm of the uncoated component without extending onto the piercing segment.

2. The medical device of claim 1, wherein the polymer comprises polyalkyl(meth)acrylate, aromatic poly(meth)acrylate, or a combination of polyalkyl(meth)acrylate and aromatic poly(meth)acrylate.

3. The medical device of claim 2, wherein the polymer comprises poly(n-butyl)methacrylate.

4. The medical device of claim 1, the coating composition further comprising poly(ethylene-co-vinyl acetate).

5. The medical device of claim 1, wherein the bioactive agent is selected from the group consisting of triamcinolone acetonide, 13-cis retinoic acid, 5-fluorouridine, and combinations thereof.

6. A medical device comprising: a substrate having a surface and a piercing segment; a first coating composition having an edge provided on the substrate surface, the first coating composition comprising a first bioactive agent and a first polymer; a second coating composition having an edge provided on the substrate surface, the second coating composition comprising a second bioactive agent and a second polymer; wherein the first coating composition and the second coating composition do not overlap; wherein the first coating composition edge is within 0.5 mm of the piercing segment, wherein neither the first coating or the second coating is disposed on the piercing segment.

7. The medical device of claim 6, wherein the first coating composition is configured to release the first bioactive agent more quickly than the second coating composition releases the second bioactive agent.

8. The medical device of claim 6, wherein the first polymer, the second polymer, or both the first and second polymers, comprise polyalkyl(meth)acrylate, aromatic poly(meth)acrylate, or a combination of polyalkyl(meth)acrylate and aromatic poly(meth)acrylate.

9. The medical device of claim 6, wherein the first polymer, the second polymer, or both the first and second polymers, comprise poly(n-butyl)methacrylate.

10. The medical device of claim 6, wherein the first polymer, the second polymer, or both the first and second polymers, comprise poly(ethylene-co-vinyl acetate).

11. The medical device of claim 6, wherein the first bioactive agent, the second bioactive agent, or both the first and second bioactive agents, are selected from the group consisting of triamcinolone acetonide, 13-cis retinoic acid, 5-fluorouridine, and combinations thereof.

12. The medical device of claim 1, wherein the edge of the coating composition is between 0.1 mm and 0.5 mm away from the uncoated component.

13. The medical device of claim 1, wherein the uncoated component is a cap.

14. An implantable medical device for intraocular delivery comprising:
 a substrate comprising a surface comprising a roughened segment and a smooth segment;
 a coating composition disposed on the roughened segment, the coating composition comprising a bioactive agent and a polymer; and
 the smooth segment comprising a piercing segment;
 wherein the coating composition is not disposed on the piercing segment.

15. The medical device of claim 14, the roughened segment having an $R_z$ of greater than 4.0 μm.

16. The medical device of claim 14, the smooth segment having an $R_z$ of less than 4.0 μm.

17. The medical device of claim 14, the coating composition comprising an edge adjacent to the smooth segment, the edge having a slope of less than 1.0.

18. The medical device of claim 17, the edge having a slope of less than 0.8.

* * * * *